(12) United States Patent
Shao et al.

(10) Patent No.: US 9,346,825 B2
(45) Date of Patent: *May 24, 2016

(54) FUSED BICYCLIC OXAZOLIDINONE CETP INHIBITOR

(71) Applicant: Merck Sharp & Dohme Corp., Rahway, NJ (US)

(72) Inventors: Pengcheng Patrick Shao, Fanwood, NJ (US); Wanying Sun, Edison, NJ (US); Revathi Reddy Katipally, Monmouth Junction, NJ (US); Petr Vachal, Summit, NJ (US); Feng Ye, Scotch Plains, NJ (US); Jian Liu, Edison, NJ (US); Deyou Sha, Yardley, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/480,202

(22) Filed: Sep. 8, 2014

(65) Prior Publication Data

US 2014/0378493 A1    Dec. 25, 2014

Related U.S. Application Data

(63) Continuation of application No. 13/660,010, filed on Oct. 25, 2012.

(60) Provisional application No. 61/552,592, filed on Oct. 28, 2011.

(51) Int. Cl.
| | |
|---|---|
| *C07D 498/04* | (2006.01) |
| *A61K 31/437* | (2006.01) |
| *A61K 31/4439* | (2006.01) |
| *A61K 45/06* | (2006.01) |
| *A61K 31/424* | (2006.01) |
| *A61K 31/444* | (2006.01) |
| *A61K 31/506* | (2006.01) |

(52) U.S. Cl.
CPC ............ *C07D 498/04* (2013.01); *A61K 31/424* (2013.01); *A61K 31/437* (2013.01); *A61K 31/444* (2013.01); *A61K 31/4439* (2013.01); *A61K 31/506* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 2006/0040999 A1 | 2/2006 | Ali et al. | |
| 2006/0223844 A1 | 10/2006 | Coleman | |
| 2009/0042892 A1 | 2/2009 | Ali et al. | |
| 2009/0075979 A1 | 3/2009 | Ali et al. | |
| 2009/0137548 A1 | 5/2009 | Ali et al. | |
| 2013/0331372 A1 | 12/2013 | Lu et al. | |

FOREIGN PATENT DOCUMENTS

| | | |
|---|---|---|
| EA | 200700259 A1 | 8/2007 |
| WO | 03011824 A1 | 2/2003 |
| WO | 2004/112699 A2 | 12/2004 |
| WO | 2005/097806 A1 | 10/2005 |
| WO | 2005/100298 A1 | 10/2005 |
| WO | 2005100298 A1 | 10/2005 |
| WO | 2007/075809 A2 | 7/2007 |
| WO | 2007/081571 A2 | 7/2007 |
| WO | 2010/039474 A1 | 4/2010 |
| WO | 2010039474 A1 | 4/2010 |
| WO | 2011028395 A1 | 3/2011 |
| WO | 2013165854 A1 | 11/2013 |

OTHER PUBLICATIONS

U.S. Appl. No. 13/660,010, filed Oct. 25, 2012.
Agami, et al., Chiral oxazolidinones from α-hydroxy oxazolidines: a new access to 1,2-amino alcohols, Tetrahedron: Asymmetry, 1998, 3955-3958, 9.
Davidson, MH, Update on CETP inhibition, Journal of Clinical Lipidology, 2010, 394-398, 4.
Kim, et al., Ring Opening of Homochiral Bicyclic Oxazolidinones: Synthesis of Allylglycinol Derivatives, Synthetic Communications, 1998, 1387-1397, 28(8).
Masterjohn, Chris, Effect of cholesteryl ester transfer protein inhibitor on vitamin E transport should be studied, American Heart Journal, 2009, e17, 158.
International Search Report mailed on Dec. 10, 2012 for PCT/US2012/061842, 8 pages.
Borsini; et al., "Intramolecular Palladium-Catalyzed Aminocarboxylation of Olefins as a Direct Route to Bicyclic Oxazolidinones", Advanced Synthesis & Catalysts, vol. 353, pp. 985-994, (2011).
Xiong Xuqiong, et al., "Progress in the study of the cholesteryl ester transfer protein inhibitors", Journal of Shenyang Pharmaceutical University, vol. 21, No. 4, Jul. 31, 2014 (plus English language abstract).

*Primary Examiner* — Kamal Saeed
(74) *Attorney, Agent, or Firm* — Eric A. Meade; Catherine D. Fitch

(57) ABSTRACT

Compounds having the structure of Formula I, including pharmaceutically acceptable salts of the compounds, are CETP inhibitors and are useful for raising HDL-cholesterol, reducing LDL-cholesterol, and for treating or preventing atherosclerosis.

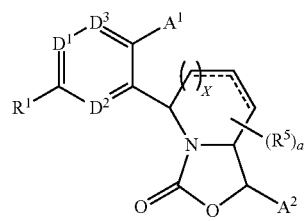

I

16 Claims, No Drawings

FUSED BICYCLIC OXAZOLIDINONE CETP INHIBITOR

CROSS REFERENCE TO RELATED APPLICATIONS

This application is a continuation under 35USC§120 of copending U.S. application Ser. No. 13/660,010, filed Oct. 25, 2012, which claim the benefit under 35 U.S.C.§119(e) of U.S. Provisional Application No. 61/552,592 filed Oct. 28, 2011. Each of the aforementioned U.S. Applications is hereby incorporated by reference in its entirety.

FIELD OF THE INVENTION

This invention relates to chemical compounds that inhibit cholesterol ester transfer protein (CETP) and are expected to have utility in raising HDL-C, lowering LDL-C, and in the treatment and prevention of atherosclerosis.

BACKGROUND OF THE INVENTION

Atherosclerosis and its clinical consequences, including coronary heart disease (CHD), stroke and peripheral vascular disease, represent a truly enormous burden to the health care systems of the industrialized world. In the United States alone, approximately 13 million patients have been diagnosed with CHD, and greater than one half million deaths are attributed to CHD each year. Further, this toll is expected to grow over the next quarter century as an epidemic in obesity and diabetes continues to grow.

It has long been recognized that in mammals, variations in circulating lipoprotein profiles correlate with the risk of atherosclerosis and CHD. The clinical success of HMG-CoA reductase inhibitors, especially the statins, in reducing coronary events is based on the reduction of circulating low density lipoprotein cholesterol (LDL-C), levels of which correlate directly with an increased risk for atherosclerosis. More recently, epidemiologic studies have demonstrated an inverse relationship between high density lipoprotein cholesterol (HDL-C) levels and atherosclerosis, leading to the conclusion that low serum HDL-C levels are associated with an increased risk for CHD.

Metabolic control of lipoprotein levels is a complex and dynamic process involving many factors. One important metabolic control in man is the cholesteryl ester transfer protein (CETP), a plasma glycoprotein that catalyzes the movement of cholesteryl esters from HDL to the apoB containing lipoproteins, especially VLDL (see Hesler, C. B., et. al. (1987) *Purification and characterization of human plasma cholesteryl ester transfer protein. J. Biol. Chem.* 262(5), 2275-2282)). Under physiological conditions, the net reaction is a heteroexchange in which CETP carries triglyceride to HDL from the apoB lipoprotein and transports cholesterol ester from HDL to the apoB lipoprotein.

In humans, CETP plays a role in reverse cholesterol transport, the process whereby cholesterol is returned to the liver from peripheral tissues. Intriguingly, many animals do not possess CETP, including animals that have high HDL levels and are known to be resistant to coronary heart disease, such as rodents (see Guyard-Dangremont, V., et. al., (1998) *Phospholipid and cholesteryl ester transfer activities in plasma from 14 vertebrate species. Relation to atherogenesis susceptibility, Comp. Biochem. Physiol. B Biochem. Mol. Biol.* 120 (3), 517-525). Numerous epidemiologic studies correlating the effects of natural variation in CETP activity with respect to coronary heart disease risk have been performed, including studies on a small number of known human null mutations (see Hirano, K.-I., Yamashita, S, and Matsuzawa, Y. (2000) *Pros and cons of inhibiting cholesteryl ester transfer protein, Curr. Opin. Lipidol.* 11(6), 589-596). These studies have clearly demonstrated an inverse correlation between plasma HDL-C concentration and CETP activity (see Inazu, A., et. al. (2000) *Cholesteryl ester transfer protein and atherosclerosis, Curr. Opin. Lipidol.* 11(4), 389-396), leading to the hypothesis that pharmacologic inhibition of CETP lipid transfer activity may be beneficial to humans by increasing levels of HDL-C while lowering LDL-C.

Despite the significant therapeutic advance that statins such as simvastatin and atorvastatin represent, statins only achieve a risk reduction of approximately one-third in the treatment and prevention of atherosclerosis and ensuing atherosclerotic disease events. Currently, few pharmacologic therapies are available that favorably raise circulating levels of HDL-C. Certain statins and some fibrates offer modest HDL-C gains. Niacin provides an effective therapy for raising HDL-C but suffers from patient compliance issues, due in part to side effects such as flushing. Drugs that inhibit CETP (CETP inhibitors) have been under development with the expectation that they will effectively raise HDL cholesterol levels and also reduce the incidence of atherosclerosis in patients. Torcetrapib was the first drug that was tested in a long-term outcomes clinical trial. The clinical trial of torcetrapib was terminated early due to a higher incidence of mortality in patients to whom torcetrapib and atorvastatin were administered concomitantly compared with patients who were treated with atorvastatin alone. The cause of the increased mortality is not completely understood, but it is not believed to be associated with the CETP inhibiting effects of the drug. Dalcetrapib was recently tested in a Phase III outcomes trial, which was terminated early because the interim data did not show a clinical benefit. There were no safety issues detected for dalcetrapib.

Anacetrapib is currently the only CETP inhibitor being tested in a large scale Phase III clinical outcomes trial. Data from the recently completed DEFINE Phase II/III trial of anacetrapib are promising. Patients who were treated with anacetrapib along with baseline statin therapy showed an increase of HDL-C of 138% and a decrease of LDL-C of 40% compared with patients who were treated with just a statin. See: *N. Engl. J. Med.* 2010:363:2406-15. The DEFINE study was not carried out on a large enough scale to serve as a pivotal outcomes trial, but the data in the DEFINE trial were sufficient to indicate that an increase in mortality for patients treated with anacetrapib is unlikely. Additional drug candidates are in development. Evacetrapib currently appears to be the next CETP inhibitor that will proceed to a Phase III outcomes trial. Additional compounds are being sought that may have properties that are advantageous compared with the CETP inhibitors that have so far been studied or are currently being studied. Such properties may include, for example, higher potency, reduced off-target activity, better pharmacodynamics, higher bioavailability, or a reduced food effect compared with many of the highly lipophilic compounds that have so far been studied. "Food effect" refers to the variability in exposure to the active drug that occurs depending on when the patient had last eaten, whether or not the drug is administered with food, and the fat content of the food.

SUMMARY OF THE INVENTION

The compound of Formula I, or a pharmaceutically acceptable salt thereof, is a potent CETP inhibitor, having the utilities described below:

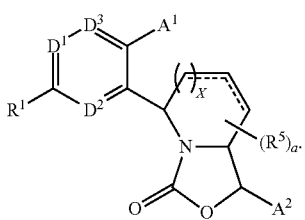

I

In Formula I, $R^1$ is H, $—C_1-C_5$ alkyl, $—OC_1-C_5$ alkyl, $—C_2-C_5$ alkenyl, $—OC_2-C_5$ alkenyl, $—C_2-C_5$ alkynyl, $—OC_2-C_5$ alkynyl, $—OH$, halogen, $—CN$, $—NR^6R^7$, $—CO_2R^8$, $—C(O)NR^6R^7$, $—SO_2NR^6R^7$, HET(3), or $C_{3-6}$ cycloalkyl optionally having 1-2 double bonds, wherein $—C_1-C_5$ alkyl, $—OC_1-C_5$ alkyl, $—C_2-C_5$ alkenyl, $—OC_2-C_5$ alkenyl, $—C_2-C_5$ alkynyl, and $—OC_2-C_5$ alkynyl are each optionally substituted with 1-7 halogens, and wherein HET(3) and $C_{3-6}$ cycloalkyl optionally having 1-2 double bonds are optionally substituted with 1-3 substituent groups which are each independently halogen, $—C_1-C_3$ alkyl, $—OC_1-C_3$ alkyl, $—C_2-C_3$ alkenyl, $—OC_2-C_3$ alkenyl, $—C_2-C_3$ alkynyl, or $—OC_2-C_3$ alkynyl, wherein $—C_1-C_3$ alkyl, $—OC_1-C_3$ alkyl, $—C_2-C_3$ alkenyl, $—OC_2-C_3$ alkenyl, $—C_2-C_3$ alkynyl, and $—OC_2-C_3$ alkynyl are each optionally substituted with 1-7 halogens;

$R^6$ and $R^7$ are each independently H or $—C_1-C_5$ alkyl;

$R^8$ is H or $—C_{1-5}$ alkyl optionally substituted with 1-7 halogens;

HET(3) is a 3-6 membered heterocyclic ring having 1-3 heteroatom groups which are each independently N, NH, O, S, S(O), or $S(O)_2$ and optionally having 1-3 double bonds;

x is 0 or 1;

The dashed lines in Formula I represent one optional double bond between 2 adjacent carbon atoms;

$D^1$ is N or $CR^2$;

$D^2$ is N or $CR^3$;

$D^3$ is N or $CR^4$;

$R^2$, $R^3$, and $R^4$ are each independently H, $—C_1-C_5$ alkyl, $—OC_1-C_5$alkyl, $—C_2-C_5$ alkenyl, $—OC_2-C_5$ alkenyl, $—C_2-C_5$ alkynyl, $—OC_2-C_5$ alkynyl, $—OH$, halogen, $—CN$, $—NR^6R^7$, $—CO_2R^8$, $—C(O)NR^6R^7$, or $—SO_2NR^6R^7$, wherein $—C_1-C_5$ alkyl, $—OC_1-C_5$ alkyl, $—C_2-C_5$ alkenyl, $—OC_2-C_5$ alkenyl, $—C_2-C_5$ alkynyl, and $—OC_2-C_5$ alkynyl are optionally substituted with 1-7 halogens;

Each $R^5$ is independently $—C_1-C_5$ alkyl, $—OC_1-C_5$ alkyl, $—C_2-C_5$ alkenyl, $—OC_2-C_5$ alkenyl, $—C_2-C_5$ alkynyl, $—OC_2-C_5$ alkynyl, $—OH$, halogen, $—CN$, $—NR^6R^7$, $—CO_2R^8$, $—C(O)NR^6R^7$, or $—SO_2NR^6R^7$, wherein $—C_1-C_5$ alkyl, $—OC_1-C_5$ alkyl, $—C_2-C_5$ alkenyl, $—OC_2-C_5$ alkenyl, $—C_2-C_5$ alkynyl, and $—OC_2-C_5$ alkynyl are optionally substituted with 1-7 halogens;

$A^1$ is phenyl, HET(1), or $C_3-C_9$ cycloalkyl optionally having 1-2 double bonds, wherein $A^1$ is optionally substituted with one substituent group Z and is optionally substituted with 1-3 groups which are each independently $—C_1-C_5$ alkyl, $—OC_1-C_5$ alkyl, $—C_2-C_5$ alkenyl, $—OC_2-C_5$ alkenyl, $—C_2-C_5$ alkynyl, $—OC_2-C_5$ alkynyl, halogen, $—OH$, or $—CN$, wherein $—C_1-C_5$ alkyl, $—OC_1-C_5$ alkyl, $—C_2-C_5$ alkenyl, $—OC_2-C_5$ alkenyl, $—C_2-C_5$ alkynyl, and $—OC_2-C_5$ alkynyl are optionally substituted with 1-7 halogens;

Each HET(1) is a 5- or 6-membered heterocyclic ring having 1-4 heteroatom groups which are each independently $—N—$, $—NH—$, $—S—$, $—O—$, $—S(O)—$, or $—S(O)_2—$, optionally having one group $—C(=O)—$, and optionally having 1-3 double bonds;

Z is $A^3$, $—C_1-C_3$ alkylene-$CO_2R^8$, $—C_1-C_3$ alkylene-$C(O)NR^6R^7$, $—C_1-C_3$ alkylene-$SO_2NR^6R^7$, $—CO_2R^8$, $—C(O)NR^6R^7$, $—SO_2NR^6R^7$, or $—C_1-C_3$alkylene-HET(2), wherein $—C_1-C_3$alkylene in all uses is optionally substituted with 1-7 halogens, and HET(2) is optionally substituted with 1-3 substituents which are independently $—C_{1-3}$alkyl optionally substituted with 1-5 halogens, $—OC_1-C_3$alkyl optionally substituted with 1-5 halogens, halogen or $NR^6R^7$.

$A^3$ is phenyl, $C_3-C_6$ cycloalkyl optionally having 1-2 double bonds, or HET(1), wherein $A^3$ is optionally substituted with 1-3 groups which are each independently $—C_1-C_5$ alkyl, $—OC_1-C_5$ alkyl, $—C_2-C_5$ alkenyl, $—OC_2-C_5$ alkenyl, $—C_2-C_5$ alkynyl, $—OC_2-C_5$ alkynyl, halogen, $—OH$, or $—CN$, wherein $—C_1-C_5$ alkyl, $—OC_1-C_5$ alkyl, $—C_2-C_5$ alkenyl, $—OC_2-C_5$ alkenyl, $—C_2-C_5$ alkynyl, and $—OC_2-C_5$ alkynyl are optionally substituted with 1-7 halogens; and $A^3$ is optionally substituted with one group which is HET(2), $—C_{1-4}$ alkylene-$CO_2R^8$, $—C_{1-4}$alkylene-$C(O)NR^6R^7$, $—C_1-C_4$alkylene-$SO_2NR^6R^7$, $—CO_2R^8$, $—C(O)NR^6R^7$, or $—SO_2NR^6R^7$, wherein $—C_1-C_4$alkylene in all uses is optionally substituted with 1-7 halogens; and wherein HET(2) is optionally substituted with 1-3 groups which are each independently halogen, $—C_{1-5}$alkyl optionally substituted with 1-7 halogens, $—OC_{1-5}$alkyl optionally substituted with 1-7 halogens, or $NR^6R^7$;

HET(2) is a 5-6 membered heterocyclic ring having 1-3 heteroatom groups which are each independently N, NH, O, or S, optionally having one group $—C(=O)$, and optionally having 1-3 double bonds;

$A^2$ is phenyl or HET(1), wherein $A^2$ is optionally substituted with 1-3 substituent groups which are each independently $—C_1-C_5$ alkyl, $—OC_1-C_5$ alkyl, $—C_2-C_5$ alkenyl, $—OC_2-C_5$ alkenyl, $—C_2-C_5$alkynyl, $—OC_2-C_5$alkynyl, halogen, $—CN$, $—OH$, or $C_{3-6}$cycloalkyl, wherein $—C_1-C_5$ alkyl, $—OC_1-C_5$ alkyl, $—C_2-C_5$ alkenyl, $—OC_2-C_5$ alkenyl, $—C_2-C_5$alkynyl, and $—OC_2-C_5$ alkynyl are optionally substituted with 1-7 halogens, and $C_{3-6}$cycloalkyl is optionally substituted with 1-3 substituents which are each independently halogen, $—C_1-C_3$ alkyl, or $—OC_1-C_3$ alkyl, wherein $—C_1-C_3$ alkyl and $—OC_1-C_3$ alkyl are each optionally substituted with 1-7 halogens; and a is 0 or an integer from 1-3.

In the compound of Formula I or Formula Ia, and in subgroups and other embodiments of the invention, alkyl groups and substituents based on alkyl groups, such as alkoxy, may be linear or branched unless otherwise indicated.

In general, references to the compound(s) of formula I or Ia are meant to also include subsets of compounds of formula I and Ia as may be defined herein, and also are meant to include the specific numbered examples provided herein.

DETAILED DESCRIPTION OF THE INVENTION

In further embodiments of the invention, the substituent groups defined above may have alternative values independent of one another, as written below. Such embodiments include pharmaceutically acceptable salts when such salts are possible.

In many embodiments, $R^1$ is $—C_1-C_5$alkyl, $—OC_1-C_5$ alkyl, halogen, $—NR^6R^7$, HET(3), or $C_{3-6}$ cycloalkyl optionally having 1-2 double bonds, wherein —$C_1$-$C_5$ alkyl and —$OC_1$-$C_5$ alkyl are optionally substituted with 1-7 halogens, and wherein HET(3) and $C_{3-6}$ cycloalkyl optionally having 1-2 double bonds are optionally substituted with 1-3 substituent groups which are each independently halogen, $CH_3$, $CF_3$, $OCH_3$, or $OCF_3$.

In many embodiments, $R^1$ is $CH_3$, $CF_3$, —$OCH_3$, —$OCF_3$, halogen, or —$NR^6R^7$.

In many embodiments, $R^1$ is $CH_3$, $CF_3$, —$OCH_3$, —$OCF_3$, F, Cl, or —$NR^6R^7$.

In many embodiments, $R^1$ is $CF_3$, F, or —$N(CH_3)_2$.

In many embodiments, $R^6$ and $R^7$ are each independently H or —$C_1$-$C_3$ alkyl.

In many embodiments, $R^6$ and $R^7$ are each independently H or —$CH_3$.

In many embodiments, $R^2$, $R^3$, and $R^4$ are each independently H, —$C_1$-$C_5$ alkyl, —$OC_1$-$C_5$ alkyl, or halogen, wherein —$C_1$-$C_5$ alkyl and —$OC_1$-$C_5$ alkyl are optionally substituted with 1-7 halogens.

In many embodiments, $R^2$, $R^3$, and $R^4$ are each independently H, $C_{1-3}$alkyl, —$OC_{1-3}$alkyl, or halogen, wherein —$C_1$-$C_3$ alkyl and —$OC_1$-$C_3$ alkyl are optionally substituted with 1-3 halogens.

In many embodiments, $R^2$, $R^3$, and $R^4$ are each independently of one another —$C_{1-3}$alkyl, F, or Cl.

In many embodiments, $R^2$ is H, $CH_3$, or —$CH(CH_3)_2$.

In many embodiments, $R^2$ is H or —$C_{1-3}$alkyl.

In many embodiments, $R^2$ is H or —$C_{1-3}$alkyl, and $R^3$ and $R^4$ are each independently of $R^2$ and of each other H or $CH_3$.

In many embodiments, $R^3$ is H or —$C_{1-3}$alkyl.

In many embodiments, $R^4$ is H or —$C_{1-3}$alkyl.

In many embodiments, at least one of $D^1$, $D^2$, or $D^3$ is $CR^2$, $CR^3$, or $CR^4$.

In many embodiments, each $R^5$ is independently —$C_1$-$C_5$ alkyl, —$OC_1$-$C_5$ alkyl, or halogen, wherein —$C_1$-$C_5$ alkyl and —$OC_1$-$C_5$ alkyl are optionally substituted with 1-7 halogens.

In many embodiments, each $R^5$ is independently $CH_3$, $CF_3$, —$OCH_3$, —$OCF_3$, or halogen.

In many embodiments, $R^5$ is H or $CH_3$.

In many embodiments, $R^8$ is H or —$C_{1-3}$alkyl optionally substituted with 1-3 halogens.

In many embodiments, $R^8$ is H or —$CH_3$.

In many embodiments, $A^1$ is phenyl, HET(1), or $C_3$-$C_6$ cycloalkyl optionally having 1-2 double bonds, wherein $A^1$ is optionally substituted with one substituent group Z and is optionally substituted with 1-3 groups which are each independently halogen, —OH, —CN, —$C_{1-5}$alkyl optionally substituted with 1-7 halogens, or —$OC_{1-5}$alkyl optionally substituted with 1-7 halogens.

In many embodiments, $A^1$ is phenyl, HET(1), or $C_3$-$C_6$ cycloalkyl optionally having 1-2 double bonds, wherein $A^1$ is optionally substituted with one substituent group Z and is optionally substituted with 1-3 groups which are each independently —$C_{1-3}$alkyl optionally substituted with 1-5 halogens, —$OC_{1-3}$alkyl optionally substituted with 1-5 halogens, halogen, —OH, or —CN.

In many embodiments, $A^1$ is phenyl, pyridinyl, pyrazinyl, pyrimidinyl, pyridazinyl, pyrazolyl, imidazolyl, isoxazolyl, thiazolyl, oxadiazolyl, thiadiazolyl, oxazolyl, pyrrolyl, thienyl, furyl, cyclopropyl, cyclobutyl, cyclohexyl, cyclohexenyl, cyclopentyl, or cyclopentenyl, wherein $A^1$ is optionally substituted with 1-3 groups which are each independently F, Cl, —$OCH_3$, —$OCF_3$, —$C_{1-3}$alkyl, —CN, or $CF_3$, and optionally one substituent group Z.

In many embodiments, $A^1$ is phenyl, pyridinyl, pyrazinyl, pyrimidinyl, pyridazinyl, pyrazolyl, imidazolyl, isoxazolyl, thiazolyl, oxadiazolyl, thiadiazolyl, oxazolyl, pyrrolyl, thienyl, furyl, cyclopropyl, cyclobutyl, cyclohexyl, cyclohexenyl, cyclopentyl, or cyclopentenyl, wherein $A^1$ is optionally substituted with 1-3 groups which are each independently F, Cl, —$OCH_3$, —$OCF_3$, isopropyl, —CN, —$CH_3$, or $CF_3$, and optionally one substituent group Z.

In many embodiments, $A^1$ is phenyl, pyridyl, thienyl, furyl, cyclohexenyl, or cyclopentenyl, wherein $A^1$ is optionally substituted with 1-3 groups which are each independently F, Cl, —$OCH_3$, isopropyl, —CN, —$CH_3$, or $CF_3$, and optionally one substituent group Z.

In many embodiments, $A^2$ is phenyl or HET(1), wherein $A^2$ is optionally substituted with 1-3 substituent groups which are each independently $C_{1-5}$alkyl optionally substituted with 1-7 halogens, —$OC_{1-5}$alkyl optionally substituted with 1-7 halogens, halogen, —OH, —CN, or $C_{3-6}$cycloalkyl optionally substituted with 1-3 substituents which are each independently halogen, $CF_3$, $CH_3$, —$OCF_3$, or —$OCH_3$.

In many embodiments, $A^2$ is phenyl or HET(1), wherein $A^2$ is substituted with 1-3 substituent groups which are each independently $C_{1-5}$alkyl optionally substituted with 1-7 halogens, —$OC_{1-5}$alkyl optionally substituted with 1-7 halogens, halogen, —OH, —CN, or $C_{3-6}$cycloalkyl optionally substituted with 1-3 substituents which are each independently halogen, $CF_3$, $CH_3$, —$OCF_3$, or —$OCH_3$.

In many embodiments, $A^2$ is phenyl or HET(1), wherein $A^2$ is substituted with 1-3 substituent groups which are each independently $CH_3$, $CF_3$, —$OCH_3$, —$OCF_3$, halogen, —CN, —OH, or $C_{3-4}$cycloalkyl optionally substituted with 1-3 substituents which are each independently halogen, $CF_3$, $CH_3$, —$OCF_3$, or —$OCH_3$.

In many embodiments, $A^2$ is phenyl or HET(1) wherein $A^2$ is substituted with 1-3 substituent groups which are each independently $CF_3$, $CH_3$, F, Cl, —CN, or cyclopropyl.

In many embodiments, $A^2$ is phenyl, which is substituted with 1-2 substituent groups which are each independently $CF_3$, $CH_3$, F, or Cl.

In many embodiments, $A^3$ is phenyl, $C_3$-$C_6$ cycloalkyl optionally having 1-2 double bonds, or HET(1), wherein $A^3$ is optionally substituted with 1-3 groups which are each independently —$C_1$-$C_5$ alkyl optionally substituted with 1-7 halogens, —$OC_1$-$C_5$ alkyl optionally substituted with 1-7 halogens, —OH, or halogen, and is optionally substituted with one group which is HET(2), —$C_{1-2}$ alkylene-$CO_2R^8$, —$C_{1-2}$ alkylene-C(O)$NR^6R^7$, —$C_1$-$C_2$alkylene-$SO_2NR^6R^7$, —$CO_2R^8$, —C(O)$NR^6R^7$, or —$SO_2NR^6R^7$, wherein —$C_1$-$C_2$alkylene is optionally substituted with 1-3 halogens; and wherein HET(2) is optionally substituted with 1-3 groups which are each independently halogen, —$C_{1-5}$alkyl optionally substituted with 1-7 halogens, —$OC_{1-5}$alkyl optionally substituted with 1-7 halogens, or $NR^6R^7$.

In many embodiments, $A^3$ is phenyl, $C_3$-$C_6$ cycloalkyl optionally having 1-2 double bonds, or HET(1), wherein $A^3$ is optionally substituted with 1-3 groups which are each independently —$C_1$-$C_5$ alkyl optionally substituted with 1-7 halogens, —$OC_1$-$C_5$ alkyl optionally substituted with 1-7 halogens, or halogen, and is optionally substituted with one group which is HET(2), —$C_{1-2}$ alkylene-$CO_2R^8$, —$C_{1-2}$alkylene-C(O)$NR^6R^7$, —$C_1$-$C_2$alkylene-$SO_2NR^6R^7$, —$CO_2R^8$, —C(O)$NR^6R^7$, or —$SO_2NR^6R^7$, wherein —$C_1$-$C_2$alkylene is optionally substituted with 1-3 halogens; and wherein HET(2) is optionally substituted with 1-3 groups which are each independently halogen, —$C_{1-5}$alkyl optionally substituted with 1-7 halogens, —$OC_{1-5}$alkyl optionally substituted with 1-7 halogens, or $NR^6R^7$.

In many embodiments, $A^3$ is phenyl, $C_3$-$C_6$ cycloalkyl, or HET(1), wherein $A^3$ is optionally substituted with 1-3 groups which are each independently CH$_3$, CF$_3$, —OCH$_3$, —OCF$_3$, or halogen, and is optionally substituted with one group which is HET(2), —(CH$_2$)$_{1-2}$—CO$_2$R$^8$, —(CH$_2$)$_{1-2}$—C(O)NR$^6$R$^7$, —(CH$_2$)$_{1-2}$—SO$_2$NR$^6$R$^7$, —CO$_2$R$^8$, —C(O)NR$^6$R$^7$, or —SO$_2$NR$^6$R$^7$, and HET(2) is optionally substituted with 1-3 groups which are each independently CH$_3$, CF$_3$, —OCH$_3$, —OCF$_3$, halogen, or NR$^6$R$^7$.

In many embodiments, A$^3$ is phenyl, C$_3$-C$_6$ cycloalkyl optionally having 1-2 double bonds, or HET(1), wherein A$^3$ is optionally substituted with 1-3 groups which are each independently CH$_3$, CF$_3$, —OCH$_3$, —OCF$_3$, —OH, or halogen, and is optionally substituted with one group which is HET(2), —(CH$_2$)$_{1-2}$—CO$_2$R$^8$, —(CH$_2$)$_{1-2}$—C(O)NR$^6$R$^7$, —(CH$_2$)$_{1-2}$—SO$_2$NR$^6$R$^7$, —CO$_2$R$^8$, —C(O)NR$^6$R$^7$, or —SO$_2$NR$^6$R$^7$, and HET(2) is optionally substituted with 1-3 groups which are each independently CH$_3$, CF$_3$, —OCH$_3$, —OCF$_3$, halogen, or NR$^6$R$^7$.

In many embodiments, A$^3$ is phenyl, pyridyl, pyrazinyl, pyrimidinyl, pyridazinyl, pyrazolyl, imidazolyl, isoxazolyl, thiazolyl, oxadiazolyl, thiadiazolyl, oxazolyl, pyrrolyl, thienyl, furyl, cyclopropyl, cyclobutyl, cyclohexyl, cyclohexenyl, cyclopentyl, or cyclopentenyl, wherein A$^3$ is optionally substituted with 1-2 groups which are each independently CH$_3$, CF$_3$, —OCH$_3$, —OCF$_3$, or halogen, and is optionally substituted with 1 group which is —CO$_2$R$^8$, —C(O)NR$^6$R$^7$, —SO$_2$NR$^6$R$^7$, or HET(2), wherein HET(2) is optionally substituted with 1-2 substituent groups which are each independently CH$_3$, CF$_3$, —OCH$_3$; —OCF$_3$, halogen, or NR$^6$R$^7$.

In many embodiments, A$^3$ is phenyl, cyclopropyl, cyclobutyl, cyclohexyl, cyclohexenyl, cyclopentyl, cyclopentenyl, or HET(1), wherein HET(1) is pyridinyl, pyrazinyl, pyrimidinyl, pyridazinyl, pyrazolyl, imidazolyl, isoxazolyl, thiazolyl, oxadiazolyl, thiadiazolyl, oxazolyl, pyrrolyl, thienyl, furyl, or a 5-6-membered heterocyclic ring having 1-2 heteroatom groups which are independently —N—, —NH— or —O—, and optionally one —C(=O)— group, wherein A$^3$ is optionally substituted with 1-2 groups which are each independently CH$_3$, CF$_3$, —OCH$_3$, —OCF$_3$, —OH, or halogen, and is optionally substituted with 1 group which is —CO$_2$R$^8$, —C(O)NR$^6$R$^7$, —SO$_2$NR$^6$R$^7$, or HET(2), wherein HET(2) is optionally substituted with 1-2 substituent groups which are each independently CH$_3$, CF$_3$, —OCH$_3$; —OCF$_3$, halogen, or NR$^6$R$^7$.

In many embodiments, A$^3$ is phenyl, cyclobutyl, cyclopentyl, cyclohexyl, or HET(1), wherein HET(1) is pyridinyl, 6-oxopiperidinyl, 2-oxo-1,3-oxazolidinyl, 2-oxo-1,3-oxazinanyl, or 5-oxopyrrolidinyl, wherein A$^3$ is optionally substituted with 1-2 groups —CH$_3$, —OCH$_3$, or —OH, and is optionally substituted with 1 group-(5-oxo-4,5-dihydro-1,3,4-oxadiazol-2-yl), -(5-amino-1,3,4-oxadiazol-2-yl), or —CO$_2$R in which R is H or —CH$_3$.

In many embodiments, Z is A$^3$, —(CH$_2$)$_{1-3}$—CO$_2$R$^8$, —(CH$_2$)$_{1-3}$—C(O)NR$^6$R$^7$, —(CH$_2$)$_{1-3}$—SO$_2$NR$^6$R$^7$, —CO$_2$R$^8$, —C(O)NR$^6$R$^7$, —SO$_2$NR$^6$R$^7$, or —(CH$_2$)$_{1-3}$-HET(2), wherein HET(2) is optionally substituted with 1-3 substituents which are independently —C$_{1-3}$alkyl optionally substituted with 1-5 halogens, —OC$_{1-3}$alkyl optionally substituted with 1-5 halogens, halogen or NR$^6$R$^7$.

In many embodiments, Z is A$^3$, —CH$_2$CH$_2$CO$_2$R$^8$, —CH$_2$CH$_2$C(O)NR$^6$R$^7$, —CH$_2$CH$_2$SO$_2$NR$^6$R$^7$, or —CH$_2$CH$_2$-HET(2), wherein HET(2) is optionally substituted with 1-2 substituent groups which are each independently CH$_3$, CF$_3$, —OCH$_3$, —OCF$_3$, halogen, or NR$^6$R$^7$.

In many embodiments, Z is A$^3$, —CH$_2$CH$_2$CO$_2$R$^8$, —CH$_2$CH$_2$-(5-oxo-4,5-dihydro-1,3,4-oxadiazol-2-yl), or —CH$_2$CH$_2$-(5-amino-1,3,4-oxadiazol-2-yl). In many embodiments, each HET(1) is a 5- or 6-membered heterocyclic ring having 1-3 heteroatom groups which are each independently —N—, —NH—, —S—, or —O—, optionally having one group —C(=O)—, and optionally having 1-3 double bonds;

In many embodiments, each HET(1) is a 5- or 6-membered heteroaromatic ring having 1-4 heteroatom groups which are each independently N, NH, S or O;

In many embodiments, HET(2) is a 5-membered heterocyclic ring having 1-3 heteroatom groups which are each independently N, NH, O, or S, optionally having one group —C(=O)—, and optionally having 1-3 double bonds.

In many embodiments, a is 0, 1, or 2.
In many embodiments, a is 0 or 1.
In many embodiments, a is 0.

In many embodiments, the compounds disclosed above and hereinafter can also be represented by Formula Ia, wherein the dashed line in the ring in Formula Ia is an optional double bond. The substituent groups described above for Formula I can also be used in Formula Ia.

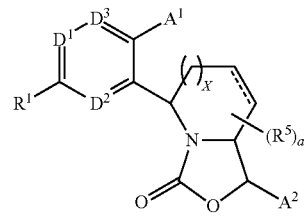

Ia

In many embodiments, the dashed line in the ring in Formula Ia is an optional double bond when x is 0.

In many embodiments, x is 0. In many embodiments, x is 1.

Definitions and Abbreviations

"Ac" is acetyl, which is CH$_3$C(=O)—.

"Alkyl" means saturated carbon chains which may be linear or branched or combinations thereof, unless the carbon chain is defined otherwise. Other groups having the prefix "alk", such as alkoxy and alkanoyl, also may be linear or branched or combinations thereof, unless the carbon chain is defined otherwise. Examples of alkyl groups include methyl, ethyl, propyl, isopropyl, n-butyl, sec-butyl, tert-butyl, pentyl, hexyl, heptyl, octyl, nonyl, and the like.

"Alkylene" groups are alkyl groups that are difunctional rather than monofunctional. For example, methyl is an alkyl group and methylene (—CH$_2$—) is the corresponding alkylene group. Alkyl groups that are shown as difunctional are alkylene groups, even if they are referred to as alkyl groups.

"Alkenyl" means carbon chains which contain at least one carbon-carbon double bond, and which may be linear or branched or combinations thereof. Examples of alkenyl include vinyl, allyl, isopropenyl, pentenyl, hexenyl, heptenyl, 1-propenyl, 2-butenyl, 2-methyl-2-butenyl, and the like.

"Alkynyl" means carbon chains which contain at least one carbon-carbon triple bond, and which may be linear or branched or combinations thereof. Examples of alkynyl include ethynyl, propargyl, 3-methyl-1-pentynyl, 2-heptynyl and the like.

"Cycloalkyl" means a saturated carbocyclic ring having from 3 to 8 carbon atoms, unless otherwise stated. The term also includes a cycloalkyl ring fused to an aryl group. Examples of cycloalkyl include cyclopropyl, cyclopentyl, cyclohexyl, cycloheptyl, and the like. "Cycloalkenyl" means a non-aromatic carbocyclic ring having one or more double binds.

"Aryl" when used to describe a substituent or group in a structure means a monocyclic or bicyclic compound in which the rings are aromatic and which contain only carbon ring atoms. The term "aryl" can also refer to an aryl group that is fused to a cycloalkyl or heterocycle. Preferred "aryls" are phenyl and naphthyl. Phenyl is generally the most preferred aryl group.

"Heterocycle" or "heterocyclic" means a fully or partially saturated or aromatic cyclic compound containing 1 or more heteroatom groups which may be one or more of N, S, O, S(O), S(O)$_2$, or (N)R, and may have one or more double bonds, where R is H or a substituent group. In general, when heterocycles are defined herein, the definition will include the number of ring members, the number of double bonds (if any), and the specific heteroatoms. The heterocycles in some cases will be aromatic, depending on the number of double bonds (e.g. 6-membered ring with 3 double bonds). S(O), S(O)$_2$, and N(R) are referred to as heteroatom groups, and each heteroatom group is counted as one ring member, as is also the case for N, S, and O.

"Benzoheterocycle" represents a phenyl ring fused to a heterocyclic ring. Examples include indole, benzofuran, 2,3-dihydrobenzofuran and quinoline.

"Boc" is tert-butoxycarbonyl.
"n-BuLi" is n-butyl lithium.
"Celite®" is a trade name for diatomaceous earth.
"DBU" is 1,8-diazabicyclo[5.4.0]undec-7-ene.
"D-Epoxone" is a commercial epoxidation catalyst.
"DIPEA" and "DIEA" are N,N-diisopropylethylamine.
"DCM" is dichloromethane.
"DIBAL-H" is diisobutylaluminum hydride.
"DMF" is N,N-dimethylformamide.
"DMAP" is 4-dimethylaminopyridine.
"DMSO" is dimethyl sulfoxide.
"DOPC" is 1,2-dioleoyl-sn-glycero-3-phosphocholine.
"EDTA" is ethylenediaminetetraacetic acid.
"EtOAc" is ethyl acetate.
"EtOH" is ethanol.
"Halogen" includes fluorine, chlorine, bromine and iodine.
"HPLC" is high pressure liquid chromatography.
"IPA" is isopropyl alcohol.
"LiHMDS" is lithium hexamethyldisilazide.
"Me" represents methyl.
"MeCN" is acetonitrile.
"MeOH" is methanol.
"NMP" is N-methyl-2-pyrrolidone.
"OXONE®" is a commercial persulfate oxidizing agent from DuPont.
"PEG" is poly(ethylene glycol).
"RBF" is a round bottom flask.
"Rochelle's salt" is potassium sodium tartrate.
"RT" is an abbreviation for room temperature.
"SFC" is supercritical fluid chromatography.
"SM" is starting material.
"TEA" is triethylamine.
"TFA" is trifluoroacetic acid.
"THF" is tetrahydrofuran.
"TLC" is thin layer chromatography.

The term "composition," as in pharmaceutical composition, is intended to encompass a product comprising the active ingredient(s) and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of Formula I or Ia and a pharmaceutically acceptable carrier.

The substituent "tetrazole" means a 2H-tetrazol-5-yl substituent group and tautomers thereof.

Optical Isomers—Diastereomers—Geometric Isomers—Tautomers

The compounds disclosed herein generally have at least two asymmetric centers, and can thus occur as pure stereoisomers and as mixtures of stereoisomers, including racemates, racemic mixtures, single enantiomers, mixtures of enantiomers, diastereomeric mixtures and individual diastereomers. Different stereoisomers having the same 2-dimensional chemical structure may have different levels of activity with respect to CETP inhibition, so that some stereoisomers may have higher activity than others. The compounds that are potent inhibitors of CETP may have utility in patients for raising HDL-C, lowering LDL-C, treating dyslipidemia, and for preventing, treating or delaying the onset of conditions that are related to atherosclerosis. Stereoisomers that have little or no activity may have utility as research tools for better understanding CETP inhibition. All stereoisomers of the claimed compounds thus have utility. The compounds of Formula I or Ia may also occur as atropisomers (rotamers) due to hindered rotation, which may be observable by NMR spectroscopy, and in some cases may be stable enough with respect to conversion by bond rotation to other atropisomers that they can be isolated and assayed.

Salts

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, triethanolamine, trimethylamine, tripropylamine, tromethamine, and the like.

When the compound of Formula I or Ia is basic, salts may be prepared from pharmaceutically acceptable non-toxic acids, including inorganic and organic acids. Such acids include acetic, adipic, ascorbic, benzenesulfonic, benzoic, camphorsulfonic, citric, diethylacetic, ethanesulfonic, formic, fumaric, gluconic, glutamic, hydrobromic, hydrochloric, isethionic, isonicotinic, lactic, maleic, malic, malonic, mandelic, methanesulfonic, mucic, naphthalenedisulfonic, nitric, oxalic, pamoic, pantothenic, phenylpropionic, phosphoric, pimelic, pivalic, propionic, salicylic, succinic, sulfuric, sulfaminic, tartaric, p-toluenesulfonic acid, trifluoroacetic and the like. Particularly preferred are citric, hydrobromic, hydrochloric, maleic, phosphoric, sulfuric, and tartaric acids.

It will be understood that, as used herein, references to the compounds of Formula I and Ia and to the examples are meant to also include the pharmaceutically acceptable salts and prodrugs, where such salts and prodrugs are possible.

Prodrugs

Prodrugs, which are compounds that are converted to the compound of Formula I or Ia as they are being administered to a patient or after they have been administered to a patient, are also compounds of formula I or Ia in the sense that they provide the claimed pharmaceutically active drug moiety to the patient.

Isotopes

In the compounds of Formula I and Formula Ia, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I and Formula Ia. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I and Ia can be prepared without undue experimentation by conventional techniques well known to those skilled in the art or by processes analogous to those described in the Schemes and Examples herein using appropriate isotopically-enriched reagents and/or intermediates.

Utilities

The compounds disclosed herein, including pharmaceutically acceptable salts thereof, are potent inhibitors of CETP. The compounds may therefore be useful in treating mammalian patients, preferably human patients, having diseases and conditions that are treated by inhibition of CETP.

One aspect of the present invention provides a method for treating or reducing the risk of developing a disease or condition that may be treated or prevented by inhibition of CETP by administering a therapeutically effective amount of the compound of Formula I or Ia to a patient in need of treatment. The patient is a human or mammal, but is most often a human. A "therapeutically effective amount" is the amount of compound that is effective in obtaining a desired clinical outcome in the treatment of a specific disease.

Diseases or conditions that may be treated with the compounds of Formula I or Formula Ia, or which the patient may have a reduced risk of developing as a result of being treated with the compounds of Formula I or Formula Ia, include: atherosclerosis, peripheral vascular disease, dyslipidemia, hyperbetalipoproteinemia, hypoalphalipoproteinemia, hypercholesterolemia, hypertriglyceridemia, familial-hypercholesterolemia, cardiovascular disorders, angina, ischemia, cardiac ischemia, stroke, myocardial infarction, reperfusion injury, angioplastic restenosis, hypertension, vascular complications of diabetes, obesity, endotoxemia, and metabolic syndrome. There are reports in the scientific literature that suggest that inhibition of CETP may have utility in preventing or slowing the development of Alzheimer's disease. The compounds of Formula I and Ia may therefore have utility in preventing or delaying the progression of Alzheimer's disease or other neurodegenerative diseases.

The compounds disclosed herein are particularly effective in raising HDL-C and/or increasing the ratio of HDL-C to LDL-C. The compounds may also be effective in reducing LDL-C, and may be effective in treating dyslipidemia. These changes in HDL-C and LDL-C may be beneficial in treating atherosclerosis, reducing or delaying the development of atherosclerosis, reducing the risk of developing atherosclerosis, or preventing atherosclerosis. The compounds disclosed herein may thus be beneficial in treating atherosclerosis, reducing or delaying the development of atherosclerosis, reducing the risk of developing atherosclerosis, or preventing atherosclerosis.

Likely indications for atherosclerosis and dyslipidemia using the compounds described herein are written below, where the drug product is titled "CETP inhibitor:"

Atherosclerosis.

In patients at high risk of cardiovascular events because of existing coronary, cerebrovascular, or peripheral vascular disease, CETP inhibitor co-administered with an HMG-CoA reductase inhibitor is indicated to reduce the risk of coronary mortality, myocardial infarction, coronary revascularization procedures, ischemic stroke, and cardiovascular death.

Dyslipidemia.

CETP inhibitor co-administered with a statin is indicated to reduce elevated LDL-C, apolipoprotein B (ApoB), lipoprotein a (Lp(a)), non-HDL-C, and total cholesterol; and increase HDL-C and apolipoprotein A-1 (Apo A-1) in patients with mixed or primary dyslipidemia.

Administration and Dose Ranges

Any suitable route of administration may be employed for providing a mammal, especially a human, with an effective dose of the compounds described herein. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably the compound of Formula I or Ia is administered orally.

When treating the diseases for which the compound of Formula I or Ia is indicated, generally satisfactory results are expected when the compound of Formula I or Ia is administered at a daily dosage of from about 0.1 milligram to about 1000 milligram in one dose daily or divided into more than one dose per day.

Oral administration will usually be carried out using tablets. Examples of doses in tablets include 0.1 mg, 0.5 mg, 1 mg, 2 mg, 5 mg, 10 mg, 25 mg, 50 mg, 60 mg, 70 mg, 80 mg, 90 mg, 100 mg, 110 mg, 120 mg, 130 mg, 140 mg, 150 mg, 160 mg, 170 mg, 180 mg, 190 mg, 200 mg, 210 mg, 220 mg, 230 mg, 240 mg, 250 mg, 275 mg, 300 mg, 350 mg, 400 mg, 450 mg, 500 mg, and 1000 mg. Other oral forms can also have the same dosages (e.g. capsules). A preferred dose is likely in the range of 50-200 mg.

Pharmaceutical Compositions

Another aspect of the present invention provides pharmaceutical compositions which comprise the compound of Formula I or Ia and a pharmaceutically acceptable carrier. The pharmaceutical compositions of the present invention comprise the compound of Formula I or Ia or a pharmaceutically acceptable salt as an active ingredient, as well as a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids. A pharmaceutical composition may also comprise a prodrug, or a pharmaceutically acceptable salt thereof, if a prodrug is administered. A pharmaceutical composition may also consist essentially of the compound of Formula I or Ia, or a pharmaceutically acceptable salt of the compound, and a pharmaceutically acceptable carrier, without other therapeutic ingredients.

Pharmaceutical compositions may be formulated to be suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compound of Formula I or Ia can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compound can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

The compound of formula I or Ia may also be administered parenterally. Solutions or suspensions of the compound can be prepared in water suitably mixed with a surfactant such as hydroxypropylcellulose. Dispersions can also be prepared in glycerol, liquid polyethylene glycols and mixtures thereof in oils. Under ordinary conditions of storage and use, these preparations may contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

Combination Therapy

The compound of Formula I or Ia, including pharmaceutically acceptable salts thereof, may be used in pharmaceutical combinations with other drugs that may also be useful in the treatment or amelioration of the diseases or conditions for which the compound of Formula I or Ia is useful. Such other drugs may be administered, by a route and in an amount commonly used therefor, contemporaneously or sequentially with the compound of Formula I or Ia. When the compound of Formula I or Ia is used contemporaneously with one or more other drugs, a pharmaceutical composition in unit dosage form containing such other drugs and the compound of Formula I or Ia is preferred. However, the combination therapy also includes therapies in which the compound of Formula I or Ia and one or more other drugs are administered concomitantly, on the same or different schedules.

When oral formulations are used, the drugs may be combined into a single combination tablet or other oral dosage form, or the drugs may be packaged together as separate tablets or other oral dosage forms. It is also contemplated that when used in combination with one or more other active ingredients, the compound of formula I or Ia and the other active ingredients may be used in lower doses than when each is used singly. Accordingly, the pharmaceutical compositions of the compound of formula I or Ia include those that contain one or more other active ingredients, in addition to the compound of Formula I or Ia.

The compound of Formula I or Ia will likely be approved initially for coadministration with a statin, which could be administered in the form of a fixed dose combination of the compound of formula I or Ia and a statin. Additional drugs may also be administered in combination with the compound of Formula I or Ia and the statin, either by coadministration or in a fixed dose combination. The compound of formula I or Ia and the drugs that are administered with it may be administered as pharmaceutically acceptable salts, as prodrugs, or otherwise formulated for immediate release, extended release, or controlled release, as necessary.

Examples of statins that may be administered in combination with the compound of Formula I or Ia include, but are not limited to, (i) simvastatin and lovastatin which are marketed as ZOCOR® and MEVACOR® in lactone prodrug form and function as inhibitors after administration, and (ii) dihydroxy open ring acid HMG-CoA reductase inhibitors such as atorvastatin (particularly the calcium salt sold in LIPITOR®), rosuvastatin (particularly the calcium salt sold in CRESTOR®), pravastatin (particularly the sodium salt sold in PRAVACHOL®), fluvastatin (particularly the sodium salt sold in LESCOL®), and pitavastatin (particularly the calcium salt sold in LIVALO®), and (iii) other statins that may yet be developed. Preferred statins for combination therapy include atorvastatin, rosuvastatin, and simvasatin, as described above.

Cholesterol absorption inhibitors, and particularly ezetimibe (ZETIA®), as well as other cholesterol asorption inhibitors, such as stanol esters, beta-sitosterol, sterol glycosides such as tiqueside, and other azetidinones, may be administered with the compound of Formula I or Ia, generally with a statin, as described above. The preferred cholesterol absorbtion inhibitor is ezetimibe. Combinations of the compound of formula I or Ia with a statin and a cholesterol inhibitor, such as ezetimibe, are also contemplated. Preferred 3-component combinations include combinations of the compound of formula I or Ia with simvastatin, atorvastatin, or rosuvastatin in combination with ezetimibe, where the statins may be salt forms or prodrugs as described above. The combination of simvastatin with ezetimibe is currently marketed as VYTORIN®.

Other cholesterol reducing drugs that may be coadministered with the compound of formula I or Ia in addition to HMG-CoA reductase inhibitors (statins) and cholesterol absorption inhibitors include (i) bile acid sequestrants, as for example cholestyramine, colestipol, dialkylaminoalkyl derivatives of a cross-linked dextran, Colestid®, and LoCholest®, (ii) niacin and related compounds, such as nicotinyl alcohol, nicotinamide, and nicotinic acid or a salt thereof, in an immediate release or extended release form, which may optionally be in the forme of a combination with a DP-1 antagonist, such as laropiprant (TREDAPTIVE®); (iii) PPARa agonists, such as gemfibrozil and fenofibric acid derivatives (fibrates), including clofibrate, fenofibrate, bezafibrate, ciprofibrate, and etofibrate, (iv) acyl CoA:cholesterol acyltransferase (ACAT) inhibitors, such as avasimibe and melinamide, and including selective ACAT-1 and ACAT-2 inhibitors and dual inhibitors, (v) phenolic anti-oxidants, such as probucol, (vi) microsomal triglyceride transfer protein (MTP)/ApoB secretion inhibitors, (vii) anti-oxidant vitamins, such as vitamins C and E and beta carotene, (viii) thyromimetics, (ix) LDL (low density lipoprotein) receptor inducers, (x) platelet aggregation inhibitors, for example glycoprotein IIb/IIIa fibrinogen receptor antagonists and aspirin, (xi) vitamin B12 (also known as cyanocobalamin), (xii) folic acid or a pharmaceutically acceptable salt or ester thereof, such as the sodium salt and the methylglucamine salt, (xiii) FXR and LXR ligands, including both inhibitors and agonists, (xiv) agents that enhance $ABCA^1$ gene expression, (xv) ileal bile acid transporters, and (xvi) niacin receptor agonists (e.g. acipimox and acifran) and partial agonists.

Finally the compound of formula I or Ia can be combined with compounds that are useful for treating other diseases, such as diabetes, hypertension and obesity, as well as other anti-atherosclerotic compounds. Such combinations may be used to treat one or more of such diseases as diabetes, obesity, atherosclerosis, and dyslipidemia, or more than one of the diseases associated with metabolic syndrome. The combinations may exhibit synergistic activity in treating these diseases, allowing for the possibility of administering reduced doses of active ingredients, such as doses that otherwise might be sub-therapeutic.

Examples of other active ingredients that may be administered in combination with a compound of formula I or Ia include, but are not limited to, compounds that are primarily anti-diabetic compounds, including:

(a) PPAR gamma agonists and partial agonists, including glitazones and non-glitazones (e.g. pioglitazone, englitazone, MCC-555, rosiglitazone, balaglitazone, netoglitazone, T-131, LY-300512, LY-818, and compounds described in WO 02/060388, WO 02/08188, WO 2004/019869, WO 2004/020409, WO 2004/020408, and WO2004/066963);

(b) biguanides such as metformin, phenformin, and pharmaceutically acceptable salts thereof, in particular metformin hydrochloride and extended release formulations thereof, such as Glumetza™, Fortamet™, and GlucophageXR™;

(c) protein tyrosine phosphatase-1B (PTP-1B) inhibitors, such as ISIS-113715 and TTP814;

(d) dipeptidyl peptidase IV (DP-IV) inhibitors, including sitagliptin, vildagliptin, saxagliptin, alogliptin, linagliptin, dutogliptin, teneligliptin, MK-3102, and gemigliptin;

(e) insulin or insulin mimetics, such as for example insulin lispro, insulin glargine, insulin detemir, insulin glulisine, insulin degludec, SBS1000, insulin zinc suspension, and oral and inhalable formulations of insulin and insulin analogs;

(f) sulfonylureas, such as tolbutamide, glipizide, glimepiride, acetohexamide, chlorpropamide, glibenclamide, and related materials;

(g) α-glucosidase inhibitors (such as acarbose, adiposine; camiglibose; emiglitate; miglitol; voglibose; pradimicin-Q; and salbostatin);

(h) PPARα/γ dual agonists, such as muraglitazar, tesaglitazar, farglitazar, and naveglitazar;

(i) PPARδ agonists such as GW501516 and those disclosed in WO97/28149;

(j) glucagon receptor antagonists;

(k) GLP-1; GLP-1 derivatives; GLP-1 mimetics, GLP-1 analogs, and GLP-1 receptor agonists, such as exendins, e.g. exenatide (BYETTA), dulaglutide, semaglutide, albiglutide, liraglutide, lixisenatide, and taspoglutide, including intranasal, tranxsdermal, and once weekly formulations thereof, and oxyntomodulin analogs and derivatives, and non-peptidyl GLP-1 receptor agonists;

(l) GIP-1;

(m) amylin and amylin analogs (e.g. pramlintide);

(n) Non-sulfonylurea insulin secretagogues, such as the meglitinides (e.g. glimepiride, mitiglinide, meglitinide, nateglinide, and rapeglinide); and (o) leptin and leptin derivatives and agonists.

Preferred combinations with antidiabetic compounds include combinations of the compounds disclosed herein with DP-IV inhibitors (sitagliptin, vildagliptin, saxagliptin, alogliptin, linagliptin, dutogliptin, teneligliptin, omarigliptin, and gemigliptin), combinations with biguanides, and combinations with both a DP-IV inhibitor and a biguanide. The preferred DP-IV inhibitor is sitagliptin, and the preferred biguanide is metformin in the formulations and salt forms described above.

Other active ingredients that may be used in combination with the compound of formula I or Ia include antiobesity compounds, including 5-HT(serotonin) inhibitors, neuropeptide Y5 (NPY5) inhibitors, melanocortin 4 receptor (Mc4r) agonists, cannabinoid receptor 1 (CB-1) antagonists/inverse agonists, and $β_3$ adrenergic receptor agonists. These are listed in more detail later in this section.

These other active ingredients also include active ingredients that are used to treat inflammatory conditions, such as aspirin, non-steroidal anti-inflammatory drugs, glucocorticoids, azulfidine, and selective cyclooxygenase-2 (COX-2) inhibitors, including etoricoxib, celecoxib, rofecoxib, and Bextra.

Antihypertensive compounds may also be used advantageously in combination therapy with the compound of formula I or Ia. Examples of antihypertensive compounds that may be used with the compound of formula I or Ia include thiazide-like diuretics, e.g., hydrochlorothiazide (HCTZ or HCT); angiotensin converting enzyme inhibitors (e.g, alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril); dual inhibitors of angiotensin converting enzyme (ACE) and neutral endopeptidase (NEP) such as omapatrilat, sampatrilat and fasidotril; angiotensin II receptor antagonists, also known as angiotensin receptor blockers or ARBs, which may be in free-base, free-acid, salt or prodrug form, such as azilsartan, e.g., azilsartan medoxomil potassium (EDARBI®), candesartan, e.g., candesartan cilexetil (ATACAND®), eprosartan, e.g., eprosartan mesylate (TEVETAN®), irbesartan (AVAPRO®), losartan, e.g., losartan potassium (COZAAR®), olmesartan, e.g, olmesartan medoximil (BENICAR®), telmisartan (MICARDIS®), valsartan (DIOVAN®), and any of these drugs used in combination with a thiazide-like diuretic such as hydrochlorothiazide (e.g., HYZAAR®, DIOVANHCT®, ATACAND HCT®), etc.); potassium sparing diuretics such as amiloride HCl, spironolactone, eplerenone, triamterene, each with or without HCTZ; carbonic anhydrase inhibitors, such as acetazolamide; neutral endopeptidase inhibitors (e.g., thiorphan and phosphoramidon); aldosterone antagonists; aldosterone synthase inhibitors; renin inhibitors (e.g. urea derivatives of di- and tri-peptides (See U.S. Pat. No. 5,116,835), amino acids and derivatives (U.S. Pat. Nos. 5,095,119 and 5,104,869), amino acid chains linked by non-peptidic bonds (U.S. Pat. No. 5,114,937), di- and tri-peptide derivatives (U.S. Pat. No. 5,106,835), peptidyl amino diols (U.S. Pat. Nos. 5,063,208 and 4,845,079) and peptidyl beta-aminoacyl aminodiol carbamates (U.S. Pat. No. 5,089,471); also, a variety of other peptide analogs as disclosed in the following U.S. Pat. Nos. 5,071,837; 5,064,965; 5,063,207; 5,036,054; 5,036,053; 5,034,512 and 4,894,437, and small molecule renin inhibitors (including diol sulfonamides and sulfinyls (U.S. Pat. No. 5,098,924), N-morpholino derivatives (U.S. Pat. No. 5,055,466), N-heterocyclic alcohols (U.S. Pat. No. 4,885,292) and pyrolimidazolones (U.S. Pat. No. 5,075,451); also, pepstatin derivatives (U.S. Pat. No. 4,980,283) and fluoro- and chloro- derivatives of statone-containing peptides (U.S. Pat. No. 5,066,643); enalkrein; RO 42-5892; A 65317; CP 80794; ES 1005; ES 8891; SQ 34017; aliskiren (2(S),4(S),5(S),7(S)—N-(2-carbamoyl-2-methylpropyl)-5-amino-4-hydroxy-2,7-diisopropyl-8-[4-methoxy-3-(3-methoxypropoxy)-phenyl]-octanamid hemifumarate) SPP600, SPP630 and SPP635); endothelin receptor antagonists; vasodilators (e.g. nitroprusside); calcium channel blockers (e.g., amlodipine, nifedipine, verapamil, diltiazem, felodipine, gallopamil, niludipine, nimodipine, nicardipine, bepridil, nisoldipine); potassium channel activators (e.g., nicorandil, pinacidil, cromakalim, minoxidil, aprilkalim, loprazolam); sympatholitics; beta-adrenergic blocking drugs (e.g., acebutolol, atenolol, betaxolol, bisoprolol, carvedilol, metoprolol, metoprolol tartate, nadolol, propranolol, sotalol, timolol); alpha adrenergic blocking drugs (e.g., doxazocin, prazocin or alpha methyldopa); central alpha adrenergic agonists; peripheral vasodilators (e.g. hydralazine); and nitrates or nitric oxide donating compounds, e.g. isosorbide mononitrate.

Preferred antihypertensives that may be used in combination with the CETP inhibitors disclosed herein include one or more of an angiotensin II antagonist (losartan), an ACE inhibitor (enalapril or captopril), and hydrochlorothiazide.

Anti-obesity compounds may be administered in combination with the compounds of Formula I or Formula Ia, including: (1) growth hormone secretagogues and growth hormone secretagogue receptor agonists/antagonists, such as NN703 and hexarelin; (2) protein tyrosine phosphatase-1B (PTP-1B) inhibitors; (3) cannabinoid receptor ligands, such as cannabinoid $CB_1$ receptor antagonists or inverse agonists, such as rimonabant (Sanofi Synthelabo), AMT-251, and SR-14778 and SR 141716A (Sanofi Synthelabo), SLV-319 (Solvay), BAY 65-2520 (Bayer); (4) anti-obesity serotonergic agents, such as fenfluramine, dexfenfluramine, phentermine, and sibutramine; (5) β3-adrenoreceptor agonists, such as AD9677/TAK677 (Dainippon/Takeda), CL-316,243, SB 418790, BRL-37344, L-796568, BMS-196085, BRL-35135A, CGP12177A, BTA-243, Trecadrine, Zeneca D7114, and SR 59119A; (6) pancreatic lipase inhibitors, such as orlistat (Xenical®), Triton WR1339, RHC80267, lipstatin, tetrahydrolipstatin, teasaponin, and diethylumbelliferyl phosphate; (7) neuropeptide Y1 antagonists, such as BIBP3226, J-115814, BIBO 3304, LY-357897, CP-671906, and GI-264879A; (8) neuropeptide Y5 antagonists, such as GW-569180A, GW-594884A, GW-587081X, GW-548118X, FR226928, FR 240662, FR252384, 1229U91, GI-264879A, CGP71683A, LY-377897, PD-160170, SR-120562A, SR-120819A and JCF-104; (9) melanin-concentrating hormone (MCH) receptor antagonists; (10) melanin-concentrating hormone 1 receptor (MCH1R) antagonists, such as T-226296 (Takeda); (11) melanin-concentrating hormone 2 receptor (MCH2R) agonist/antagonists; (12) orexin-1 receptor antagonists, such as SB-334867-A; (13) melanocortin agonists, such as Melanotan II; (14) other Mc4r (melanocortin 4 receptor) agonists, such as CHIR86036 (Chiron), ME-10142, and ME-10145 (Melacure), CHIR86036 (Chiron); PT-141, and PT-14 (Palatin); (15) 5HT-2 agonists; (16) 5HT2C (serotonin receptor 2C) agonists, such as BVT933, DPCA37215, WAY161503, and R-1065; (17) galanin antagonists; (18) CCK agonists; (19) CCK-A (cholecystokinin-A) agonists, such as AR-R 15849, GI 181771, JMV-180, A-71378, A-71623 and SR146131; (20) GLP-1 agonists; (21) corticotropin-releasing hormone agonists; (22) histamine receptor-3 (H3) modulators; (23) histamine receptor-3 (H3) antagonists/inverse agonists, such as hioperamide, 3-(1H-imidazol-4-yl)propyl N-(4-pentenyl)carbamate, clobenpropit, iodophenpropit, imoproxifan, and GT2394 (Gliatech); (24) β-hydroxy steroid dehydrogenase-1 inhibitors (11β-HSD-1 inhibitors), such as BVT 3498 and, BVT 2733, (2S) PDE (phosphodiesterase) inhibitors, such as theophylline, pentoxifylline, zaprinast, sildenafil, aminone, milrinone, cilostamide, rolipram, and cilomilast; (26) phosphodiesterase-3B (PDE3B) inhibitors; (27) NE (norepinephrine) transport inhibitors, such as GW 320659, despiramine, talsupram, and nomifensine; (28) ghrelin receptor antagonists; (29) leptin, including recombinant human leptin (PEG-OB, Hoffman La Roche) and recombinant methionyl human leptin (Amgen); (30) leptin derivatives; (31) BRS3 (bombesin receptor subtype 3) agonists such as [D-Phe6,beta-Ala11,Phe13,Nle14]Bn(6-14) and [D-Phe6,Phe13]Bn(6-13)propylamide; (32) CNTF (Ciliary neurotrophic factors), such as GI-181771 (Glaxo-SmithKline), SR146131 (Sanofi Synthelabo), butabindide, PD170,292, and PD 149164 (Pfizer); (33) CNTF derivatives, such as axokine (Regeneron); (34) monoamine reuptake inhibitors, such as sibutramine; (35) UCP-1 (uncoupling protein-1, 2, or 3) activators, such as phytanic acid, 4-[(E)-2-(5,6,7,8-tetrahydro-5,5,8,8-tetramethyl-2-napthalenyl)-1-propenyl]benzoic acid (TTNPB), and retinoic acid; (36) thyroid hormone β agonists, such as KB-2611 (KaroBioBMS); (37) FAS (fatty acid synthase) inhibitors, such as Cerulenin and C75; (38) DGAT1 (diacylglycerol acyltransferase 1) inhibitors; (39) DGAT2 (diacylglycerol acyltransferase 2) inhibitors; (40) ACC2 (acetyl-CoA carboxylase-2) inhibitors; (41) glucocorticoid antagonists; (42) acyl-estrogens, such as oleoyl-estrone; (43) dicarboxylate transporter inhibitors; (44) peptide YY, PYY 3-36, peptide YY analogs, derivatives, and fragments such as BIM-43073D, BIM-43004C, (4S) Neuropeptide Y2 (NPY2) receptor agonists such NPY3-36, N acetyl [Leu(28,31)] NPY 24-36, TASP-V, and cyclo-(28/32)-Ac-[Lys28-Glu32]-(25-36)-pNPY; (46) Neuropeptide Y4 (NPY4) agonists such as pancreatic peptide (PP); (47) Neuropeptide Y1 (NPY1) antagonists such as BIBP3226, J-115814, BIBO 3304, LY-357897, CP-671906, and GI-264879A; (48) Opioid antagonists, such as nalmefene (Revex®), 3-methoxynaltrexone, naloxone, and naltrexone; (49) glucose transporter inhibitors; (50) phosphate transporter inhibitors; (51) 5-HT (serotonin) inhibitors; (52) beta-blockers; (53) Neurokinin-1 receptor antagonists (NK-1 antagonists); (54) clobenzorex; (55) cloforex; (56) clominorex; (57) clortermine; (58) cyclexedrine; (59) dextroamphetamine; (60) diphemethoxidine, (61) N-ethylamphetamine; (62) fenbutrazate; (63) fenisorex; (64) fenproporex; (65) fludorex; (66) fluminorex; (67) furfurylmethylamphetamine; (68) levamfetamine; (69) levophacetoperane; (70) mefenorex; (71) metamfepramone; (72) methamphetamine; (73) norpseudoephedrine; (74) pentorex; (75) phendimetrazine; (76) phenmetrazine; (77) picilorex; (78) phytopharm 57; (79) zonisamide, (80) a minorex; (81) amphechloral; (82) amphetamine; (83) benzphetamine; and (84) chlorphentermine.

The combination therapies described above which use the compounds of Formula I or Formula Ia may also be useful in the treatment of the metabolic syndrome. According to one widely used definition, a patient having metabolic syndrome is characterized as having three or more symptoms selected from the following group of five symptoms: (1) abdominal obesity; (2) hypertriglyceridemia; (3) low high-density lipoprotein cholesterol (HDL); (4) high blood pressure; and (5) elevated fasting glucose, which may be in the range characteristic of Type 2 diabetes if the patient is also diabetic. Each of these symptoms is defined clinically in the Third Report of the National Cholesterol Education Program Expert Panel on Detection, Evaluation and Treatment of High Blood Cholesterol in Adults (Adult Treatment Panel III, or ATP III), National Institutes of Health, 2001, NIH Publication No. 01-3670. Patients with metabolic syndrome have an increased risk of developing the macrovascular and microvascular complications that are listed above, including atherosclerosis and coronary heart disease. The combinations described above may ameliorate more than one symptom of metabolic syndrome concurrently (e.g. two symptoms, three symptoms, four symptoms, or all five of the symptoms).

Assays

Protocol: Scintillation Proximity Assay (SPA) for CETP Activity

First, low density lipoprotein (LDL) (Meridian) was biotinylated by incubating LDL with biotin for 1 hour on ice, after which it was dialyzed to remove free biotin. Then compounds at varying concentrations were incubated with 15 nM CETP (reagent production group, In Vitro Pharmacology, MRL Rahway) and 50 ug/ml of the biotinylated LDL in 50 mM HEPES, 150 mM NaCl, pH 7.4, for 1 hour at 37° C. The reaction was started by adding $^3$H-cholesterol ester high density lipoprotein (HDL) (American Radiochemicals Corp) at a concentration of ~0.6 nM. The reaction proceeded for 2 hours at 37° C., after which time it was quenched by the addition of 12% acetic acid. PVT streptavadin-coated scintillation proximity beads, which had been brought to room temperature, were then added at a concentration of 4 mg/ml. The assay was then mixed and counted after one half hour in a Microbeta plate reader.

In Vitro Radioactive Assays of CETP-Catalyzed CE and TG Transfer (RTA Assay)

Reagents and sources are: [3H] cholesteryl oleate (GE #TRK.886), [3H] Triolein (Perkin-Elmer NET-431), Butylated hydroxyl toluene (Aldrich, #D4740-4), DOPC (Sigma, #P6354), Sodium Bromide (Fisher scientific #S255-500), PEG 8000 (Fisher, #BP233-1), and human HDL (Intracel Corp #RP-036).

An in vitro assay for determining $IC_{50}$'s to identify compounds that inhibit CETP transfer activity is performed based on a modification of a published method (Morton and Zilversmit, (1981) A plasma inhibitor of triglyceride and cholesteryl ester transfer activities, J. Biol. Chem. 256(23), 11992-11995). The ability of inhibitors to alter CETP activity is performed using two different assays: one using recombinant CETP and one using an endogenous plasma source of CETP. Both assays measure the transfer of [3H] cholesteryl oleate or [3H] triolein from exogenous LDL to HDL.

Radiolabeled donor particles are generated by first combining 100 µl of 200 µM butylated hydroxyl toluene in $CHCl_3$, 216 µL of 21.57 mM DOPC in EtOH, and either 500 µCi [3H]-triolein (Perkin Elmer #NET-431) or 500 µCi [3H]-cholesteryl oleate (GE #TRK886) in a glass tube. Reagents are mixed, dried under nitrogen, and then resuspended in 2 mL of 50 mM Tris, 27 µM EDTA at pH 7.4. After a brief vortex, the solution is sonicated until clear and mixed with 20 mL of fresh human serum. The mixture is incubated overnight at 37° C. The [3H] labeled LDL substrate is separated at 1.063 g/ml density by sequential ultracentrifugal flotation in NaBr according to the method of Havel, Eder, et al., 1955, and Chapman, Goldstein, et al., 1981. Once isolated the particles are dialyzed 3× in CETP buffer (50 mM Tris, pH 7.4, 100 mM NaCl, 1 mM EDTA). Human HDL is purchased from Intracel and used as the acceptor particles.

Transfer assays are performed in a 96-well v-bottom polypropylene plate. For the RTA using recombinant CETP (2% RTA), an assay cocktail is prepared with the final concentrations 128 µg/mL HDL, 20 nM rCETP, 2% human serum, and 1×CETP buffer. 1 µL of each test compound diluted in DMSO is added to 47 µL of assay cocktail per well and incubated at 37° C. for 1 hour. To initiate the transfer reaction, 2 µL radiolabeled LDL is added. After an additional 60 min of incubation at 37° C., the transfer action is terminated by precipitation of LDL with an equal volume of 20% WN PEG 8000. The plates are centrifuged at 2000 rpm for 30 minutes at 4° C. A 40 µL aliquot of the HDL-containing supernatant is transferred to a Packard Optiplate™ with 200 µL of MicroScint™ 20. After mixing, plates are counted by liquid scintillation. Counts present in the supernatant for blanks (wells containing only HDL acceptor, CETP buffer and DMSO) are subtracted from those containing test compounds and used to correct for non-specific transfer.

For the transfer assay using endogenous CETP from serum (95% RTA), the same procedure is used except that human serum is added such that a final concentration of serum of 95% of the total assay volume is achieved, yielding a concentration of approximately 15 nM endogenous CETP in the assay. This is then combined with HDL and CETP buffer and the reaction proceeds as above and is terminated as described.

Comparison of the counts of samples with inhibitors to an uninhibited (DMSO only) positive control yield a percent inhibition. A plot of percent inhibition vs. log of inhibitor concentration, fit to a Sigmoidal 4 parameter equation is used to calculate IC50.

EXAMPLES

The following schemes and examples are provided so that the invention will be more fully appreciated and understood. These examples are illustrative and are not to be construed as limiting the invention in any way. The claims appended hereto define the scope of the invention.

Starting materials are commercially available or are made using known procedures or as shown below. The examples may be synthesized using the general schemes provided below. The data reported for the examples below were obtained using the RTA assay in 95% human serum. The IC50's for the examples using this assay are in the range of about 44-1742 nM. Preferred compounds have an IC50 less than about 500 nM. More preferred compounds have an IC50 less than about 100 nM. When compounds of Formula I or Formula Ia are mentioned herein, such compounds include compounds defined generically by Formula I or Ia and also the specific examples disclosed herein.

Synthetic Schemes

Syntheses of Intermediates

The examples were synthesized according to the general schemes shown below. Synthetic intermediates for making the compounds are made as described below and are illustrated in the following schemes. The various starting materials used in the schemes are commercially available or are readily made by persons skilled in the art.

Scheme A1

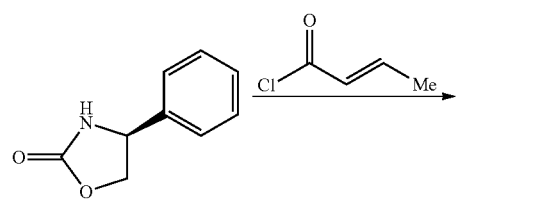

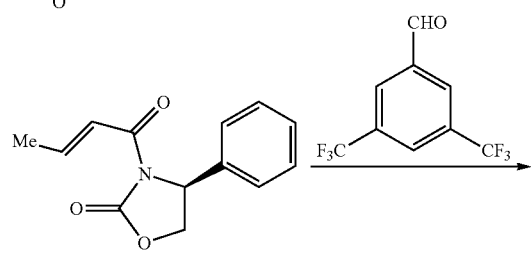

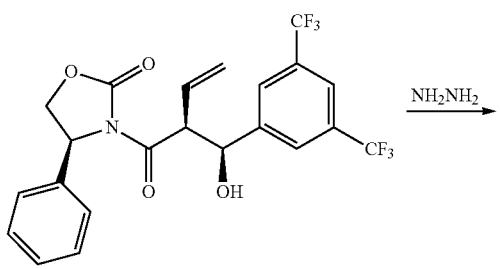

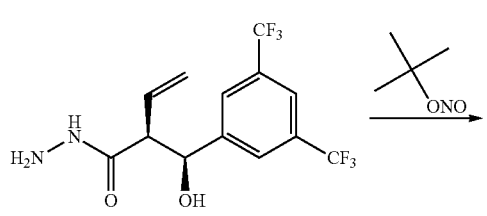

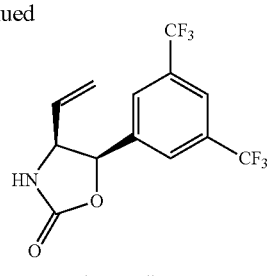

intermediate A

Scheme A2

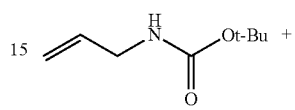

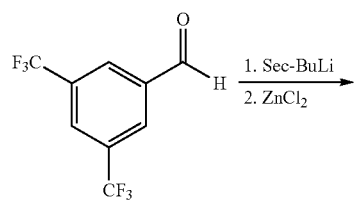

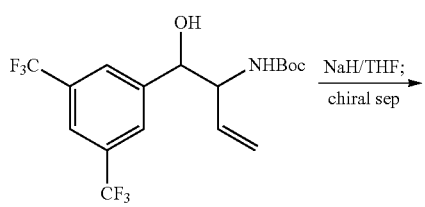

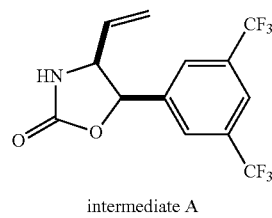

intermediate A

Intermediate A is prepared from a chiral auxiliary-controlled aldol reaction from commercially available starting materials (Scheme A1). Treatment of the aldol product with hydrazine and subsequent diazotization and Curtius rearrangement provides Intermediate A (Wang et al., Tetrahedron, 2009, 65, 6291-6303). Alternatively, Intermediate A can be prepared via treatment of N-Boc-allylamine with sec-butyllithium followed by ZnCl$_2$ to provide a dilithiated reagent that readily reacts with a known aldehyde (Resek, J. E.; Beak, P. Tetrahedron Letters, 1993, 34, 3043) (Scheme A$^2$). Subsequent treatment with sodium hydride results in the synthesis of Intermediate A.

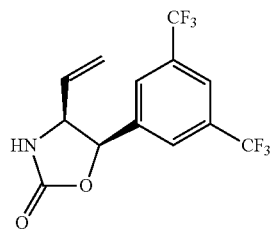 [SMILES: C=C[C@@H]1NC(=O)O[C@@H]1c1cc(C(F)(F)F)cc(C(F)(F)F)c1]

Intermediate A—Scheme A1

(4S,5R)-5-[3,5-bis(trifluoromethyl)phenyl]-4-ethenyl-1,3-oxazolidin-2-one

Step 1: To a stirred solution of (4S)-4-phenyl-1,3-oxazolidin-2-one (12 g, 73.5 mmol) in THF (200 mL) was added n-BuLi (2.5 M, 29.4 mL, 73.5 mmol) dropwise via a syringe at −78° C. The resulting reaction mixture was stirred at −78° C. for 5 minutes before (2E)-but-2-enoyl chloride (8.46 mL, 88.0 mmol) was added dropwise via a syringe. The reaction mixture was allowed to warm to ambient temperature and was quenched by addition of brine (100 mL) and water (100 mL). A mixture of ethyl acetate and hexanes (1:2, 100 mL) was added to partition the mixture and the organics were separated, dried over sodium sulfate, filtered and concentrated. The resultant oil was recrystallized in 5% ethyl acetate in hexanes (after seeding with crystals obtained from earlier batches) to yield (4S)-3-[(2E)-but-2-enoyl]-4-phenyl-1,3-oxazolidin-2-one (15.7 g, 67.9 mmol). $^1$H NMR (500 MHz, CDCl$_3$) δ 7.4 (m, 6H), 5.5 (m, 1H) 4.73 (t, J=8.8 Hz, 1H), 4.30 (m, 1H), 1.97 (dd, J=6.8, 1.5 Hz, 3H).

Step 2: To (4S)-3-[(2E)-but-2-enoyl]-4-phenyl-1,3-oxazolidin-2-one (13.8 g, 59.7 mmol) in DCM (100 mL) was added TiCl$_4$ (1M in DCM, 59.7 mL, 59.7 mmol) at −10° C. The resulting reaction solution was transferred by cannula to a flask containing DIPEA (11.26 mL, 64.5 mmol) and DCM (100 mL) at 10° C. NMP (11.49 mL, 119 mmol) was added via a syringe and the reaction mixture was aged for 1 hour before cooling to −40° C. 3,5-Bis(trifluoromethyl)benzaldehyde (17.3 g, 71.6 mmol) in DCM (25 mL) was added via a syringe and the reaction was allowed to warm to 0° C. over 1.5 hr. The reaction was quenched by addition of acetic acid (15 mL), saturated Rochelle's salt (50 mL) and HCl (1.0 M, 200 mL). The organic was separated and the aqueous was back extracted with DCM (50 mL). The organics were combined, washed with HCl (1.0 M, 100 mL), dried over sodium sulfate, filtered and concentrated. The resultant oil was purified by column chromatography to give (4S)-3-{(2S)-2-[(5)-[3,5-bis(trifluoromethyl)phenyl](hydroxy)methyl]but-3-enoyl}-4-phenyl-1,3-oxazolidin-2-one (20 g, 42.3 mmol) as crystalline solid. $^1$H NMR (500 MHz, CDCl$_3$) δ 7.86 (s, 2H), 7.83 (s, 1H), 7.4 (m, 5H), 5.7 (m, 1H), 5.4 (m, 1H), 5.31 (d, J=10.3 Hz, 1H), 5.28 (d, J=3.9 Hz, 1H), 5.10 (d, J=17.3 Hz, 1H), 4.8 (m, 1H), 4.7 (t, J=9.0 Hz, 1H), 4.3 (m, 1H).

Step 3: (4S)-3-{(2S)-2-[(S)-[3,5-Bis(trifluoromethyl)phenyl](hydroxy)methyl]but-3-enoyl}-4-phenyl-1,3-oxazolidin-2-one (20 g, 42.5 mmol) and hydrazine (2.71 g, 85 mmol) in THF (100 mL) was stirred at room temperature for 1 hour. The reaction was diluted with ethyl acetate:hexanes (2:1, 200 mL) and was partitioned with water (100 mL). The organic was washed with brine (100 mL) and was dried over sodium sulfate, filtered, and concentrated. The crude product was triturated with IPA (30 mL) to remove the chiral auxiliary. The filtrate was concentrated to yield (2S)-2-[(S)-[3,5-bis(trifluoromethyl)phenyl](hydroxy)methyl]but-3-enehydrazide (14.5 g, 42.4 mmol), which was used without further purification. $^1$H NMR (500 MHz, CDCl$_3$) δ 7.81 (s, 3H), 7.83 (s, 1H), 7.0 (br s, 1H), 5.9 (m, 1H), 5.42 (d, J=3.3 Hz, 1H), 5.29 (d, J=10.3 Hz, 1H), 5.03 (d, J=17.1 Hz, 1H), 3.1 (dd, J=9.4, 3.5 Hz, 1H).

Step 4: (2S)-2-[(S)-[3,5-Bis(trifluoromethyl)phenyl](hydroxy)methyl]but-3-enehydrazide (14.5 g, 42.4 mmol) was dissolved in IPA (100 mL) and HCl (4N in dioxane, 20 mL). tert-Butyl nitrite (5.24 g, 50.8 mmol) in IPA (20 mL) was added via a syringe pump at 50° C. over 1 hr. The reaction mixture was stirred at 50° C. and additional hour and the volatiles were removed. The crude mixture was dissolved in ethyl acetate (150 mL), washed with aqueous Na$_2$CO$_3$ (100 mL), dried over sodium sulfate, filtered and concentrated. The resultant oil was purified by column chromatography to yield (4S,5R)-5-[3,5-bis(trifluoromethyl)phenyl]-4-ethenyl-1,3-oxazolidin-2-one (7 g, 21.52 mmol) as light yellow crystalline solid. $^1$H NMR (500 MHz, CDCl$_3$) δ 7.90 (s, 1H), 7.82 (s, 2H), 5.91 (d, J=8.3 Hz, 1H), 5.2 (m, 3H), 4.7 (m, 1H).

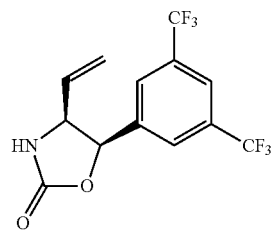 [SMILES: C=C[C@@H]1NC(=O)O[C@@H]1c1cc(C(F)(F)F)cc(C(F)(F)F)c1]

Intermediate A—Scheme A-2

(4S,5R)-5-[3,5-bis(trifluoromethyl)phenyl]-4-ethenyl-1,3-oxazolidin-2-one

Step 1: To N-Boc-allylamine (50.0 g, 0.318 mol) in anhydrous THF (800 mL) at −78° C. was added sec-butyllithium (1.30 M in cyclohexane, 538.0 mL, 0.7 mol) dropwise under a stream of N$_2$ gas. The resulting yellow solution was stirred at −78° C. for an additional 2 hours, after which time ZnCl$_2$ (1.1 M in Et$_2$O, 349.8 mL, 0.35 mol) was added. The solution was stirred for 1 hour before 3,5-bis-trifluoromethylbenzaldehyde (169.3 g, 0.700 mol) was added to the clear solution. The mixture was stirred at −78° C. for 1 hour before quenching with acetic acid (227 mL). The reaction was poured into ice water (2 L) and the organic layer was washed with aqueous saturated NaHCO$_3$ (2 L×2) and brine (1 L), was dried (MgSO$_4$), and concentrated. The crude material was recrystallized from petroleum ether (300 mL) to yield tert-butyl {1-[3,5-bis(trifluoromethyl)phenyl]-1-hydroxybut-3-en-2-yl}carbamate (57 g) as a white powder. In total this process yielded 2.8 kg of material. MS ESI calc'd. for C$_{17}$H$_{20}$F$_6$NO$_3$ [M+H]+ 400.1, found 400.0.

Step 2: At 0° C. under N$_2$, NaH (20 g, 0.500 mol) was added slowly to the mixture of tert-butyl {1-[3,5-bis(trifluoromethyl)phenyl]-1-hydroxybut-3-en-2-yl}carbamate (100 g, 0.250 mol) in anhydrous THF (1.5 L) while stirring. After the addition, the mixture was stirred at 0° C. for 1 hour, then at 80° C. for 2-6 hrs. (Caution: The mixture was stirred and heated at 80° C. for 0.5-1 hour of bubbling). The resulting mixture was cooled to 0° C. and MeOH (0.1 L) and ice water (0.2 L) was added carefully to quench the reaction. The mixture was concentrated and then diluted with ethyl acetate (2 L), washed with water (0.5 L×3), brine (0.5 L), dried and concentrated to give a black oil. Flash chromatography on silica gel yielded the crude product which was recrystallized from ethyl acetate, dichloromethane and petroleum ether to provide cis-5-[3,5-bis(trifluoromethyl)phenyl]-4-ethenyl-1,3-oxazolidin-2-one (25 g) as a white solid. The resultant solid was separated by chiral SFC (column-OJ 250 mm×50 mm, 10 um; mobile phase-A: supercritical CO$_2$, B: IPA, A:B=85:15 at 230 mL/min; column temp: 38° C.; nozzle pressure-100 bar; nozzle temp-60° C.; evaporator temp-20° C.; trimmer temp-25° C.; wavelength-220 nm). $^1$H NMR (400 MHz, DMSO-d$_6$) δ 8.30 (s, 1H), 8.10 (s, 1H), 7.93 (s, 2H), 6.05-6.03 (d, 1H), 5.27-5.11 (m, 2H), 4.99-4.97 (d, 1H), 4.76-4.73 (t, 1H).

Scheme B

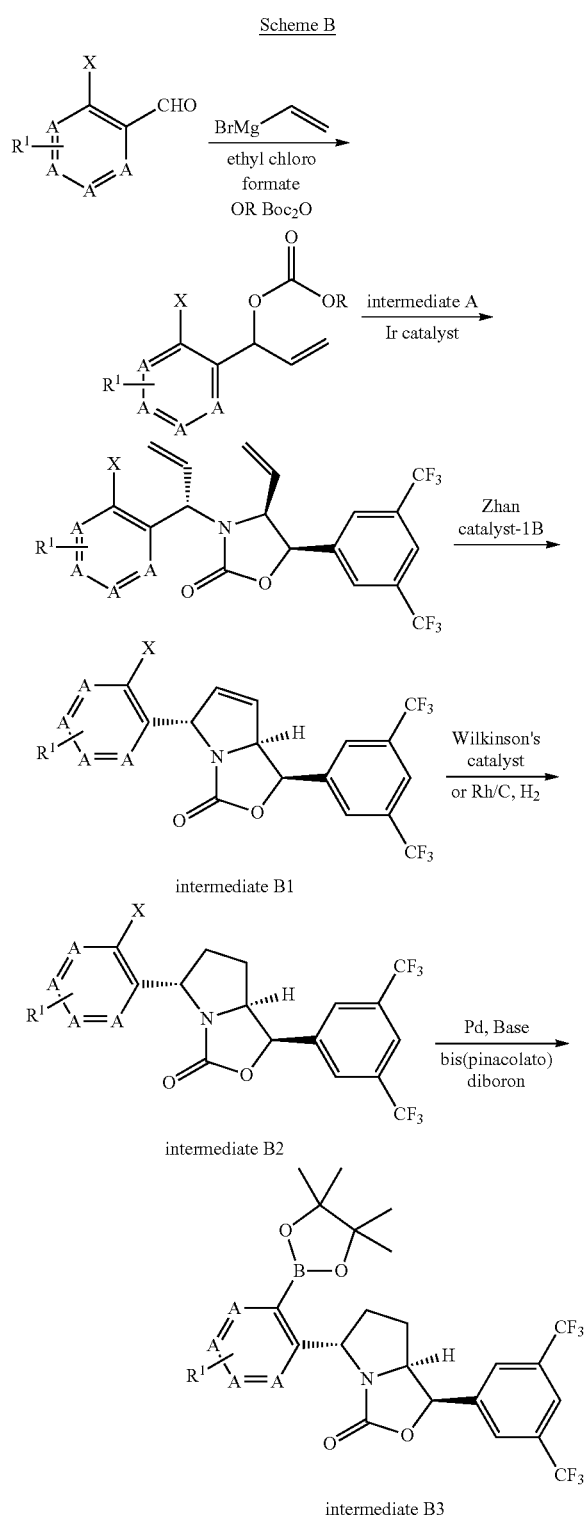

intermediate B1 intermediate B2 intermediate B3

In Scheme B, A is CH or N, where the H of CH can be substituted. The synthesis of Intermediate B begins with a known or prepared aldehyde treated with vinyl Grignard and the resultant alkoxide being directly protected as a carbonate. The carbonate is then reacted under Ir-catalysis (Hartwig et al., *J. Am. Chem. Soc.* 2010, 132, 8918-8920) with Intermediate A to provide a substrate for ring-closing metathesis to form the bicyclic core (Intermediate B1). Subsequent reduction provides Intermediate B2. B2 is converted to the corresponding boronic ester (intermediate B3) via a Pd catalyzed coupling reaction.

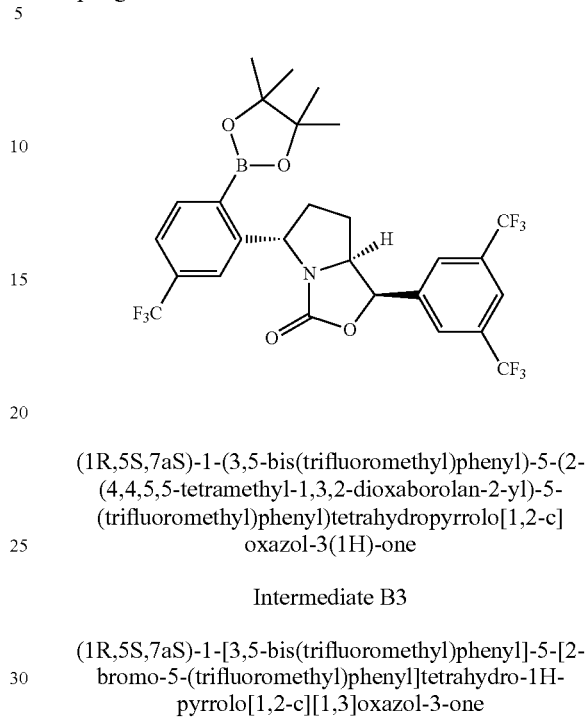

(1R,5S,7aS)-1-(3,5-bis(trifluoromethyl)phenyl)-5-(2-(4,4,5,5-tetramethyl-1,3,2-dioxaborolan-2-yl)-5-(trifluoromethyl)phenyl)tetrahydropyrrolo[1,2-c]oxazol-3(1H)-one Intermediate B3

(1R,5S,7aS)-1-[3,5-bis(trifluoromethyl)phenyl]-5-[2-bromo-5-(trifluoromethyl)phenyl]tetrahydro-1H-pyrrolo[1,2-c][1,3]oxazol-3-one Step 1a: To 2-bromo-5-trifluoromethylbenzaldehyde (20 g, 99 mmol) in THF (50 mL) was added vinyl magnesium bromide (1.0 M, 128 mL, 128 mmol) via a syringe addition at 0° C. The reaction mixture was allowed to warm to room temperature and was stirred for 30 min. The reaction was quenched with the careful, dropwise addition of ethyl chloroformate (10.7 g, 99 mmol). After stirring for 30 minutes, the reaction was diluted with hexane (100 mL) and was partitioned with aqueous saturated $NH_4Cl$. The organic was further washed with HCl (1.0 M in water, 50 mL), then brine (30 mL) before drying over sodium sulfate, filtering and concentrating to dryness. The crude material was purified by column chromatography to yield 1-(2-bromo-5-fluorophenyl)prop-2-en-1-yl ethyl carbonate (14.5 g, 47.8 mmol). $^1$H NMR (500 MHz, $CDCl_3$) δ7.56 (m, 1H), 7.24 (m, 1H), 6.97 (m, 1H), 6.43 (d, J=5.5 Hz, 1H), 6.01 (m, 1H), 5.35-5.42 (m, 2H), 4.28 (m, 2H), 1.38 (m, 3H).

Step 2: To a 500 mL RBF was added 1-(2-bromo-5-fluorophenyl)prop-2-en-1-yl ethyl carbonate (10.4 g, 29.5 mmol), (4S,5R)-5-[3,5-bis(trifluoromethyl)phenyl]-4-ethenyl-1,3-oxazolidin-2-one (4 g, 12.3 mmol), DCM (20 mL), and the Helmchen dibenzo[a,e]cyclooctatetraene (dbcot) iridium phosphoramidite catalyst complex (407 mg, 0.369 mmol) (Helmchen et al, *Chem. Eur. J.*, 2010, 16, 6601-6615). The reaction was stirred at 33° C. for 2 days open to air. The reaction was filtered over Celite and purified by column chromatography to yield (4S,5R)-5-[3,5-bis(trifluoromethyl)phenyl]-3-{(1S)-1-[2-bromo-5-(trifluoromethyl)phenyl]prop-2-en-1-yl}-4-ethenyl-1,3-oxazolidin-2-one (4.5 g, 7.65 mmol). $^1$H NMR (500 MHz, $CDCl_3$) δ7.86 (m, 2H), 7.68 (s, 2H), 7.64 (s, 1H), 7.54 (d, J=6.5 Hz, 1H), 6.22 (m, 1H), 5.75 (m, 2H), 5.43 (m, 2H), 5.20 (m, 1H), 5.03 (d, J=5.0 Hz, 1H), 4.8 (d, J=8.5 Hz, 1H), 4.1 (m, 1H).

Step 3: To a 100 mL RBF equipped with a reflux condenser was added (4S,5R)-5-[3,5-bis(trifluoromethyl)phenyl]-3-

{(1S)-1-[2-bromo-5-(trifluoromethyl)phenyl]prop-2-en-1-yl}-4-ethenyl-1,3-oxazolidin-2-one (4.5 g, 7.65 mmol) and toluene (20 mL). The system was flushed with nitrogen and 1,3-bis(2,4,6-trimethylphenyl)-4,5-dihydroimidazol-2-ylidene[2-(i-propoxy)-5-(N,N-dimethylaminosulfonyl)phenyl]methyleneruthenium(II) dichloride (274 mg, 0.374 mmol) (Zhan catalyst-1B) was added. The reaction mixture was heated at 60° C. for 2 hours. The solvent was removed under reduced pressure and the resultant oil was purified by column chromatography to yield (1R,5S,7aS)-1-[3,5-bis(trifluoromethyl)phenyl]-5-[2-bromo-5-(trifluoromethyl)phenyl]-5,7a-dihydro-1H-pyrrolo[1,2-c][1,3]oxazol-3-one (Intermediate B1) 4.0 g, 7.14 mmol). $^1$H NMR (500 MHz, CDCl$_3$) δ7.95 (s, 1H), 7.79 (s, 2H), 7.76 (d, J=8.3 Hz, 1H), 7.60 (s, 1H), 7.47 (d, J=8.2 Hz, 1H), 6.34 (d, J=2.5 Hz, 1H), 6.17 (s, H), 6.12 (d, J=8.8 Hz, 1H), 5.46 (d, J=8.7 Hz, 1H), 5.29 (d, J=4.8 Hz, 1H).

Step 4: To (1R,5S,7aS)-1-[3,5-bis(trifluoromethyl)phenyl]-5-[2-bromo-5-(trifluoromethyl)phenyl]-5,7a-dihydro-1H-pyrrolo[1,2-c][1,3]oxazol-3-one (3.0 g, 5.36 mmol) in ethanol (10 mL) was added Wilkinson's catalyst (Rh(PPh$_3$)$_3$Cl) (495 mg, 0.536 mmol). The mixture was placed on a Parr shaker under an atmosphere of hydrogen gas at 40 psi overnight. Upon completion, the solvent was removed under reduced pressure and the resultant oil was purified by column chromatography to yield (1R,5S,7aS)-1-[3,5-bis(trifluoromethyl)phenyl]-5-[2-bromo-5-(trifluoromethyl)phenyl]tetrahydro-1H-pyrrolo[1,2-c][1,3]oxazol-3-one (Intermediate B2), (3.0 g, 5.34 mmol). $^1$H NMR (500 MHz, CDCl$_3$) δ7.93 (s, 1H), 7.87 (s, 2H), 7.73 (m, 2H), 7.44 (d, J=2 Hz, 1H), 6.14 (d, J=7.9 Hz, 1H), 6.12 (d, J=8.8 Hz, 1H), 5.35 (m, 1H), 4.63 (m, 1H), 3.03 (m, 1H), 1.69 (m, 1H), 1.25 (m, 2H).

Step 5: To a 40 mL vial in glove box were added (1R,5S,7aS)-1-[3,5-bis(trifluoromethyl)phenyl]-5-[2-bromo-5-(trifluoromethyl)phenyl]tetrahydro-1H-pyrrolo[1,2-c][1,3]oxazol-3-one (intermediate B2, 2.0 g, 3.56 mmol), bis(pinacolato)diboron (1.84 g, 7.11 mmol), potassium acetate (0.87 g, 8.9 mmol), 1,1'-bis(di-tert-butylphosphino)ferrocene palladium dichloride (0.122 g, 0.178 mmol) and 20 mL dimethylacetamide. The vial was sealed and heated at 80° C. for 20 hrs. Reaction mixture was diluted with methyl tButyl ether, washed with 15% NaCl aqueous solution. Organics were treated with metal scavenger resin and concentrated. Crude product was purified by column chromatography to yield (1R,5S,7aS)-1-(3,5-bis(trifluoromethyl)phenyl)-5-(2-(4,4,5,5-tetramethyl-1,3,2-dioxaborolan-2-yl)-5-(trifluoromethyl)phenyptetrahydropyrrolo[1,2-c]oxazol-3(1H)-one (Intermediate B3, 1.65 g, 2.71 mmol). MS ESI calc'd. for C$_{27}$H$_{25}$BF$_9$NO$_4$ [M+H]+ 610.2, found 610.2.

The following intermediates in Table 1 were prepared according to Scheme B using the procedures outlined in the syntheses of Intermediates B1, B2, and B3 utilizing commercially available or known aldehydes in Step 1. In some cases, Step 3 can be carried out using the Hoyveda-Grubbs second generation catalyst or Schrock's catalyst. Additionally, Step 4 may be carried out using Rh/C as the catalyst. For Intermediates B11 and B13, aldehyde starting materials 2-bromo-3-methyl-5-(trifluoromethyl)benzaldehyde and 5-bromo-2-(trifluoromethyl)isonicotinaldehyde were synthesized based on the following schemes.

2-bromo-3-methyl-5-(trifluoromethyl)benzaldehyde

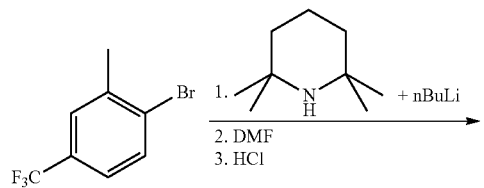

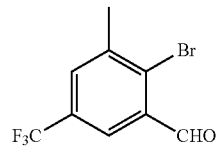

To a 100 mL round bottom flask were added 2,2,6,6-tetramethylpiperidine (2.8 mL, 16.6 mmol), and 50 mL THF. BuLi (9.5 mL, 15.2 mmol, 1.6 M hexane solution) was added via a syringe at 0° C. After stirring at 0° C. for 15 mins, ice bath was replaced with dry ice/ether bath. To another 25 mL round bottom flask was added 1-bromo-2-methyl-4-(trifluoromethyl)benzene (3.3 g, 13.8 mmol) and THF. After cooling with dry ice/acetone bath, this solution was cannular transferred to the first flask rapidly. Upon completion of transferring, DMF (2.1 mL, 27.6 mmol) was added immediately and the resulting reaction mixture was stirred at that temperature for 10 more minutes before it was allowed to warm to −20° C. slowly. The reaction was quenched at −20° C. with addition of 50 mL 1N HCl. This mixture was diluted with 100 mL water and extracted with 100 mL EtOAc/hexane 1:9. The organics were washed with 30 mL NaHCO3 aqueous solution, dried over sodium sulfate, filtered and concentrated. Crude product was purified by chromatography to give 1.8 g 2-bromo-3-methyl-5-(trifluoromethyl)benzaldehyde. $^1$H NMR (500 MHz, CDCl$_3$) δ10.50 (s, 1H), 8.03 (d, J=1.4 Hz, 1H), 7.75 (d, J=1.5 Hz, 1H), 2.60 (s, 3H).

5-bromo-2-(trifluoromethyl)pyridine-4-carbaldehyde

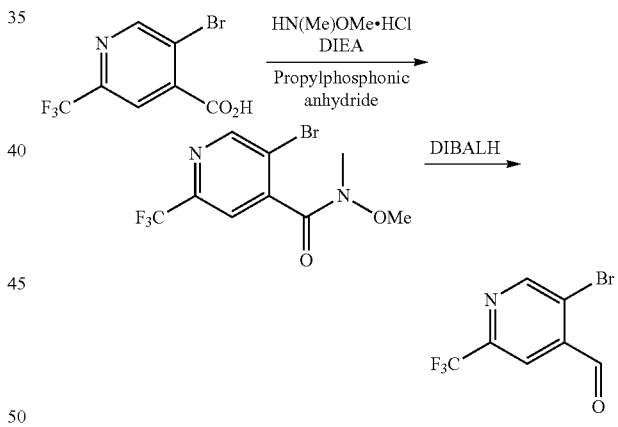

Step 1: To 5-bromo-2-(trifluoromethyl)isonicotinic acid (20 g, 74.1 mmol), N,O-dimethylhydroxylamine hydrochloride (10.84 g, 111 mmol), and DIPEA (38.8 mL, 222 mmol) in DMF (100 mL) was added 2,4,6-tripropyl-1,3,5,2,4,6-trioxatriphosphinane 2,4,6-trioxide (53.4 mL, 89 mmol) at 0° C. by a dropping funnel over a period of 10 minutes. The reaction was stirred for 2 hours. The reaction was concentrated to half the amount and was diluted with EtOAc. The organic was partitioned with satd. NH$_4$Cl and then with brine. The organic was dried over Na$_2$SO$_4$, filtered and concentrated in vacuo. 5-bromo-N-methoxy-N-methyl-2-(trifluoromethyl)pyridine-4-carboxamide (21 g, 67.1 mmol) was carried forward as a crude oil. $^1$H NMR (500 MHz, CDCl$_3$) δ8.90 (s, 1H), 7.63 (s, 1H), 3.44 (s, 3H), 3.55 (s, 3H).

Step 2: To 5-bromo-N-methoxy-N-methyl-2-(trifluoromethyl)pyridine-4-carboxamide (21 g, 67.1 mmol) in THF (200 mL) was added DIBAL-H in toluene (1M, 73.8 mL, 73.8 mmol) through a syringe at −78° C. The reaction was stirred for 40 minutes while it was warmed to −10° C. The reaction was diluted with EtOAc (100 mL) and was quenched with 1N HCl solution (150 mL). The reaction mixture was filtered on a Celite and silica gel bed. The layers were separated and the organic layer was partitioned with saturated. NaHCO$_3$ and then brine. The organic layer was dried over Na$_2$SO$_4$, filtered and concentrated in vacuo. The crude reaction was purified by column chromatography to yield 5-bromo-2-(trifluoromethyl)pyridine-4-carbaldehyde (13.1 g, 51.6 mmol). $^1$H NMR (500 MHz, CDCl$_3$) δ10.2 (s, 1H), 9.04 (s, 1H), 8.84 (s, 1H).

TABLE 1

| Int | Structure | IUPAC Name | Exact Mass [M + H]+ or $^1$H NMR |
|---|---|---|---|
| B4 | 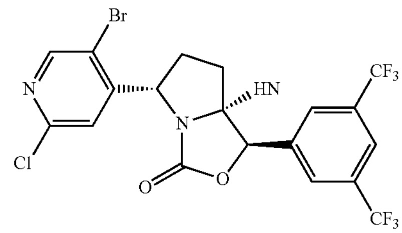 [SMILES: N[C@@]12CC[C@@H](c3cc(Cl)ncc3Br)N1C(=O)O[C@@H]2c1cc(C(F)(F)F)cc(C(F)(F)F)c1] | (1R,5S,7aS)-1-[3,5-bis(trifluoromethyl)phenyl]-5-(5-bromo-2-chloropyridin-4-yl)tetrahydro-1H-pyrrolo[1,2-c][1,3]oxazol-3-one | $^1$H NMR (500 MHz, CDCl$_3$) δ8.51 (s, 1H), 7.95 (s, 1H), 7.86 (s, 2H), 7.46 (s, 1H), 6.13 (d, J = 8.8 Hz, 1H), 5.25 (m, 1H), 4.59 (m, 1H), 3.0 (m, 1H), 1.69 (m, 1H), 1.25 (m, 2H). |
| B5 | 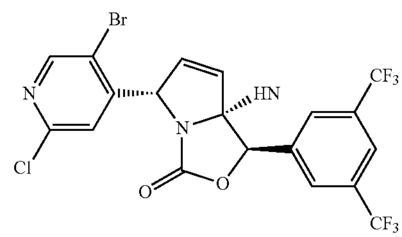 | (1R,5S,7aS)-1-[3,5-bis(trifluoromethyl)phenyl]-5-(5-bromo-2-chloropyridin-4-yl)-5,7a-dihydro-1H-pyrrolo[1,2-c][1,3]oxazol-3-one | Calc'd 529.0 and 527.0 found 528.9 and 526.9 |
| B6 | 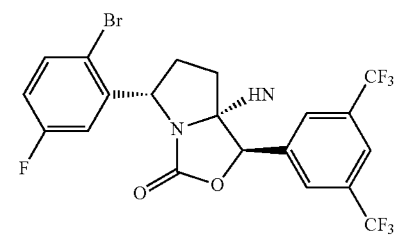 [SMILES: N[C@@]12CC[C@@H](c3cc(F)ccc3Br)N1C(=O)O[C@@H]2c1cc(C(F)(F)F)cc(C(F)(F)F)c1] | (1R,5S,7aS)-1-[3,5-bis(trifluoromethyl)phenyl]-5-(2-bromo-5-fluorophenyl)tetrahydro-1H-pyrrolo[1,2-c][1,3]oxazol-3-one | $^1$H NMR (500 MHz, CDCl$_3$) δ7.95 (s, 1H), 7.86 (s, 2H), 7.54 (m, 1H), 7.23 (m, 1H), 6.92 (m, 1H), 6.09 (d, J = 8.0 Hz, 1H), 5.25 (m, 1H), 4.59 (m, 1H), 2.98 (m, 1H), 1.67 (m, 1H), 1.25 (m, 2H). |
| B7 | 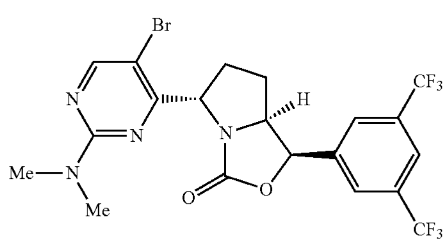 [SMILES: CN(C)c1ncc(Br)c([C@@H]2CC[C@H]3[C@@H](c4cc(C(F)(F)F)cc(C(F)(F)F)c4)OC(=O)N23)n1] | (1R,5S,7aS)-1-[3,5-bis(trifluoromethyl)phenyl]-5-[5-bromo-2-(dimethylamino)pyrimidin-4-yl]tetrahydro-1H-pyrrolo[1,2-c][1,3]oxazol-3-one | Calc'd 539.0 and 541.0 found 538.9 and 540.9 |
| B8 | 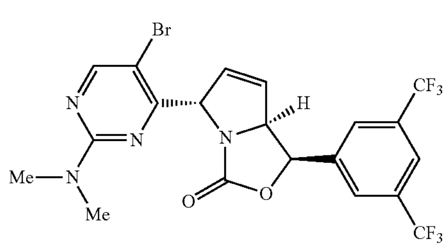 [SMILES: CN(C)c1ncc(Br)c([C@@H]2C=C[C@H]3[C@@H](c4cc(C(F)(F)F)cc(C(F)(F)F)c4)OC(=O)N23)n1] | (1R,5S,7aS)-1-[3,5-bis(trifluoromethyl)phenyl]-5-[5-bromo-2-(dimethylamino)pyrimidin-4-yl]-5,7a-dihydro-1H-pyrrolo[1,2-c][1,3]oxazol-3-one | Calc'd 539.0 and 537.0 found 538.9 and 536.9 |

TABLE 1-continued

| Int | Structure | IUPAC Name | Exact Mass [M + H]+ or ¹H NMR |
|---|---|---|---|
| B9 | 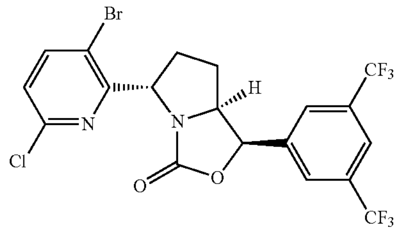 [SMILES: O=C1O[C@H](c2cc(C(F)(F)F)cc(C(F)(F)F)c2)[C@@H]2CC[C@@H](c3nc(Cl)ccc3Br)N12] | (1R,5S,7aS)-1-[3,5-bis(trifluoromethyl)phenyl]-5-(3-bromo-6-chloropyridin-2-yl)tetrahydro-1H-pyrrolo[1,2-c][1,3]oxazol-3-one | Calc'd 529.0 and 531.0 found 529.0 and 531.0 |
| B10 | 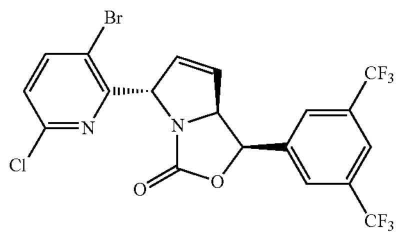 [SMILES: O=C1O[C@H](c2cc(C(F)(F)F)cc(C(F)(F)F)c2)[C@@H]2C=C[C@@H](c3nc(Cl)ccc3Br)N12] | (1R,5S,7aS)-1-[3,5-bis(trifluoromethyl)phenyl]-5-(3-bromo-6-chloropyridin-2-yl)-5,7a-dihydro-1H-pyrrolo[1,2-c][1,3]oxazol-3-one | Calc'd 529.0 and 527.0 found 529.0 and 527.0 |
| B11 | 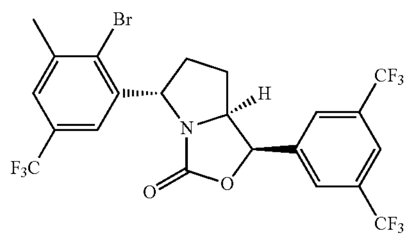 | (1R,5S,7aS)-1-(3,5-bis(trifluoromethyl)phenyl)-5-(2-bromo-3-methyl-5-(trifluoromethyl)phenyl)tetrahydropyrrolo[1,2-c]oxazol-3(1H)-one | ¹H NMR (500 MHz, CDCl$_3$) δ 7.95 (s, 1H), 7.89 (s, 2H), 7.54 (s, 1H), 7.47 (s, 1H), 6.15 (d, J = 8.0 Hz, 1H), 5.41 (t, J = 8.0 Hz, 1H), 4.63 (m, 1H), 3.02 (m, 1H), 2.53 (s, 3H), 1.62 (m, 1H), 1.55 (m, 1H), 1.26 (m, 1H). |
| B12 | 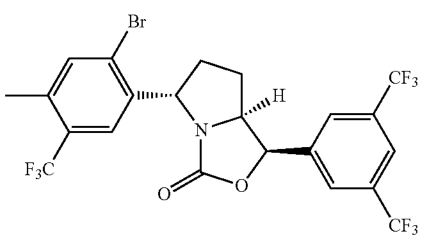 [SMILES: Cc1cc(Br)c([C@@H]2CC[C@H]3[C@@H](c4cc(C(F)(F)F)cc(C(F)(F)F)c4)OC(=O)N23)cc1C(F)(F)F] | (1R,5S,7aS)-1-(3,5-bis(trifluoromethyl)phenyl)-5-(2-bromo-4-methyl-5-(trifluoromethyl)phenyl)tetrahydropyrrolo[1,2-c]oxazol-3(1H)-one | Calc'd 575.3 and 577.3, found 575.9 and 577.9 |
| B13 | 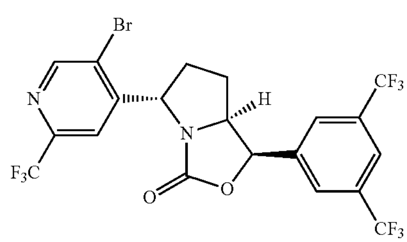 | (1R,5S,7aS)-1-(3,5-bis(trifluoromethyl)phenyl)-5-(5-bromo-2-(trifluoromethyl)pyridin-4-yl)tetrahydropyrrolo[1,2-c]oxazol-3(1H)-one | Calc'd 563.0 and 565.0 found 563.1 and 565.1 |
| B14 | 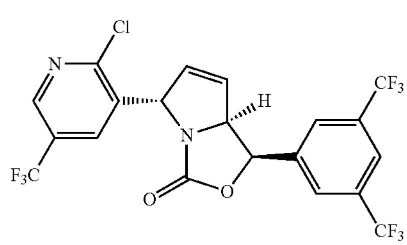 [SMILES: O=C1O[C@H](c2cc(C(F)(F)F)cc(C(F)(F)F)c2)[C@@H]2C=C[C@@H](c3cc(C(F)(F)F)cnc3Cl)N12] | (1R,5S,7aS)-1-(3,5-bis(trifluoromethyl)phenyl)-5-(2-chloro-5-(trifluoromethyl)pyridin-3-yl)-1,7a-dihydropyrrolo[1,2-c]oxazol-3(5H)-one | Calc'd 517.0 and 516.8 |

TABLE 1-continued

| Int | Structure | IUPAC Name | Exact Mass [M + H]+ or $^1$H NMR |
|---|---|---|---|
| B15 | 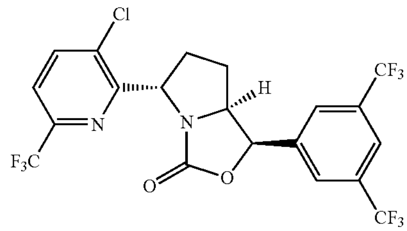 [SMILES: Cc1cc([C@H]2OC(=O)N3[C@H](c4cc(C(F)(F)F)ccc4Br)CC[C@@H]23)cc(C(F)(F)F)c1] | (1R,5S,7aS)-1-(3,5-bis(trifluoromethyl)phenyl)-5-(3-chloro-6-(trifluoromethyl)pyridin-2-yl)tetrahydropyrrolo[1,2-c]oxazol-3(1H)-one | Calc'd 519.0 found 519 |

Scheme C

Intermediate C 1-ethenyl-3-methyl-5-(trifluoromethyl)benzene

Preparation of Intermediate C is carried out via a Suzuki coupling reaction of a commercially available bromide and boronic ester to yield the desired product.

To 1-bromo-3-methyl-5-(trifluoromethyl)benzene (500 mg, 2.51 mmol) was added THF (5 mL), aqueous tribasic potassium phosphate (2.0 M, 4.18 mL, 8.37 mmol), 2-ethenyl-4,4,5,5-tetramethyl-1,3,2-dioxaborolane (387 mg, 2.51 mmol), palladium(II) acetate (47 mg, 0.209 mmol), and 1,1'-bis(di-t-butylphosphino)ferrocene (99 mg, 0.209 mmol). The system was flushed with nitrogen gas and was heated at 80° C. for 1 hour. The reaction was filtered and then diluted with ethyl acetate and water. The organic layer was dried over sodium sulfate, filtered and concentrated. The crude product was purified by preparative TLC to yield 1-ethenyl-3-methyl-5-(trifluoromethyl)benzene (300 mg, 1.61 mmol). $^1$H NMR (500 MHz, CDCl$_3$) δ7.47 (s, 1H), 7.40 (s, 1H), 7.34 (s, 1H), 6.76 (m, 1H), 5.85 (d, J=17.6 Hz, 1H), 2.43 (s, 1H).

Scheme D

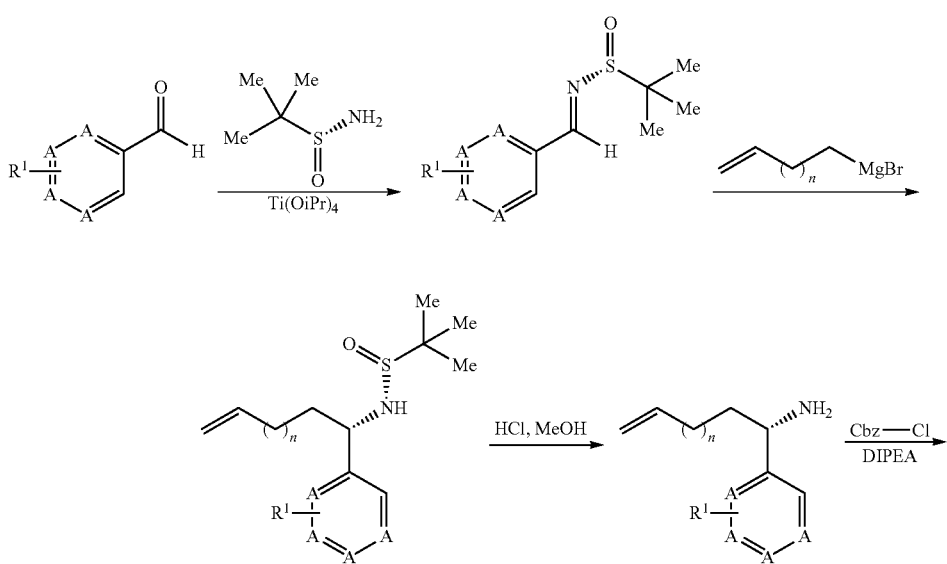

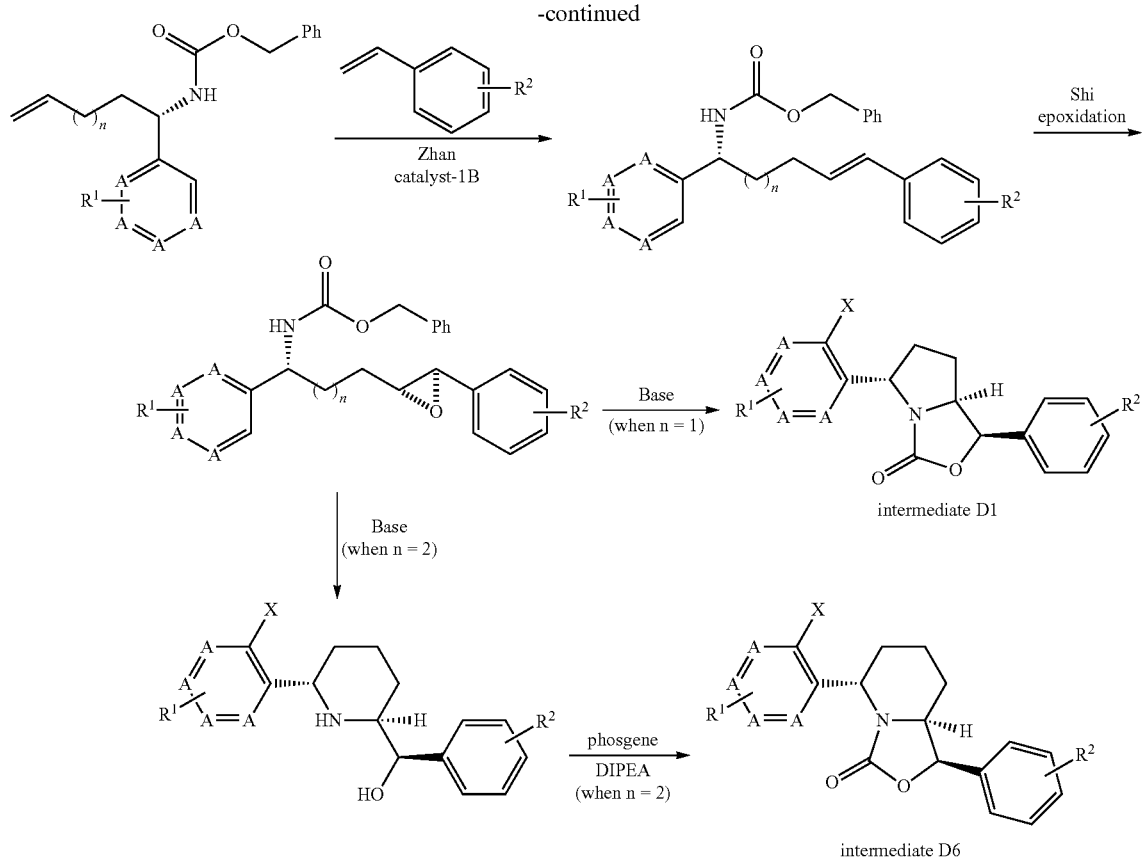

intermediate D1 intermediate D6

The synthesis of Intermediate D is from a known or prepared aldehyde which is condensed with a chiral sulfinamide auxiliary. Reaction with a prepared Grignard and subsequent deprotection yields an enantioenriched benzylic amine. Protection of the amine and cross-metathesis with a known or prepared styrene provides the precursor olefin for the Shi epoxidation (Shi et al, Chem. Rev., 2008, 108, 3958-3987). Base-mediated cyclization provides Intermediate D with high diastereoselectivity.

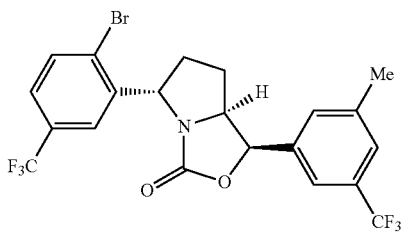

Intermediate D1

(1R,5S,7aS)-5-[2-bromo-5-(trifluoromethyl)phenyl]-1-[3-methyl-5-(trifluoromethyl)phenyl]tetrahydro-1H-pyrrolo[1,2-c][1,3]oxazol-3-one Step 1: To a 250 mL RBF was added (R)-(+)-2-methyl-2-propanesulfinamide (3.16 g, 26.1 mmol), 2-bromo-5-trifluorobenzaldehyde (6.0 g, 23.7 mmol), and THF (20 mL). Titanium(IV) ethoxide (10.8 g, 47.4 mmol) was added dropwise via a syringe before heating the reaction at 40° C. for 1 hour. The reaction was cooled to room temperature and water (100 mL) and ethyl acetate (100 mL) were added. The organic was stirred with brine for 15 min and was filtered to remove solids. The organic was dried over sodium sulfate, filtered and concentrated before purifying by column chromatography to yield N-{(E)-[2-bromo-5-(trifluoromethyl)phenyl]methylidene}-2-methylpropane-2-sulfinamide (8.0 g, 22.5 mmol) as a colorless crystalline solid. $^1$H NMR (500 MHz, CDCl$_3$) δ7.72 (m, 2H), 7.44 (m, 3H), 6.06 (d, J=8.1 Hz, 1H), 5.33 (t, J=8 Hz, 1H), 4.57 (m, 1H), 2.99 (m, 1H), 2.48 (s, 3H), 1.68 (m, 1H), 1.59 (m, 1H), 1.38 (m, 1H).

Step 2: To a 100 mL three-neck RBF equipped with stir bar and condenser was added Mg (excess), catalytic iodine, THF (20 mL), followed by 4-bromobut-1-ene (4.55 g, 33.7 mmol) in small increments. The mixture was heated to 40° C. for 1 hour. The reaction was cooled to room temperature and the freshly made Grignard reagent was added via syringe into a 250 mL RBF with N-{(E)-[2-bromo-5-(trifluoromethyl)phenyl]methylidene}-2-methylpropane-2-sulfinamide (8.0 g, 22.5 mmol) in THF (100 mL). Upon completion, the reaction was quenched with saturated aqueous NH$_4$Cl and partitioned with ethyl acetate. The organic was dried over sodium sulfate, filtered, concentrated and purified by column chromatography to yield N-{(1S)-1-[2-bromo-5-(trifluoromethyl)phenyl]pent-4-en-1-yl}-2-methylpropane-2-sulfinamide (6.0 g, 14.6 mmol). $^1$H NMR (500 MHz, CDCl$_3$) δ7.72 (m, 2H), 7.42 (d, J=8.2 Hz, 1H), 5.87 (m, 1H), 5.13 (m, 2H), 5.02 (m, 1H), 2.24 (m, 1H), 2.18 (m, 1H), 2.08 (m, 1H), 1.98 (m, 1H), 1.27 (s, 9H).

Step 3: To N-{(1S)-1-[2-bromo-5-(trifluoromethyl)phenyl]pent-4-en-1-yl}-2-methylpropane-2-sulfinamide (6.0 g, 14.6 mmol) in methanol (80 mL) was added HCl (4 N in dioxanes, 25.5 mL, 102 mmol). The reaction was stirred overnight at room temperature and the solvent was removed in vacuo. The resulting oil was partitioned with ethyl acetate and was washed with 10% aqueous potassium hydroxide. The organic was dried over sodium sulfate and was concentrated. (1S)-1-[2-Bromo-5-(trifluoromethyl)phenyl]pent-4-en-1-amine (4.4 g, 14.3 mmol) was carried forward without further purification. MS ESI calc'd. for $C_{12}H_{14}BrF_3N$ [M+H]+ 308.0 and 310.0, found 308.0 and 310.0.

Step 4: To DIPEA (7.48 mL, 42.8 mmol) and (1S)-1-[2-bromo-5-(trifluoromethyl)phenyl]pent-4-en-1-amine (4.4 g, 14.3 mmol) in DCM (20 mL) was added benzyl chloroformate at 0° C. The reaction was stirred at room temperature for 2 hours and was quenched with water. The organic was washed with 10% aqueous KOH and the aqueous was back-extracted with ethyl acetate. The combined organics were dried over sodium sulfate, filtered, concentrated and then purified by column chromatography to yield benzyl {(1S)-1-[2-bromo-5-(trifluoromethyl)phenyl]pent-4-en-1-yl}carbamate (5.8 g, 13.1 mmol). $^1$H NMR (500 MHz, $CDCl_3$) δ7.72 (m, 1H), 7.58 (s, 1H), 7.39 (b, 5H), 7.1 (m, 1H), 5.83 (m, 1H), 5.3 (b, 1H), 5.15 (m, 3H), 2.22 (m, 1H), 2.18 (m, 1H), 1.95 (m, 1H), 1.78 (m, 1H).

Step 5: To a 100 mL RBF equipped with a reflux condenser was added benzyl {(1S)-1-[2-bromo-5-(trifluoromethyl)phenyl]pent-4-en-1-yl}carbamate (0.5 g, 1.13 mmol), 1-ethenyl-3-methyl-5-(trifluoromethyl)benzene (421 mg, 2.26 mmol) and dichloromethane (10 mL). The system was flushed with nitrogen and 1,3-bis(2,4,6-trimethylphenyl)-4,5-dihydroimidazol-2-ylidene[2-(i-propoxy)-5-(N,N-dimethylaminosulfonyl)phenyl]methyleneruthenium(II) dichloride (41 mg, 0.57 mmol) (Zhan catalyst-1B) was added before heating at 60° C. for 20 min. The reaction was cooled to room temperature and was directly purified by column chromatography to yield benzyl {(1R,4E)-1-[2-bromo-5-(trifluoromethyl)phenyl]-5-[3-methyl-5-(trifluoromethyl)phenyl]pent-4-en-1-yl}carbamate (500 mg, 0.833 mmol). $^1$H NMR (500 MHz, $CDCl_3$) δ7.72 (m, 1H), 7.58 (s, 1H), 7.39 (b, 5H), 6.4 (d, J=8.2 Hz, 1H), 6.25 (m, 1H), 5.35 (m, 1H), 5.20 (m, 1H), 5.10 (s, 2H), 2.40 (s, 3H), 2.19 (m, 1H), 2.05 (m, 1H), 1.95 (m, 1H), 1.78 (m, 1H).

Step 6: To a 250 mL RBF was added tetrabutylammonium hydrogen sulfate (28 mg, 0.083 mmol), D-Epoxone (215 mg, 0.833 mmol), benzyl {(1R,4E)-1-[2-bromo-5-(trifluoromethyl)phenyl]-5-[3-methyl-5-(trifluoromethyl)phenyl]pent-4-en-1-yl}carbamate (500 mg, 0.833 mmol) followed by MeCN (7 mL) and EtOAc (6 mL). Sodium tetraborate decahydrate (318 mg, 0.833 mmol) in an aqueous ethylenediaminetetraacetic acid disodium salt dihydrate solution (0.4 mM, 7 mL) was added to the reaction at 0° C. A solution of potassium carbonate (1.51 g, 8.33 mmol) in water (7 mL) and a solution of OXONE® (1.54 g, 2.50 mmol) in an aqueous ethylenediaminetetraacetic acid disodium salt dihydrate (0.4 mM, 7 mL) were simultaneously added to the reaction at 0° C. over the course of two hours. An additional solution of D-Epoxone (107 mg, 0.417 mmol) in MeCN (3 mL) was added via syringe pump over 1.5 hours. The reaction was diluted with water (100 mL) and was extracted with ethyl acetate (2×100 mL). The organic was concentrated and purified by column chromatography to yield benzyl [(1S)-1-[2-bromo-5-(trifluoromethyl)phenyl]-3-{(2R,3R)-3-[3-methyl-5-(trifluoromethyl)phenyl]oxiran-2-yl}propyl]carbamate (300 mg, 0.487 mmol). $^1$H NMR (500 MHz, $CDCl_3$) δ7.73 (m, 1H), 7.56 (s, 1H), 7.38-7.42 (b, 5H), 5.47 (m, 1H), 5.21 (m, 1H), 5.12 (s, 2H), 3.67 (s, 1H), 3.02 (s, 1H), 2.42 (s, 3H), 2.10 (m, 1H), 1.99 (m, 2H), 1.76 (m, 1H).

Step 7: To benzyl [(1S)-1-[2-bromo-5-(trifluoromethyl)phenyl]-3-{(2R,3R)-3-[3-methyl-5-(trifluoromethyl)phenyl]oxiran-2-yl}propyl]carbamate (100 mg, 0.162 mmol) in DMF (2 mL) was added LiHMDS (1.0 M, 0.324 mL, 0.324 mmol) at 0° C. The mixture was stirred at room temperature overnight and the solvent was removed under reduced pressure. The resultant residue was purified by preparative TLC to yield (1R,5S,7aS)-5-[2-bromo-5-(trifluoromethyl)phenyl]-1-[3-methyl-5-(trifluoromethyl)phenyl]tetrahydro-1H-pyrrolo[1,2-c][1,3]oxazol-3-one (75 mg, 0.148 mmol). $^1$H NMR (500 MHz, $CDCl_3$) δ7.72 (m, 2H), 7.46 (s, 1H), 7.44 (d, J=8.8 Hz, 3H), 6.06 (d, J=8.1 Hz, 1H), 5.33 (t, J=8.0 Hz, 1H), 4.57 (m, 1H), 2.99 (m, 1H), 2.48 (s, 3H), 1.68 (m, 1H), 1.57 (m, 1H), 1.38 (m, 1H).

The following intermediates in Table 2 were prepared according to Scheme D using the procedure outlined in the synthesis of Intermediate D1 utilizing commercially available or known aldehydes in Step 1. In addition to LiHMDS, an alternative base that can be used in Step 7 is DBU.

TABLE 2

| Int | Structure | IUPAC Name | Exact Mass [M + H]+ or $^1$HNMR |
|---|---|---|---|
| D2 | 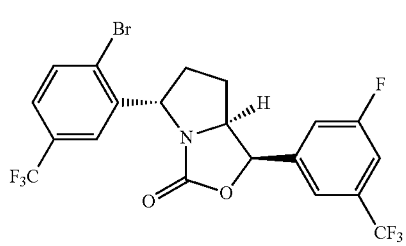 | (1R,5S,7aS)-5-[2-bromo-5-(trifluoromethyl)phenyl]-1-[3-fluoro-5-(trifluoromethyl)phenyl]tetrahydro-1H-pyrrolo[1,2-c][1,3]oxazol-3-one | $^1$H NMR (500 MHz, $CDCl_3$) δ7.75 (m, 2H), 7.46 (s, 1H), 7.44 (d, J = 8.8 Hz, 1H), 7.42 (m, 2H), 6.07 (d, J = 8.1 Hz, 1H), 5.34 (t, J = 8.0 Hz, 1H), 4.59 (m, 1H), 3.02 (m, 1H), 1.68 (m, 1H), 1.60 (m, 1H), 1.33 (m, 1H). |

TABLE 2-continued

| Int | Structure | IUPAC Name | Exact Mass [M + H]+ or ¹HNMR |
|---|---|---|---|
| D3 | 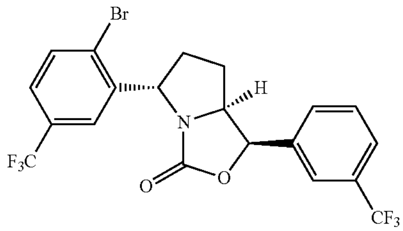 | (1R,5S,7aS)-5-[2-bromo-5-(trifluoromethyl)phenyl]-1-[3-(trifluoromethyl)phenyl]tetrahydro-1H-pyrrolo[1,2-c][1,3]oxazol-3-one | ¹H NMR (500 MHz, CDCl₃) δ7.73 (m, 2H), 7.71 (s, 2H), 7.43 (d, J = 8.1 Hz, 1H), 6.09 (d, J = 8.1 Hz, 1H), 5.33 (t, J = 8.0 Hz, 1H), 4.57 (m, 1H), 2.99 (m, 1H), 1.53-1.66 (b, 2H), 1.38 (m, 1H). |
| D4 | 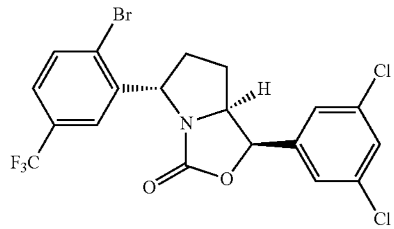 [SMILES: O=C1O[C@H](c2cc(Cl)cc(Cl)c2)[C@@H]2CC[C@@H](c3cc(C(F)(F)F)ccc3Br)N12] | (1R,5S,7aS)-5-[2-bromo-5-(trifluoromethyl)phenyl]-1-(3,5-dichlorophenyl)tetrahydro-1H-pyrrolo[1,2-c][1,3]oxazol-3-one | ¹H NMR (500 MHz, CDCl₃) δ8.04 (s, 1H), 7.72 (m, 2H), 7.44 (m, 3H), 5.98 (d, J = 8.1 Hz, 1H), 5.32 (t, J = 8.0 Hz, 1H), 4.59 (m, 1H), 3.02 (m, 1H), 1.68 (m, 1H), 1.60 (m, 1H), 1.33 (m, 1H). |
| D5 | 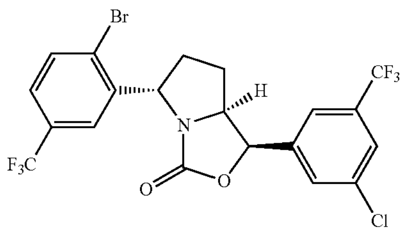 [SMILES: O=C1O[C@H](c2cc(Cl)cc(C(F)(F)F)c2)[C@@H]2CC[C@@H](c3cc(C(F)(F)F)ccc3Br)N12] | (1R,5S,7aS)-5-[2-bromo-5-(trifluoromethyl)phenyl]-1-[3-chloro-5-(trifluoromethyl)phenyl]tetrahydro-1H-pyrrolo[1,2-c][1,3]oxazol-3-one | ¹H NMR (500 MHz, CDCl₃) δ7.73 (m, 2H), 7.65 (s, 1H), 7.61 (s, 1H), 7.58 (s, 1H), 7.42 (d, J = 8.8 Hz, 1H), 6.06 (d, J = 8.1 Hz, 1H), 5.34 (t, J = 8.0 Hz, 1H), 4.59 (m, 1H), 3.02 (m, 1H), 1.68 (m, 1H), 1.60 (m, 1H), 1.33 (m, 1H). |

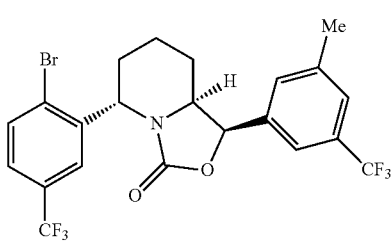 [SMILES: Cc1cc([C@H]2OC(=O)N3[C@H](c4cc(C(F)(F)F)ccc4Br)CCC[C@@H]23)cc(C(F)(F)F)c1]

Intermediate D6

(1R,5S,8aS)-1-[3,5-bis(trifluoromethyl)phenyl]-5-[2-bromo-5-(trifluoromethyl)phenyl]hexahydro[1,3]oxazolo[3,4-a]pyridin-3-one Step 1: To a 100 mL three-neck RBF equipped with stir bar and condenser was added Mg (excess), catalytic iodine, THF (20 mL), followed by 5-bromopent-1-ene (1.93 g, 12.9 mmol) added in small increments. The mixture was heated to 40° C. for 1 hour. The reaction was cooled to room temperature and the freshly made Grignard reagent was added via syringe into a 250 mL RBF with N-{(E)-[2-bromo-5-(trifluoromethyl)phenyl]methylidene}-2-methylpropane-2-sulfinamide (2.3 g, 6.5 mmol) in THF (20 mL). Upon completion, the reaction was quenched with saturated aqueous NH₄Cl and partitioned with ethyl acetate. The organic was dried over sodium sulfate, filtered, concentrated and purified by column chromatography to yield N-{(1S)-1-[2-bromo-5-(trifluoromethyl)phenyl]hex-5-en-1-yl}-2-methylpropane-2-sulfinamide (1.5 g, 3.5 mmol). ¹H NMR (500 MHz, CDCl₃) δ7.71 (d, J=8.4 Hz, 1H), 7.63 (s, 1H), 7.41 (d, J=6.4 Hz, 1H), 5.77 (m, 1H), 5.03 (m, 2H), 4.87 (m, 1H), 3.65 (m, 1H), 2.11 (m, 2H), 1.86 (m, 1H), 1.82 (m, 1H), 1.55 (m, 1H), 1.40 (m, 1H), 1.22 (s, 9H).

Step 2: To N-{(1S)-1-[2-bromo-5-(trifluoromethyl)phenyl]hex-5-en-1-yl}-2-methylpropane-2-sulfinamide (1.5 g, 3.5 mmol) was added HCl (4 N in dioxanes, 6.16 mL, 24.6 mmol). The reaction was stirred overnight at room temperature and the solvent was removed in vacuo. The resultant oil was partitioned with ethyl acetate and was washed with 10% aqueous potassium hydroxide. The organic was dried over sodium sulfate and was concentrated. (1S)-1-[2-Bromo-5-(trifluoromethyl)phenyl]hex-5-en-1-amine (1.11 g, 3.45 mmol) was carried forward without further purification. MS ESI calc'd. for C₁₃H₁₆BrF₃N [M+H]+ 322.0 and 324.0, found 322.2 and 324.2.

Step 3: To DIPEA (1.81 mL, 10.3 mmol) and (1S)-1-[2-Bromo-5-(trifluoromethyl)phenyl]hex-5-en-1-amine (1.11 g, 3.45 mmol) in DCM (20 mL) was added benzyl chloroformate at 0° C. The reaction was stirred at room temperature for 2 hours and was quenched with water. The organic was washed with 10% aqueous KOH and the aqueous layer was back-extracted with ethyl acetate. The combined organics were dried over sodium sulfate, filtered, concentrated and then purified by column chromatography to benzyl {(1S)-1-[2-bromo-5-(trifluoromethyl)phenyl]hex-5-en-1-yl}carbamate (1.5 g, 3.29 mmol). ¹H NMR (500 MHz, CDCl₃) δ7.71 (m, 1H), 7.69 (s, 1H), 7.39-7.29 (b, 6H), 5.81 (m, 1H), 5.28 (m, 1H), 5.14 (s, 2H), 5.08 (m, 2H), 2.16 (m, 2H), 1.84 (m, 1H), 1.68 (m 1H), 1.59 (m, 1H), 1.51 (m, 1H).

Step 4: To a 100 mL RBF equipped with a reflux condenser was added benzyl {(1S)-1-[2-bromo-5-(trifluoromethyl)phenyl]hex-5-en-1-yl}carbamate (1.5 g, 3.29 mmol), 1-ethenyl-3,5-bis(trifluoromethyl)benzene (1.58 g, 6.57 mmol) and dichloromethane (10 mL). The system was flushed with nitrogen and 1,3-bis(2,4,6-trimethylphenyl)-4,5-dihydroimidazol-2-ylidene[2-(i-propoxy)-5-(N,N-dimethylaminosulfonyl)phenyl]methyleneruthenium(II) dichloride (41 mg, 0.57 mmol) was added before heating at 60° C. for 20 min. The reaction was cooled to room temperature and was directly purified by column chromatography to yield benzyl {(1R,5E)-6-[3,5-bis(trifluoromethyl)phenyl]-1-[2-bromo-5-(trifluoromethyl)phenyl]hex-5-en-1-yl}carbamate (2.0 g, 2.99 mmol). $^1$H NMR (500 MHz, CDCl$_3$) δ7.81 (s, 1H), 7.67 (d, J=8.3 Hz, 1H), 7.37 (d, J=8.1 Hz, 1H), 5.82 (m, 1H), 5.05 (m, 2H), 4.41 (m, 1H), 3.82 (s, 1H), 2.13 (m, 2H), 1.76 (m, 1H), 1.42 (m, 1H).

Step 5: To a 250 mL RBF was added tetrabutylammonium hydrogen sulfate (97 mg, 0.284 mmol), D-Epoxone (370 mg, 1.43 mmol), benzyl {(1R,5E)-6-[3,5-bis(trifluoromethyl)phenyl]-1-[2-bromo-5-(trifluoromethyl)phenyl]hex-5-en-1-yl}carbamate (1.9 g, 2.84 mmol) followed by MeCN (15 mL) and EtOAc (20 mL). Sodium tetraborate decahydrate (1.08 g, 2.84 mmol) in an aqueous ethylenediaminetetraacetic acid disodium salt dihydrate solution (0.4 mM, 7 mL) was added to the reaction at 0° C. A solution of potassium carbonate (3.93 g, 28.4 mmol) in water (25 mL) and a solution of OXONE® (5.24 g, 8.53 mmol) in an aqueous ethylenediaminetetraacetic acid disodium salt dihydrate (0.4 mM, 25 mL) were simultaneously added to the reaction at 0° C. over the course of two hours. An additional solution of D-Epoxone (370 mg, 1.43 mmol) in MeCN (3 mL) was added via syringe pump over 1.5 hours. The reaction was diluted with water (100 mL) and was extracted with ethyl acetate (2×100 mL). The organic was concentrated to yield a white solid that was resubjected to the reaction procedure. Benzyl {(1S,4-{(2S,3S)-3-[3,5-bis(trifluoromethyl)phenyl]oxiran-2-yl}-1-[2-bromo-5-(trifluoromethyl)phenyl]butyl}carbamate (1.5 g, 2.19 mmol) was isolated by column chromatography. $^1$H NMR (500 MHz, CDCl$_3$) δ7.81 (s, 1H), 7.75 (s, 2H), 7.59 (s, 1H), 7.42 (m, 2H), 5.3 (m, 1H), 5.19 (m, 1H), 5.15 (s, 2H), 3.78 (m, 1H), 2.98 (m, 1H), 1.95 (m, 2H), 1.82-1.65 (br s, 2H).

Step 6: To benzyl {(1S)-4-{(2S,3S)-3-[3,5-bis(trifluoromethyl)phenyl]oxiran-2-yl}-1-[2-bromo-5-(trifluoromethyl)phenyl]butyl}carbamate (500 mg, 0.731 mmol) in DMF (2 mL) was added DBU (111 mg, 0.731 mmol). The system was heated to 125° C. for 6 hours. The solvent was removed in vacuo. The reaction was diluted with ethyl acetate and water. The organic was dried over sodium sulfate, filtered and concentrated. The resultant oil was purified by column chromatography to yield (R)-[3,5-bis(trifluoromethyl)phenyl]{(2S,6S)-6-[2-bromo-5-(trifluoromethyl)phenyl]piperidin-2-yl}methanol (280 mg, 0.509 mmol). $^1$H NMR (500 MHz, CDCl$_3$) δ7.9 (s, 2H), 7.81 (d, J=5.4 Hz, 2H), 7.64 (d, J=8.3 Hz, 1H), 7.35 (d, J=8.3 Hz, 1H), 5.14 (d, J=8.2 Hz, 1H), 4.51 (m, 1H), 3.16 (m, 1H), 2.06 (m, 1H), 1.95 (m, 1H), 1.80 (m, 2H), 1.62 (m, 1H), 1.29 (m, 1H).

Step 7: To (R)-[3,5-bis(trifluoromethyl)phenyl]{(2S,6S)-6-[2-bromo-5-(trifluoromethyl)phenyl]piperidin-2-yl}methanol (280 mg, 0.509 mmol) in DCM (5 mL) was added DIPEA (0.9 mL, 0.509 mmol) and phosgene (252 mg, 0.509 mmol). The reaction mixture was stirred at room temperature for 30 minutes before the solvent was removed and the reaction was diluted with ethyl acetate (15 mL) and aqueous KOH (15 mL). The organic was dried over sodium sulfate, filtered, and concentrated before purification by preparative TLC to yield (1R,5S,8aS)-5-[2-bromo-5-(trifluoromethyl)phenyl]-1-[3-methyl-5-(trifluoromethyl)phenyl]hexahydro[1,3]oxazolo[3,4-a]pyridin-3-one (200 mg, 0.347 mmol). MS ESI calc'd. for C$_{22}$H$_{16}$BrF$_9$NO$_2$ [M+H]+ 576.0 and 578.0, found 576.1 and 578.1.

Scheme E

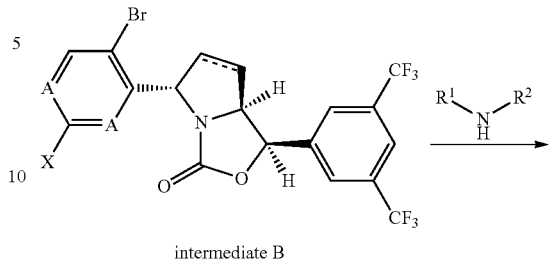

intermediate B

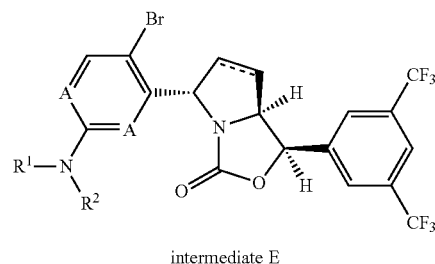

intermediate E

Preparation of Intermediate E is carried out via displacement of an appropriately functionalized Intermediate B/D by a commercially available amine.

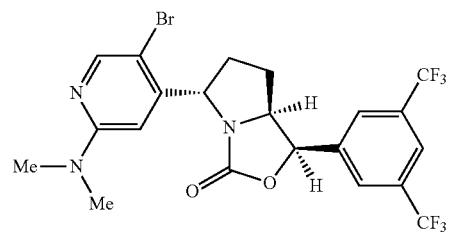 [SMILES: CN(C)c1cc([C@@H]2CC[C@H]3[C@@H](c4cc(C(F)(F)F)cc(C(F)(F)F)c4)OC(=O)N23)c(Br)cn1]

Intermediate E1

(1R,5S,7aS)-1-[3,5-bis(trifluoromethyl)phenyl]-5-[5-bromo-2-(dimethylamino)pyridin-4-yl]tetrahydro-1H-pyrrolo[1,2-c][1,3]oxazol-3-one To Intermediate B4 (130 mg, 0.245 mmol) in THF (0.5 mL) was added dimethylamine (2.0 M, 3.7 mL, 7.4 mmol). The system was sealed and heated to 150° C. by microwave irradiation for 1 hour. The reaction was then directly purified by HPLC to yield (1R,5S,7aS)-1-[3,5-bis(trifluoromethyl)phenyl]-5-[5-bromo-2-(dimethylamino)pyridin-4-yl]tetrahydro-1H-pyrrolo[1,2-c][1,3]oxazol-3-one (80 mg, 0.149 mmol). MS ESI calc'd. for C$_{21}$H$_{19}$BrF$_6$N$_3$O$_2$ [M+H]+ 538.0 and 540.0, found 538.0 and 540.0.

The following intermediates in Table 3 were prepared according to Scheme E using the procedure outlined in the synthesis of Intermediate E1.

TABLE 3

| Int | Structure | IUPAC Name | Exact Mass [M + H]+ |
|---|---|---|---|
| E2 | 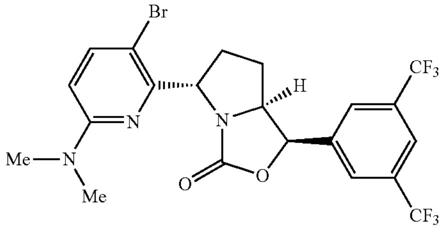 [SMILES: CN(C)c1ccc(Br)c([C@@H]2CC[C@H]3[C@@H](c4cc(C(F)(F)F)cc(C(F)(F)F)c4)OC(=O)N23)n1] | (1R,5S,7aS)-1-[3,5-bis(trifluoromethyl)phenyl]-5-[3-bromo-6-(dimethylamino)pyridin-2-yl]tetrahydro-1H-pyrrolo[1,2-c][1,3]oxazol-3-one | Calc'd 538.1 and 540.1, found 538.0 and 540.0 |
| E3 | 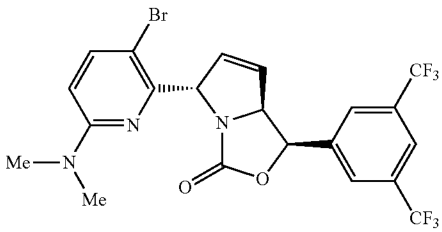 [SMILES: CN(C)c1ccc(Br)c([C@@H]2C=C[C@H]3[C@@H](c4cc(C(F)(F)F)cc(C(F)(F)F)c4)OC(=O)N23)n1] | (1R,5S,7aS)-1-[3,5-bis(trifluoromethyl)phenyl]-5-[3-bromo-6-(dimethylamino)pyridin-2-yl]-5,7a-dihydro-1H-pyrrolo[1,2-c][1,3]oxazol-3-one | Calc'd 536.0 and 538.0, 536.1 and 538.1 |
| E4 | 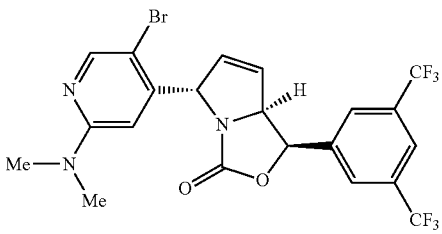 [SMILES: CN(C)c1cc([C@@H]2C=C[C@H]3[C@@H](c4cc(C(F)(F)F)cc(C(F)(F)F)c4)OC(=O)N23)c(Br)cn1] | (1R,5S,7aS)-1-[3,5-bis(trifluoromethyl)phenyl]-5-[5-bromo-2-(dimethylamino)pyridin-4-yl]-5,7a-dihydro-1H-pyrrolo[1,2-c][1,3]oxazol-3-one | Calc'd 536.0 and 538.0, 536.2 and 538.2 |

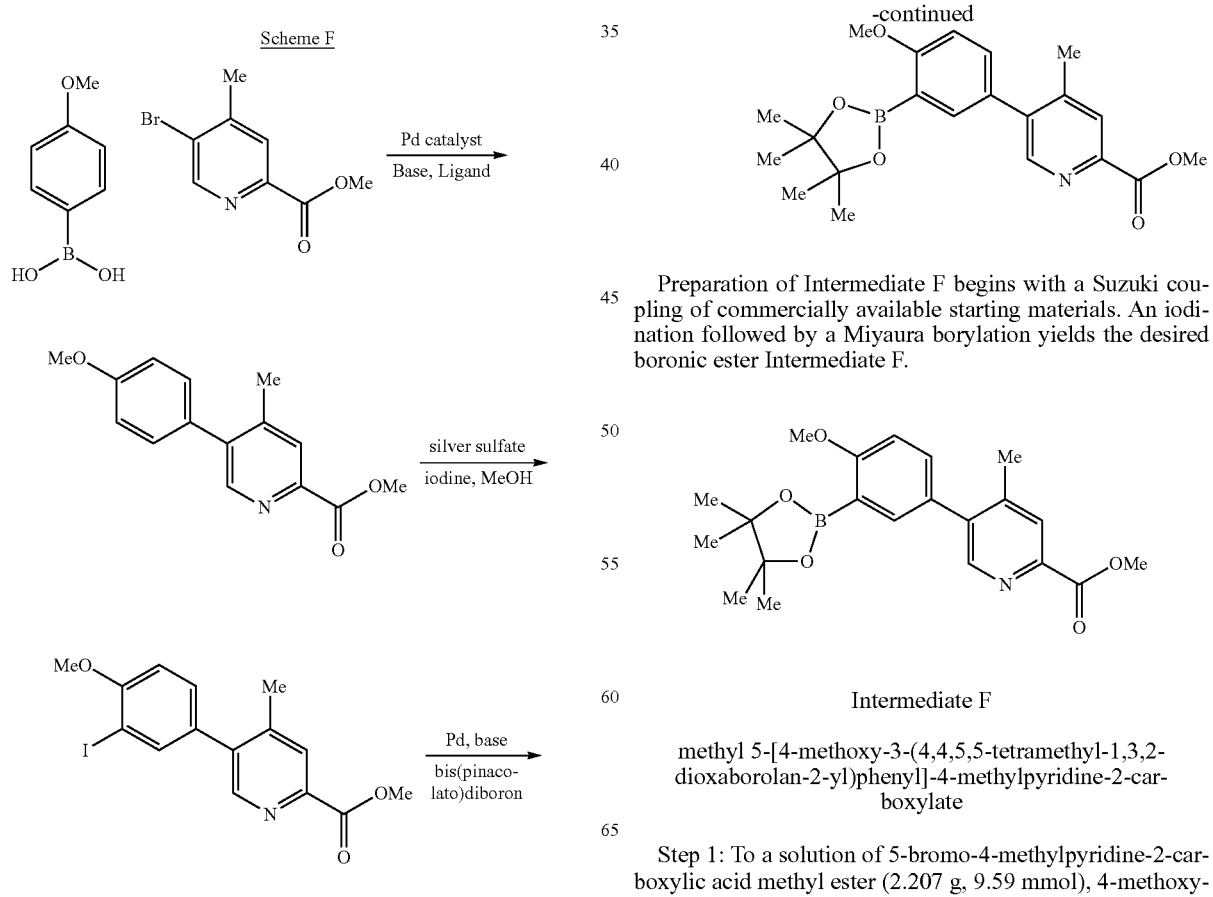

Preparation of Intermediate F begins with a Suzuki coupling of commercially available starting materials. An iodination followed by a Miyaura borylation yields the desired boronic ester Intermediate F.

Intermediate F methyl 5-[4-methoxy-3-(4,4,5,5-tetramethyl-1,3,2-dioxaborolan-2-yl)phenyl]-4-methylpyridine-2-carboxylate Step 1: To a solution of 5-bromo-4-methylpyridine-2-carboxylic acid methyl ester (2.207 g, 9.59 mmol), 4-methoxylphenylboronic acid (1.604 g, 10.55 mmol) and 1,1'-bis(ditert-butylphosphino)ferrocene palladium dichloride (0.313 g, 0.480 mmol) in THF (30 mL) was added potassium carbonate (2.0 M in water, 10.1 mL, 20.15 mmol). The mixture was purged with nitrogen and heated at 50° C. for 1 hour and at 60° C. for 5 hours. The reaction was poured into ethyl acetate and was washed with brine, dried over sodium sulfate, filtered and concentrated. It was purified by column chromatography to yield methyl 5-(4-methoxyphenyl)-4-methylpyridine-2-carboxylate (2.47 g, 9.59 mmol) as a pink solid. MS ESI calc'd. for $C_{15}H_{16}NO_3$ [M+H]+ 258.1, found 258.1.

Step 2: A suspension of iodine (2.45 g, 9.66 mmol), silver sulfate (3.01 g, 9.66 mmol) and methyl 5-(4-methoxyphenyl)-4-methylpyridine-2-carboxylate (2.47 g, 9.59 mmol) in MeOH (20 mL) was stirred at room temperature for 3.5 hours. It was then heated at 36° C. for 4 hours and then at room temperature for another 16 hours. Additional iodine (0.8 g, 3.15 mmol) and silver sulfate (1 g, 3.2 mmol) were added and the reaction was heated to 36° C. for 3 hours. The volatiles were removed and the reaction was diluted with ethyl acetate and aqueous sodium thiosulfate. The organic was washed with brine, dried over sodium sulfate, filtered and then concentrated. The resultant oil was purified by column chromatography to yield methyl 5-(3-iodo-4-methoxyphenyl)-4-methylpyridine-2-carboxylate (2.35 g, 6.12 mmol) as a white solid. MS ESI calc'd. for $C_{15}H_{15}INO_3$ [M+H]+ 384.0, found 384.0.

Step 3: A solution of [1,1'-bis(diphenylphosphino)ferrocene]dichloropalladium(II) (0.368 g, 0.451 mmol), potassium acetate (1.34 g, 13.6 mmol), bis(pinacolato)diboron (1.4 g, 5.50 mmol) and methyl 5-(3-iodo-4-methoxyphenyl)-4-methylpyridine-2-carboxylate (1.73 g, 4.51 mmol) in DMSO (20 mL) was heated at 80° C. for 80 minutes. The mixture was cooled to room temperature and was poured into ethyl acetate and water. The organic was washed with brine, dried over sodium sulfate, filtered and concentrated. The crude oil was purified by column chromatography to yield methyl 5-[4-methoxy-3-(4,4,5,5-tetramethyl-1,3,2-dioxaborolan-2-yl)phenyl]-4-methylpyridine-2-carboxylate (1.73 g, 4.51 mmol). MS ESI calc'd. for $C_{21}H_{26}BNO_5$ [M+H]+ 384.2, found 384.2.

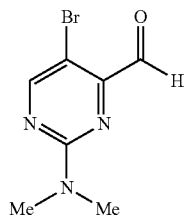

Intermediate G 5-bromo-2-(dimethylamino)pyrimidine-4-carbaldehyde

Step 1: To [5-bromo-2-(methylsulfanyl)pyrimidin-4-yl]methanol (20 g, 85 mmol) in DCM (100 mL) was added m-CPBA (41.9 g, 187 mmol) portionwise at room temperature. The reaction was stirred for 1 hour before dimethylamine (2.0 M, 213 mL, 425 mmol) was added. After 2 hours, additional dimethylamine (2.0 M, 40 mL, 80 mmol) was added and the reaction was stirred overnight. The volatiles were removed and the crude oil was dissolved in ethyl acetate, washed with water and then brine, dried over magnesium sulfate, filtered and concentrated. [5-Bromo-2-(dimethylamino)pyrimidin-4-yl]methanol (19 g, 82 mmol) was carried forward as a crude oil. $^1$H NMR (500 MHz, CDCl$_3$) δ 8.29 (s, 1H), 4.60 (s, 2H), 3.22 (s, 6H).

Step 2: To [5-bromo-2-(dimethylamino)pyrimidin-4-yl]methanol (19 g, 82 mmol) in DCM (10 mL) was added Dess-Martin periodinane (41.7 g, 98 mmol) at room temperature. The reaction was stirred overnight and the reaction was diluted with hexanes, filtered and was concentrated before purification by column chromatography to yield 5-bromo-2-(dimethylamino)pyrimidine-4-carbaldehyde (10 g, 43.5 mmol). $^1$H NMR (500 MHz, CDCl$_3$) δ 9.95 (s, 1H), 8.52 (s, 1H), 3.24 (s, 6H).

Scheme G

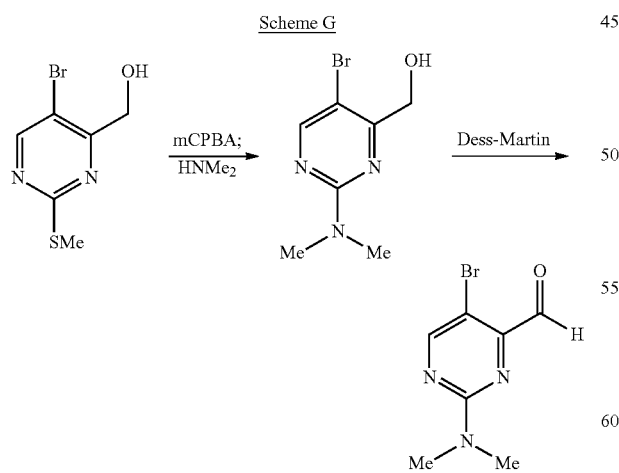

Preparation of Intermediate G was carried out with oxidation of a methylsulfide followed by displacement with dimethylamine. Subsequent oxidation of the alcohol yields the aldehyde Intermediate G.

Scheme H

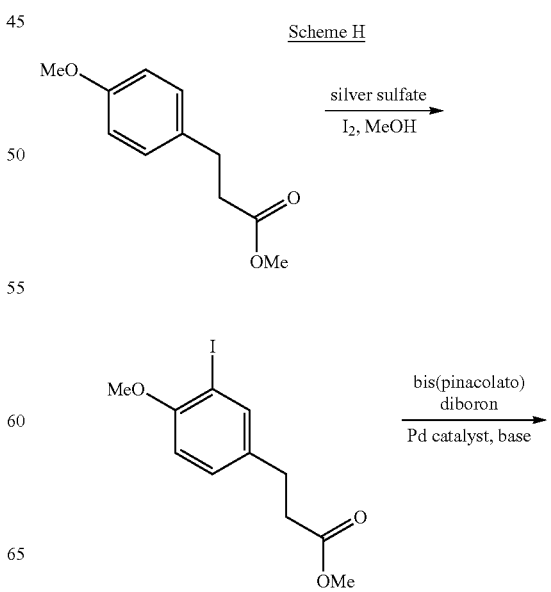

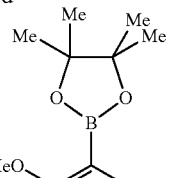

Intermediate H was prepared via iodination and subsequent Miyaura borylation from commercially available starting materials.

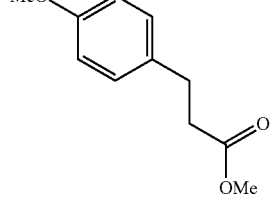

Intermediate H methyl 3-[4-methoxy-3-(4,4,5,5-tetramethyl-1,3,2-dioxaborolan-2-yl)phenyl]propanoate Step 1: A 3-neck 5 L RBF equipped with mechanical stirrer, thermometer, and a nitrogen bubbler, was charged with 3-(4-methoxyphenyl)propionic acid methyl ester (100 g, 515 mmol), silver sulfate (161 g, 515 mmol) and iodine (131 g, 515 mmol) in methanol (2 L). The reaction mixture was stirred vigorously at room temperature for 1 hour. The reaction was filtered through Solka-Floc® (ethyl acetate wash). The filtrate was concentrated and the residue was taken up in ethyl acetate (4 L). The organic was washed with water, saturated aq. NaHSO$_3$ (50 mL), and brine (50 mL) before drying over Na$_2$SO$_4$, filtering, and concentrating to dryness. The crude reaction was purified by column chromatography to yield methyl 3-(3-iodo-4-methoxyphenyl)propanoate (155 g, 484 mmol) as a clear oil. MS ESI calc'd. for C$_{11}$H$_{14}$IO$_3$ [M+H]+ 321.0, found 321.0.

Step 2: A 3-neck 12 L RBF equipped with mechanical stirrer, thermometer, nitrogen bubbler, condenser and addition funnel, was charged with methyl 3-(3-iodo-4-methoxyphenyl)propanoate (155 g, 484 mmol), bis(pinacolato)diboron (154 g, 605 mmol), and potassium acetate (95 g, 48.4 mmol) in DMSO (3 L) and dioxane (0.9 L). The system was degassed three times with nitrogen gas before the addition of dichloro[1,1'-bis(diphenylphosphino)ferrocene]palladium (II) dichloromethane adduct (39.5 g, 48.4 mmol). The system was degassed three times and was then heated to 50° C. for 1 hour. The temperature was raised to 80° C. and the reaction was stirred overnight. The reaction was diluted with ethyl acetate (4 L) and was partitioned with water and then with brine. The organic was dried over MgSO$_4$, filtered, and concentrated in vacuo. The crude reaction was purified by column chromatography to yield methyl 3-[4-methoxy-3-(4,4,5,5-tetramethyl-1,3,2-dioxaborolan-2-yl)phenyl]propanoate (108.1 g, 338 mmol) as a tan solid. MS ESI calc'd. for C$_{17}$H$_{26}$BO$_5$ [M+H]+ 321.2, found 321.2.

Scheme I

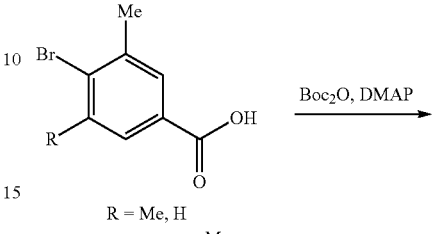

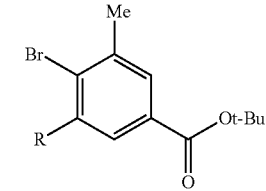

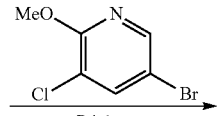

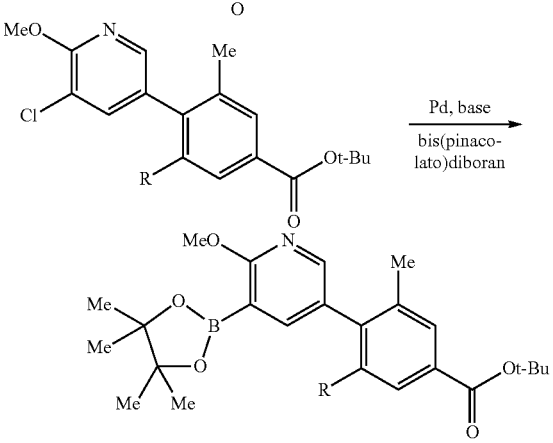

R = Me, H

Preparation of Intermediate I begins with formation of a tert-butyl ester which is then subjected to a Miyuara coupling to obtain the corresponding boronic ester. Suzuki coupling with a commercially available 5-bromo-3-chloro-2-methoxypyridine yields the coupled chloride. A second Miyaura coupling provides the desired boronic ester Intermediate I.

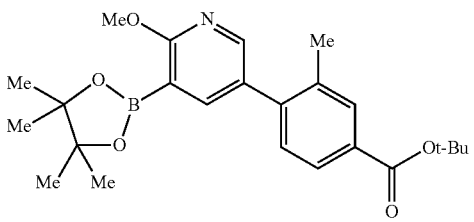 [SMILES: COc1ncc(-c2ccc(C(=O)OC(C)(C)C)cc2C)cc1B1OC(C)(C)C(C)(C)O1]

Intermediate I tert-butyl 4-[6-methoxy-5-(4,4,5,5-tetramethyl-1,3,2-dioxaborolan-2-yl)pyridin-3-yl]-3-methylbenzoate Step 1: To a 250 mL RBF was added 4-bromo-3-methylbenzoic acid (10 g, 46.5 mmol), DMAP (8.52 g, 69.8 mmol) and tert-butyl alcohol (100 mL). Di-tert-butyl dicarbonate (12.96 mL, 55.8 mmol) was added via a syringe to the solution, which caused vigorous bubbling, foaming and the loss of some material. The remaining reaction mixture was heated at 70° C. overnight. The reaction was cooled to room temperature and the volatiles were removed under reduced pressure. Crude material was diluted with ethyl acetate:hexanes (1:4, 200 mL) and was washed sequentially with 5% aqueous KOH (200 mL) and saturated aqueous ammonium chloride (2×100 mL). The organics were dried over sodium sulfate, filtered and concentrated before purification by column chromatography. tert-Butyl 4-bromo-3-methylbenzoate was isolated as a colorless oil (7.2 g, 26.6 mmol). $^1$H NMR (500 MHz, CDCl$_3$) δ 7.87 (s, 1H), 7.67 (d, J=8.3 Hz, 1H), 7.60 (d, J=8.2 Hz, 1H), 2.47 (s, 3H), 1.62 (s, 9H).

Step 2: To a 250 mL RBF was added 1,1'-bis(di-tert-butylphosphino)ferrocene palladium dichloride (0.317 g, 0.487 mmol), tert-butyl 4-bromo-3-methylbenzoate (6.6 g, 24.34 mmol), bis(pinacolato)diboron (7.42 g, 29.2 mmol), potassium acetate (5.97 g, 60.9 mmol) and dioxane (25 mL). The system was flushed with nitrogen and was heated at 125° C. overnight. The reaction was cooled to room temperature and was diluted with ethyl acetate:hexanes (1:9, 120 mL) and then was washed sequentially with water (150 mL) and then brine (50 mL). The organics were dried over sodium sulfate, filtered and concentrated before purification by column chromatography. tert-Butyl 3-methyl-4-(4,4,5,5-tetramethyl-1,3,2-dioxaborolan-2-yl)benzoate was isolated as a crystalline solid (6.6 g, 14.5 mmol). $^1$H NMR indicated it is about 70% pure. $^1$H NMR (500 MHz, CDCl$_3$) δ 7.8 (m, 3H), 2.60 (s, 3H), 1.58 (s, 9H), 1.39 (s, 12H).

Step 3: To a 250 mL RBF was added 5-bromo-3-chloro-2-methoxypyridine (1.5 g), tribasic potassium phosphate (2.86 g, 13.5 mmol), bis(diphenylphosphino)ferrocene]palladium(II) dichloromethane adduct (0.275 g, 6.74 mmol), tert-butyl 3-methyl-4-(4,4,5,5-tetramethyl-1,3,2-dioxaborolan-2-yl)benzoate (2.27 g, 7.13 mmol), dioxane (50 mL) and water (3 mL). The flask was sealed and was stirred at 80° C. overnight. The reaction was cooled to room temperature, diluted with ethyl acetate, washed with water, filtered and concentrated. The resultant residue was purified by column chromatography to yield tert-butyl 4-(5-chloro-6-methoxypyridin-3-yl)-3-methylbenzoate (2.0 g, 5.99 mmol). MS ESI calc'd. for C$_{18}$H$_{21}$ClNO$_3$ [M+H]+ 334.1, found 334.0.

Step 4: To a 250 mL RBF was added tert-butyl 4-(5-chloro-6-methoxypyridin-3-yl)-3-methylbenzoate (4.5 g, 13.5 mmol), bis(pinacolato)diboron (6.85 g, 27.0 mmol), potassium acetate (3.97 g, 40.4 mmol), and chloro(2-dicyclohexylphosphino-2',4',6'-triisopropyl-1,1'-biphenyl)[2-(2'-amino-1,1'-biphenyl)]palladium(II) (0.212 g, 0.27 mmol) followed by anhydrous dioxane (50 mL). The system was evacuated and backfilled with nitrogen (3×) and was heated to 120° C. for 2 hours. The mixture was cooled, filtered over Celite (ethyl acetate wash) and was concentrated. The residue was purified by column chromatography to afford tert-butyl 4-[6-methoxy-5-(4,4,5,5-tetramethyl-1,3,2-dioxaborolan-2-yl)pyridin-3-yl]-3-methylbenzoate as a solid (4.3 g, 10.11 mmol). MS ESI calc'd. for C$_{24}$H$_{33}$BNO$_5$ [M+H]+ 426.2, found 426.0.

Scheme J

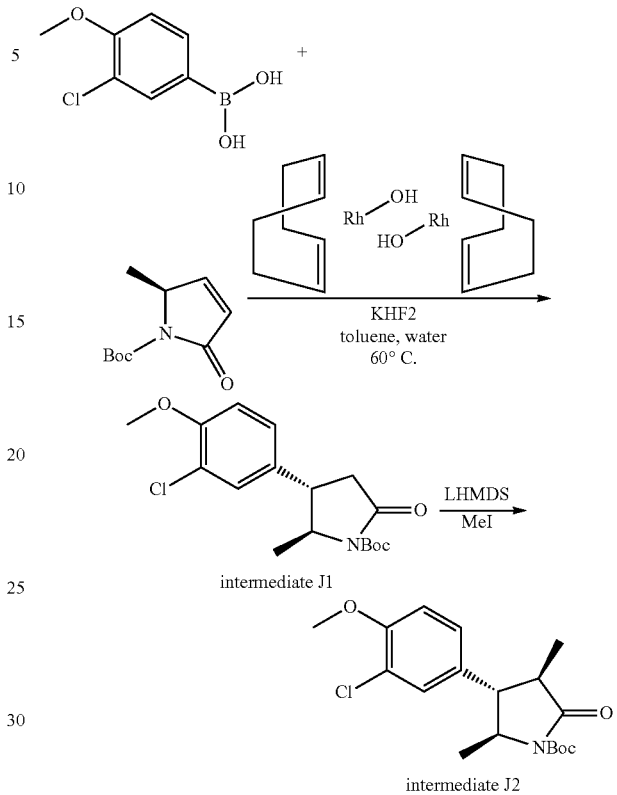

intermediate J1 intermediate J2

Intermediate J1 was synthesized by rhodium catalyzed Michael addition of appropriate boronic acids to the known pyrrolinone derivative, (S)-tert-butyl 2-methyl-5-oxo-2,5-dihydro-1H-pyrrole-1-carboxylate (Cuiper et al., *J. Org. Chem.* 1999, 64, 2567-2570). Treatment of J1 with strong base, followed by trapping of the in situ generated enolate with MeI afforded intermediate J2. The enantiomer of J2 was synthesized following the same procedure starting from (R)-tert-butyl 2-methyl-5-oxo-2,5-dihydro-1H-pyrrole-1-carboxylate.

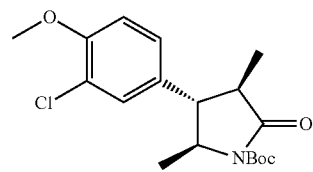 [SMILES: COc1ccc([C@@H]2[C@@H](C)C(=O)N(C(=O)OC(C)(C)C)[C@H]2C)cc1Cl]

Intermediate J2

(2S,3S,4R)-tert-butyl 3-(3-chloro-4-methoxyphenyl)-2,4-dimethyl-5-oxopyrrolidine-1-carboxylate Step 1: To a 100 mL RBF were added (3-chloro-4-methoxyphenyl)boronic acid (1.89 g, 10.14 mmol), (S)-tert-butyl 2-methyl-5-oxo-2,5-dihydro-1H-pyrrole-1-carboxylate (1 g, 5.07 mmol), hydroxy(cyclooctadiene)rhodiumRhodium(I) dimer (0.116 g, 0.254 mmol), potassium hydrogen fluoride (1.58 g, 20.28 mmol). The mixture was degassed and filled back with N$_2$. Dioxane (45 mL) and water (5 mL) were then added. The mixture was degassed again and filled with N₂. The reaction mixture was heated at 60° C. overnight. It was diluted with EtOAc (200 mL), washed with water, brine. Organic layer was dried over Na₂SO₄, and concentrated. The residue was purified by silica gel chromatography, eluted with 30% EtOAc/Hexane to give (2S,3S)-tert-butyl 3-(3-chloro-4-methoxyphenyl)-2-methyl-5-oxopyrrolidine-1-carboxylate (intermediate J1, 0.85 g) as white crystalline solid. ¹H NMR (500 MHz, CDCl₃): δ 7.20 (s, 1H), 7.05 (d, 1H), 6.87 (d, 1H), 4.08 (m, 1H), 3.86 (s, 3H), 2.95 (m, 2H), 2.53 (m, 1H), 1.52 (s, 9H), 1.41 (d, 3H).

Step 2: To a solution of (2S,3S)-tert-butyl 3-(3-chloro-4-methoxyphenyl)-2-methyl-5-oxopyrrolidine-1-carboxylate (intermediate J1, 0.85 g, 2.5 mmol) in THF (20 mL) was added LiHMDS (2.5 mL, 2.5 mmol) at −78° C. After 30 mins, MeI (0.187 mL, 3.00 mmol) was added. The reaction mixture was stirred at −78° C. for 1.5 hr. It was warmed up to 0° C. for 30 min and then warmed up to RT for 30 min. The reaction mixture was quenched with 2 mL of AcOH and 100 mL of NH₄Cl. The product was extracted with EtOAc (3×100 mL). The organic layer was washed with brine (100 mL), dried over Na₂SO₄ and concentrated. The residue was purified by silica gel chromatography, eluted with 30% EtOAc/Hexane to give (2S,3S,4R)-tert-butyl 3-(3-chloro-4-methoxyphenyl)-2,4-dimethyl-5-oxopyrrolidine-1-carboxylate (intermediate J2, 0.55 g, yield of 62%) as off-white solid. ¹H NMR (500 MHz, CDCl₃): δ 7.29 (s, 1H), 7.14 (d, 1H), 6.95 (d, 1H), 3.93 (s, 3H), 3.91 (m, 1H), 2.58 (m, 1H), 2.40 (m, 1H), 1.59 (s, 9H), 1.38 (d, 3H), 1.17 (d, 3H).

Scheme K

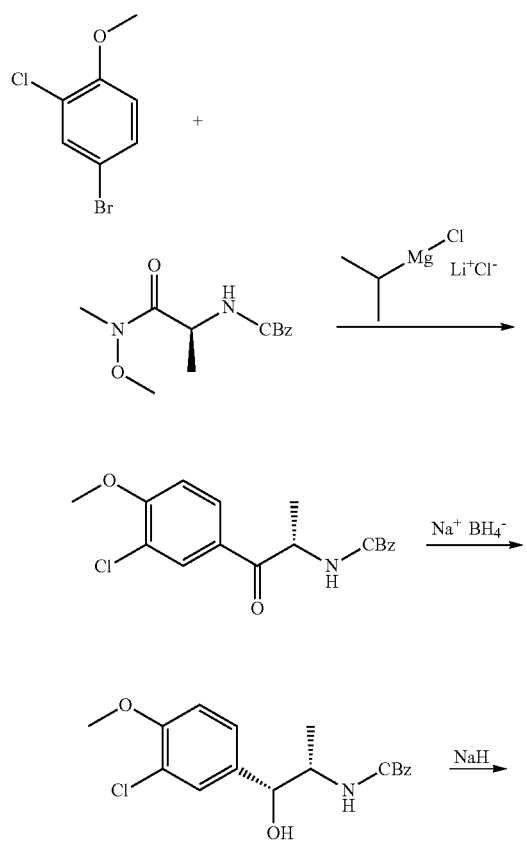

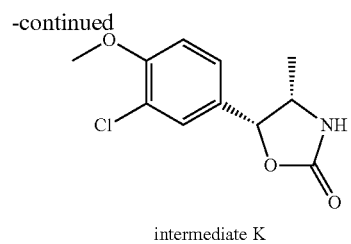

intermediate K

Intermediate K (4S,5R)-5-(3-chloro-4-methoxyphenyl)-4-methyloxazolidin-2-one

Step 1. A solution of 4-bromo-2-chloroanisole (3 g, 13.55 mmol) and (S)-benzyl (1-(methoxy(methyl)amino)-1-oxopropan-2-yl)carbamate (3.79 g, 14.22 mmol) in THF (33.9 mL) was cooled to −20° C. with dry ice/acetone. To this solution was added isopropylmagnesium chloride lithium chloride complex (22.9 mL, 29.8 mmol) at −20° C. dropwise under N₂. After addition, the reaction mixture was warmed up to rt and stirred overnight. The reaction mixture was cooled to −40° C. and slowly poured into a stirred mixture of crushed ice and 30 mL of 1N HCl. The resulting mixture was diluted with 30 mL of brine, extracted with EtOAc (3×50 mL). The organic layer was dried with Na₂SO₄ and concentrated. The residue was purified by silica gel chromatography, eluted with 0-100% EtOAc in hexane to give (S)-benzyl (1-(3-chloro-4-methoxyphenyl)-1-oxopropan-2-yl)carbamate (0.82 g) as a white solid. ¹H NMR (500 MHz, CDCl₃): δ 8.05 (s, 1H), 7.92 (d, 1H), 6.98 (d, 1H), 5.93 (d, 1H), 5.29 (m, 1H), 5.16 (s, 2H), 3.99 (s, 3H), 1.43 (d, 3H).

Step 2. To a solution of (S)-benzyl (1-(3-chloro-4-methoxyphenyl)-1-oxopropan-2-yl)carbamate (0.81 g, 2.456 mmol) in MeOH (10 mL) and THF (10 mL) was added NaBH₄ (0.139 g, 3.68 mmol) at 0° C. The solution was stirred at that temperature for 0.5 hr. The reaction was quenched with Saturated NH₄Cl aq. solution (20 mL) and water (20 mL). The mixture was extracted 3 times with EtOAc (100 mL). The organic layer was washed with brine, dried with Na₂SO₄ and concentrated. The residue was purified by chromatography over silica gel and eluted with 40% EtOAc in hexane to give two isomers. The major isomer is benzyl ((1R,2S)-1-(3-chloro-4-methoxyphenyl)-1-hydroxypropan-2-yl)carbamate (0.41 g). ¹H NMR (500 MHz, CDCl₃): δ 7.28 (s, 1H), 7.20 (d, 1H), 6.89 (d, 1H), 5.17 (s, 2H), 5.02 (d, 1H), 4.81 (d, 1H), 4.03 (b, 1H), 3.93 (s, 3H), 1.01 (d, 3H).

Step 3. To a solution of benzyl ((1R,2S)-1-(3-chloro-4-methoxyphenyl)-1-hydroxypropan-2-yl)carbamate (0.24 g, 0.686 mmol) in THF (4.6 mL) was added NaH (0.036 g, 0.892 mmol) at 0° C. The reaction mixture was warmed to RT and stirred overnight. It was then quenched with 1N HCl (1.5 mL). This mixture was diluted with EtOAc and washed with sat. aqueous NaHCO₃, water and brine. The organic phase was dried with Na₂SO₄ and concentrated. The residue was purified by silica gel chromatography, eluted with EtOAc to give (4S,5R)-5-(3-chloro-4-methoxyphenyl)-4-methyloxazolidin-2-one (intermediate K, 0.13 g). ¹H NMR (500 MHz, CDCl₃): δ 7.37 (s, 1H), 7.21 (d, 1H), 6.97 (d, 1H), 5.84 (b, 1H), 5.65 (d, 1H), 4.21 (m, 1H), 3.96 (s, 3H), 0.87 (d, 3H).

Scheme L

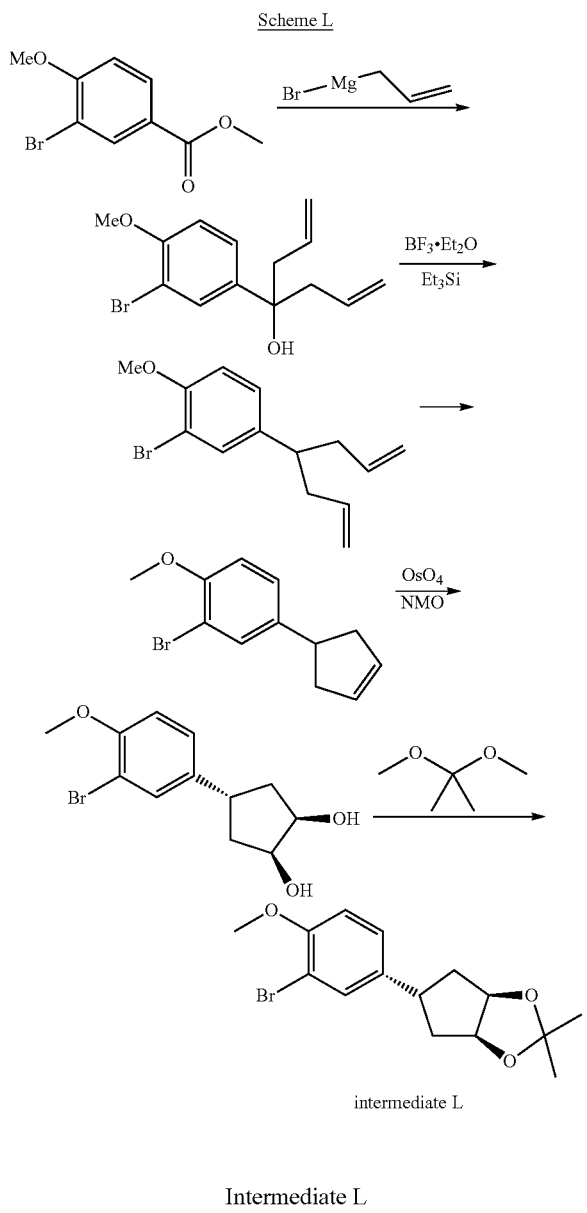

intermediate L

Intermediate L (3aR,5s,6aS)-5-(3-bromo-4-methoxyphenyl)-2,2-dimethyltetrahydro-3aH-cyclopenta[d][1,3]dioxole Step 1: To a 250 mL RBF was added methyl 3-bromo-4-methoxybenzoate (4.0 g, 16.3 mmol). The flask was flushed with $N_2$. THF (60 mL) was added, followed by allylmagnesium bromide (39.2 mL, 39.2 mmol, 1.0 M in ether) at 0° C. via a syringe over 10 mins. The resulting reaction mixture was stirred at 0° C. for 2 hrs. It was quenched by addition of 50 mL sat. $NH_4Cl$ at 0° C. and 100 mL of water. The product was extracted with EtOAc (3×100 mL). Organics were washed with 100 mL brine, dried over sodium sulfate, filtered, and concentrated to give 4-(3-bromo-4-methoxyphenyl)hepta-1,6-dien-4-ol (5.0 g) as a colorless oil. $^1$H NMR (500 MHz, $CDCl_3$:) δ 7.61 (s, 1H), 7.30 (d, 1H), 6.88 (d, 1H), 5.63 (m, 2H), 5.12 (d, 4H), 3.93 (s, 3H), 2.65 (m, 2H), 2.53 (m, 2H).

Step 2: To a 250 mL RBF were added 4-(3-bromo-4-methoxyphenyl)hepta-1,6-dien-4-ol (4.85 g, 16.32 mmol), triethylsilane (5.21 mL, 32.6 mmol), and $CH_2Cl_2$ (50 mL). The flask was flushed with $N_2$. $BF_3 \cdot Et_2O$ (2.275 mL, 17.95 mmol) was added via syringe at −78° C. The resulting reaction mixture was stirred at −78° C. for 1 hr and was then allowed to warm to 0° C. briefly. 50 mL 10% KOH was added at 0° C. and the reaction mixture was extracted with 50 mL EtOAc/Hexane (1:1). The organics were washed with 30 mL brine, dried over sodium sulfate, filtered and concentrated. Crude product was purified by silica gel chromatography, eluted with 10% EtOAc/Hexane to give 2-bromo-4-(hepta-1,6-dien-4-yl)-1-methoxybenzene (3.6 g) as colorless oil. $^1$H NMR (500 MHz, $CDCl_3$:) δ 7.38 (s, 1H), 7.06 (d, 1H), 6.85 (d, 1H), 5.66 (m, 2H), 4.99 (d, 4H), 3.91 (s, 3H), 2.66 (m, 1H), 2.42 (m, 2H), 2.33 (m, 2H).

Step 3: To a solution of 2-bromo-4-(hepta-1,6-dien-4-yl)-1-methoxybenzene (2.0 g, 7.11 mmol) in DCM (36 mL) was added Zhan catalyst (47 mg). The mixture was flushed with $N_2$ and refluxed at 45° C. overnight. The reaction mixture was concentrated and the residue was purified by silica gel chromatography, eluting with 10% of EtOAc/isohexane to give 2-bromo-4-(cyclopent-3-en-1-yl)-1-methoxybenzene (1.9 g) as a colorless oil. $^1$H NMR (500 MHz, $CDCl_3$:) δ 7.46 (s, 1H), 7.18 (d, 1H), 6.83 (d, 1H), 5.80 (s, 2H), 3.91 (s, 3H), 3.40 (m, 1H), 2.81 (m, 2H), 2.40 (m, 2H).

Step 4: To a 100 mL RBF were added 2-bromo-4-(cyclopent-3-en-1-yl)-1-methoxybenzene (1.9 g, 7.51 mmol), NMO (2.64 g, 22.5 mmol), osmium tetroxide (0.942 mL, 0.075 mmol, 2.5% in t-BuOH), t-butanol (13 mL) and water (13 mL). The resulting reaction mixture was stirred at rt over the weekend. Volatiles were removed. Crude material was dissolved in 100 mL EtOAc and washed with 50 mL water. Organics were dried over sodium sulfate, filtered and concentrated. The residue was purified by silica gel column chromatography, eluting with 80% EtOAc in hexane to give 4-(3-bromo-4-methoxyphenyl)cyclopentane-1,2-diol (1.7 g) as white solid. $^1$H NMR (500 MHz, $CDCl_3$): δ 7.39 (s, 1H), 7.10 (d, 1H), 6.85 (d, 1H), 4.37 (m, 2H), 3.91 (s, 3H), 3.55 (m, 1H), 2.46 (b, 2H), 2.18 (m, 2H), 1.88 (m, 2H).

Step 5: To a solution of 4-(3-bromo-4-methoxyphenyl)cyclopentane-1,2-diol (2.0 g, 6.97 mmol) in acetone (50 mL) was added 2,2-dimethoxypropane (2.56 mL, 20.90 mmol) at 0° C. followed by adding methanesulfonic acid (0.167 g, 1.74 mmol) dropwise. The reaction mixture was stirred at RT overnight. Volatiles were removed under vacuum. To the residue was added aqueous $NaHCO_3$, and the resulting mixture was extracted with EtOAc. The combined organics were washed with brine, dried over $Na_2SO_4$, filtered and concentrated. Crude product was purified by silica gel column chromatography, eluting with 15% EtOAc in hexane to give intermediate L (1.7 g) as a white solid. $^1$H NMR (500 MHz, $CDCl_3$): δ 7.43 (s, 1H), 7.15 (d, 1H), 6.85 (d, 1H), 4.76 (d, 2H), 3.88 (s, 3H), 3.34 (m, 1H), 2.20 (dd, 2H), 1.59 (m, 2H), 1.55 (s, 3H), 1.35 (s, 3H).

Scheme M

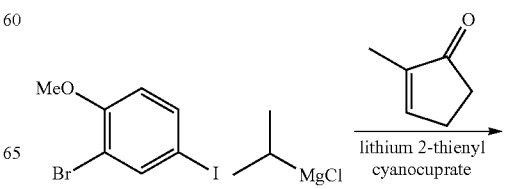

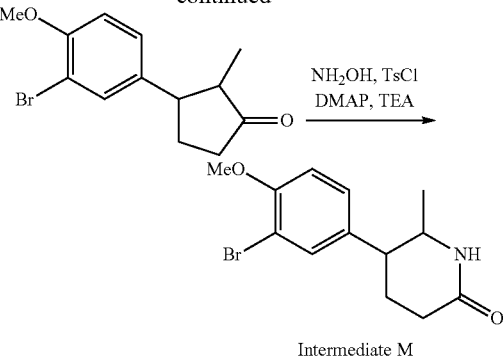

Intermediate M

Intermediate M was synthesized by Michael addition of the appropriate aryl cuperate reagent to 2-methylcyclopent-2-enone, followed by a Beckmann rearrangement.

Intermediate M 5-(3-bromo-4-methoxyphenyl)-6-methylpiperidin-2-one

Step 1: To a 100 mL RBF was added 2-bromo-4-iodo-1-methoxybenzene (0.59 g, 1.87 mmol), and 10 mL THF. iPrMgCl (0.94 mL, 1.89 mmol, 2M THF solution) was added at 0° C. via syringe. The reaction mixture was stirred at 0° C. for 1 hr. A solution of lithium 2-thenyl cyanocuprate (7.5 mL, 1.87 mmol) in THF was added, followed by 2-methylcyclopent-2-enone (150 mg, 1.56 mmol). The resulting reaction mixture was stirred at 0° C. for 1 hr and was allowed to warm up and stirred at rt for 1 hr. The reaction mixture was diluted with 30 mL EtOAc/hexane (1:1), washed with 30 mL 1N HCl, then 20 mL brine. Organics were dried over sodium sulfate, filtered and concentrated. Crude product was purified by silica gel chromatography to give 135 mg 3-(3-bromo-4-methoxyphenyl)-2-methylcyclopentanone as a mixture of two diastereomers at 1.6:1 ratio. $^1$H NMR for the major diastereomer (500 MHz, CDCl$_3$): δ 7.35 (d, J=2.2 Hz, 1H), 7.05 (dd, J=2.2, 8.4 Hz, 1H), 6.89 (d, J=8.4 Hz, 1H), 3.92 (s, 3H), 3.55 (m, 1H), 2.2-2.6 (m, 5H), 0.83 (d, J=7.6 Hz, 3H). $^1$H NMR for the minor diastereomer (500 MHz, CDCl$_3$): δ 7.48 (d, J=2.1 Hz, 1H), 7.19 (dd, J=2.2, 8.3 Hz, 1H), 6.93 (d, J=8.3 Hz, 1H), 3.94 (s, 3H), 2.75 (m, 1H), 2.2-2.6 (m, 5H), 1.07 (d, J=6.8 Hz, 3H).

Step 2: To a vial were added 3-(3-bromo-4-methoxyphenyl)-2-methylcyclopentanone (135 mg, 0.57 mmol), NH$_2$OH (94 mg, 1.43 mmol), and 3 mL EtOH. The resulting reaction mixture was stirred at 75° C. for 2 hrs. Volatiles were removed and the resulting residue was diluted with 20 mL EtOAc, washed with 20 mL sat. Na$_2$CO$_3$ aqueous solution, and then 10 mL brine. The organics were dried over sodium sulfate, filtered and concentrated. The residue was dissolved in 3 mL DCM and was transferred to a vial. To this vial were added tosyl-Cl (109 mg, 0.57 mmol), DMAP (catalytic) and TEA (0.13 mL, 0.95 mmol). The resulting reaction mixture was stirred at rt for 2 hrs. Volatiles were removed. To the remaining material was added acetic acid (3.0 mL). The resulting reaction mixture was stirred at rt overnight. Volatiles were removed. Crude material was diluted with 20 mL EtOAc, washed with 20 mL sat. Na$_2$CO$_3$ aqueous solution, then 10 mL brine. Organics were dried over sodium sulfate, filtered and concentrated. The crude product was purified on reverse phase HPLC eluted with acetonitrile/water (modified with 0.05% TFA) gradient solvents to give 72 mg 3-(3-bromo-4-methoxyphenyl)-2-methylcyclopentanone (intermediate M) as a mixture of cis and trans isomers. MS ESI calc'd. for C$_{13}$H$_{16}$BrNO$_2$ [M+H]+ 298.0 and 300.20, found 298.1 and 300.1.

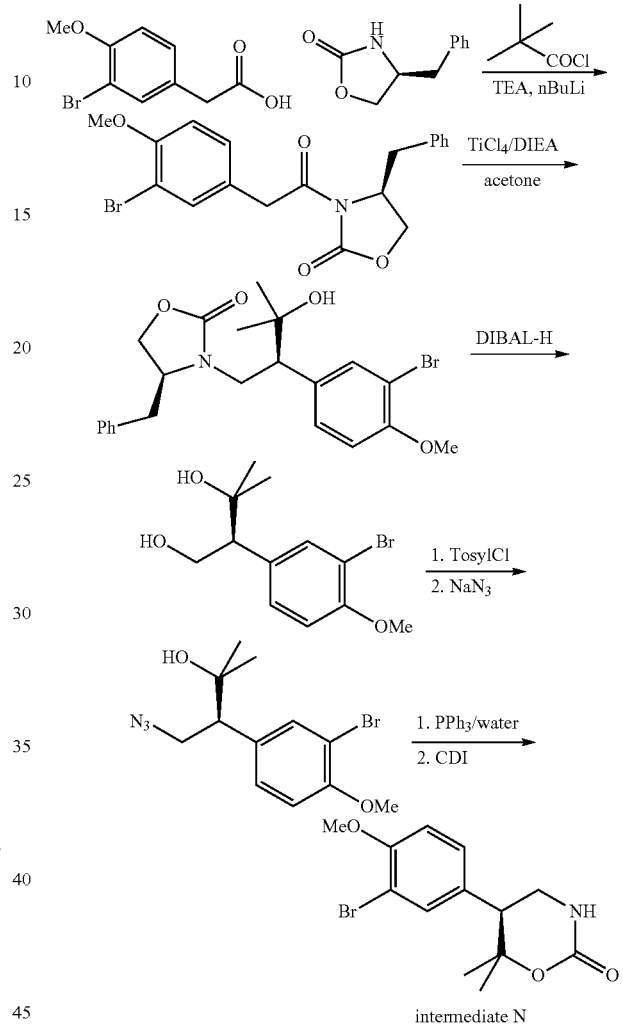

Scheme N intermediate N

Intermediate N (S)-5-(3-bromo-4-methoxyphenyl)-6,6-dimethyl-1,3-oxazinan-2-one

Step 1: To a stirred solution of 2-(3-bromo-4-methoxyphenyl)acetic acid (5 g, 20.40 mmol) in 60 mL THF was added TEA (3.13 mL, 22.44 mmol), and then pivaloyl chloride (2.64 mL, 21.42 mmol) at 0° C. The resulting reaction mixture was stirred at 0° C. for 30 mins. Ice bath was replaced with dry ice acetone bath. To a separate round-bottom flask was added (S)-4-benzyl-2-oxazolidinone (3.62 g, 20.4 mmol) and 50 mL THF. To this solution was added n-BuLi (12.8 mL, 20.4 mmol, 1.6 M in hexane) dropwise via a syringe at −78° C. The resulting reaction mixture was stirred −78° C. for 5 mins. This solution was transferred to the previous flask via channular transferring. After transferring, the reaction mixture was stirred at −78° C. for 30 mins and was allowed to warm up to rt. It was quenched by addition of 100 mL brine and 100 mL water. The reaction mixture was extracted with 200 mL 30%

EtOAc in hexane. The organics were dried over sodium sulfate, filtered and concentrated. Crude product was purified on a Combiflash prepacked silica gel column eluted with 5% to 35% EtOAc in hexane to give 5.7 g desired product as colorless viscous material. $^1$H NMR (500 MHz, CDCl$_3$): δ 7.57 (s, 1H), 7.3 (m, 4H), 7.18 (d, J=7.3 Hz, 1H), 6.92 (d, J=8.5 Hz, 1H), 4.71 (br, 1H), 4.1-4.3 (m, 4H), 3.93 (s, 3H), 3.31 (d, J=12.9 Hz, 1H), 2.81 (dd, J=9.8, 13.2 Hz, 1H).

Step 2: To a round bottom flask were added 10 mL DCM and (S)-4-benzyl-3-(2-(3-bromo-4-methoxyphenyl)acetyl) oxazolidin-2-one (1.0 g, 2.47 mmol). TiCl$_4$ (2.6 mL, 2.60 mmol, 1M DCM solution) was added at 0° C. After stirring at 0° C. for 5 mins, DIEA (0.45 mL, 2.6 mmol) was added via syringe. The reaction mixture was stirred at 0° C. for 30 mins. Acetone (0.27 mL, 3.71 mmol) was added followed by more of TiCl$_4$ (2.6 mL, 2.6 mmol, 1 M DCM solution). The reaction mixture was stirred at 0° C. for 2 hrs. It was quenched by addition of 80 mL sat. NH$_4$Cl aqueous solution. The resulting reaction mixture was extracted with 120 mL EtOAc/hexane (1:1). Organics were dried over sodium sulfate, filtered and concentrated. Crude product was purified on Combiflash prepacked silica gel column, eluted with 5% to 40% EtOAc in hexane to give 1.1 g desired product as viscous material. $^1$H NMR (500 MHz, CDCl$_3$): δ 7.70 (s, 1H), 7.1-7.4 (m, 6H), 6.88 (d, J=8.5 Hz, 1H), 4.68 (m, 1H), 4.1 (m, 2H), 3.93 (s, 3H), 3.83 (s, 1H), 3.43 (dd, J=3.4, 13.3 Hz, 1H), 2.82 (dd, J=9.9, 13.3 Hz, 1H), 1.46 (s, 3H), 1.09 (s, 3H).

Step 3: To a solution of (S)-4-benzyl-3-((R)-2-(3-bromo-4-methoxyphenyl)-3-hydroxy-3-methylbutanoyl)oxazolidin-2-one (540 mg, 1.17 mmol) in 10 mL THF was added a solution of DIBAL-H (3.5 mL, 3.50 mmol, 1 M toluene solution) via a syringe at 0° C. After stirring at 0° C. for 20 mins, more DIBAL-H (1.0 mL, 1.0 mmol) was added. After stirring at 0° C. for 10 mins, the reaction mixture was quenched by addition of 10 mL EtOAc and then 10 mL 3N HCl. After stirring at 0° C. for 15 mins, the reaction was diluted with 30 mL EtOAc/hexane (1:1) and 30 mL water. The layers were separated. The organics were washed with 20 mL 10% KOH aqueous solution, dried over sodium sulfate, filtered and concentrated. Crude product was purified on prepacked Combiflash column and eluted with 5% to 40% EtOAc in hexane to give 185 mg viscous material. NMR indicated it is a mixture of desired product and the chiral auxiliary. $^1$H NMR (500 MHz, CDCl$_3$): δ 7.49 (d, J=2.1 Hz, 1H), 7.23 (dd, J=2.1, 8.3 Hz, 1H), 6.88 (d, J=8.3 Hz, 1H), 4.05 (m, 2H), 3.92 (s, 3H), 2.85 (m, 1H), 1.27 (s, 3H), 1.24 (s, 3H).

Step 4: To a solution of (S)-2-(3-bromo-4-methoxyphenyl)-3-methylbutane-1,3-diol (115 mg, 0.40 mmol) in 2 mL DCM were added DMAP (catalytic), DIEA (0.21 mL, 1.29 mmol) and tosyl chloride (106 mg, 0.57 mmol). The resulting reaction mixture was stirred at 40° C. overnight. It was diluted with 20 mL EtOAc and washed with 20 mL water. The organics were dried over sodium sulfate, filtered and concentrated. Crude product was purified by chromatography to give 132 mg tosylate product. $^1$H NMR (500 MHz, CDCl$_3$): δ 7.63 (d, J=8.1 Hz, 2H), 7.31 (d, J=8.1 Hz, 2H), 7.22 (d, J=2.0 Hz, 1H), 7.07 (dd, J=2.0, 8.6 Hz, 1H), 6.82 (d, J=8.4 Hz, 1H), 4.65 (dd, J=4.9, 10.0 Hz, 1H), 4.31 (t, J=9.9 Hz, 1H), 3.92 (s, 3H), 2.9 (m, 1H), 2.48 (s, 3H), 1.28 (s, 3H), 1.10 (s, 3H).

Step 5: To a solution of (S)-2-(3-bromo-4-methoxyphenyl)-3-hydroxy-3-methylbutyl 4-methylbenzenesulfonate (58 mg, 0.13 mmol) in 2 mL DMF was added NaN$_3$ (34 mg, 0.52 mmol). The resulting reaction mixture was heated at 60° C. overnight and was then diluted with 10 mL EtOAc/hexane (1:1) and 10 mL water. The layers were separated. The organics were dried over sodium sulfate, filtered and concentrated. Crude product was purified on Combiflash prepacked silica gel column, eluted with hexane to 40% EtOAc in hexane to give 38 mg desired product. $^1$H NMR (500 MHz, CDCl$_3$): δ 7.49 (d, J=1.9 Hz, 1H), 7.22 (dd, J=2.1, 8.5 Hz, 1H), 6.91 (d, J=8.4 Hz, 1H), 3.93 (s, 3H), 3.9 (m, 1H), 3.71 (m, 1H), 2.82 (m, 1H), 1.28 (s, 3H), 1.17 (s, 3H).

Step 6: To a 25 mL round bottom flask containing (S)-4-azido-3-(3-bromo-4-methoxyphenyl)-2-methylbutan-2-ol (38 mg, 0.12 mmol) were added PPh$_3$ (48 mg, 0.18 mmol), THF (2 mL) and water (0.2 mL). The resulting reaction mixture was heated to reflux for 2 hrs. Volatiles were removed under vacuum. To the residue was added 2 mL THF, DIEA (0.063 mL, 0.36 mmol) and CDI (39 mg, 0.24 mmol). The resulting reaction mixture was heated at 60° C. for 3 hrs. It was then diluted with 10 mL saturated NH$_4$Cl and extracted with 15 mL EtOAc. The organics were dried over sodium sulfate, filtered and concentrated. Crude product was purified on a Combiflash prepacked silica gel column which was eluted with EtOAc to give 30 mg of the desired product (intermediate N). $^1$H NMR (500 MHz, CDCl$_3$): δ 7.41 (s, 1H), 7.16 (d, J=7.8 Hz, 1H), 6.88 (d, J=8.5 Hz, 1H), 6.76 (s, 1H), 3.90 (s, 3H), 3.65 (t, J=11.4 Hz, 1H), 3.46 (br, 1H), 3.0 (br, 1H), 1.34 (s, 3H), 1.32 (s, 3H).

EXAMPLES

General Synthetic Schemes

Compounds of Formula I and Formula Ia can be synthesized according to the general schemes outlined below. Syntheses of representative examples follow. The starting materials in the schemes are commercially available or are readily synthesized by a person skilled in the art.

The schemes and examples are illustrative and are not to be construed as limiting the invention.

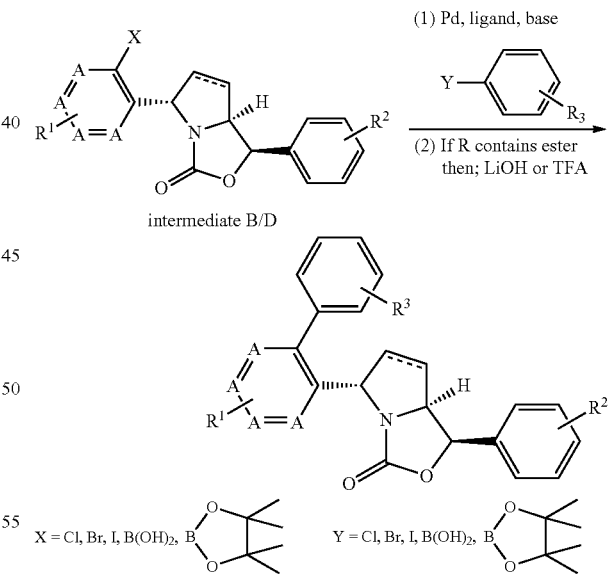

Scheme 1

In Scheme 1, A is CH or N, where the H of CH can be substituted. In accordance with Scheme 1, a cross-coupling reaction between Intermediate B, D or E and an appropriately functionalized boronic acid/ester provides compounds of the general formula I and Ia. In cases where an ester group is present in the final compound, a saponification or hydrolysis may subsequently be carried out to generate the acid. In cases where a protecting group, such as acetonide or Boc, is present, a deprotection step may also be needed.

Scheme 2
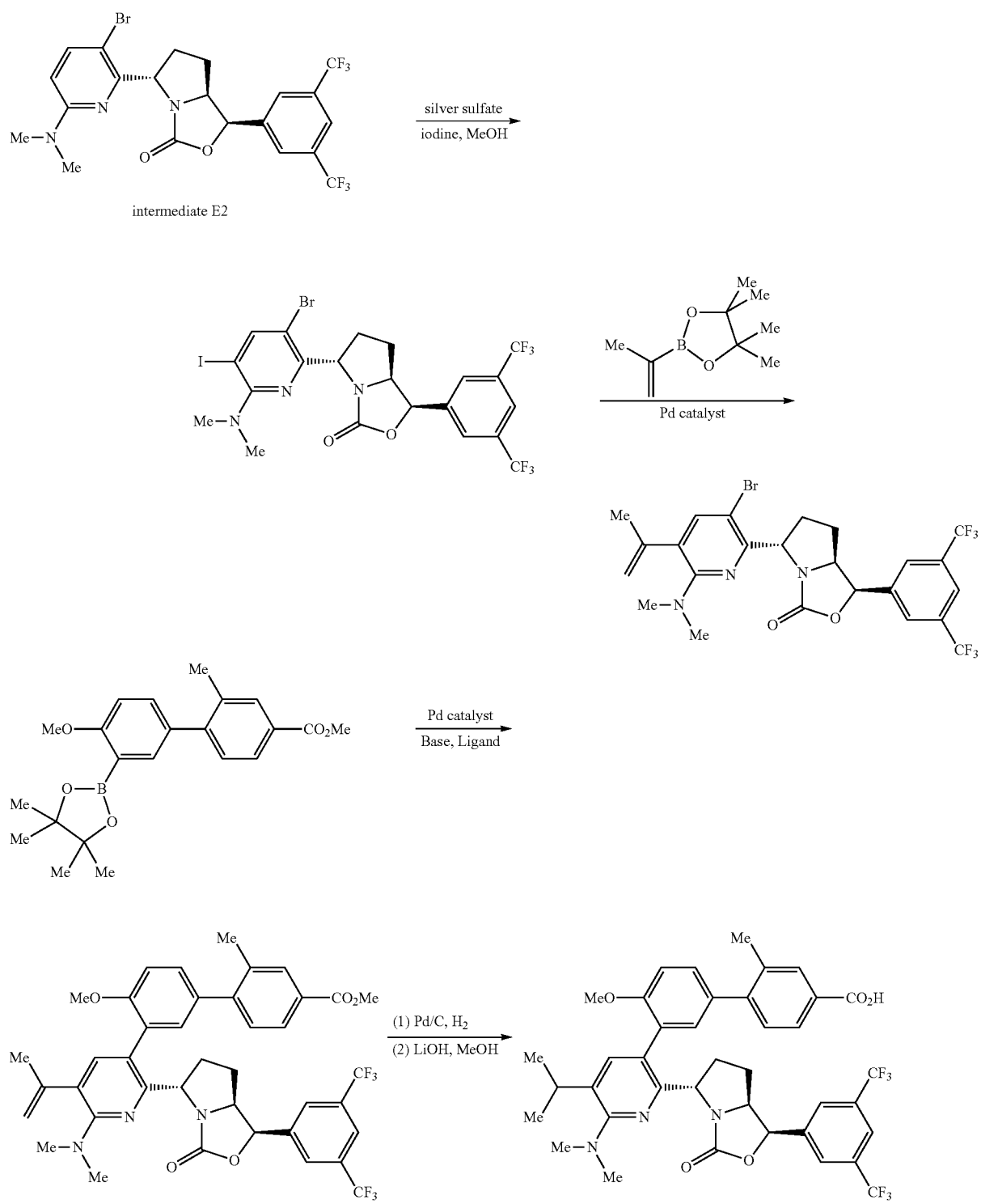
In accordance with Scheme 2, Intermediate E is transformed to an iodide which is subjected to a selective Suzuki reaction to install an isopropenyl group. A second Suzuki reaction of the bromide with a known boronic ester completes the carbon skeleton of the molecule. A reduction and saponification provides a compound of the general formula (I).
Scheme 3
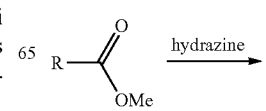

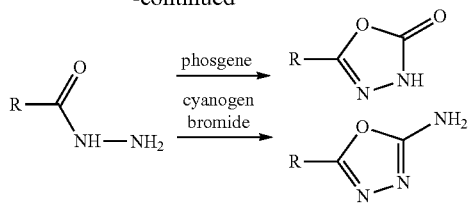

In accordance with Scheme 3, a compound of the general formula (I) containing an ester moiety may further be transformed into a 1,3,4-oxadiazol-2(3H)-one or a 1,3,4-oxadiazol-2-amine group via a two step sequence.

EXAMPLES

The following non-limiting schemes and examples are provided so that the invention will be more fully appreciated and understood. Starting materials are made using known procedures or as shown below.

Example 1

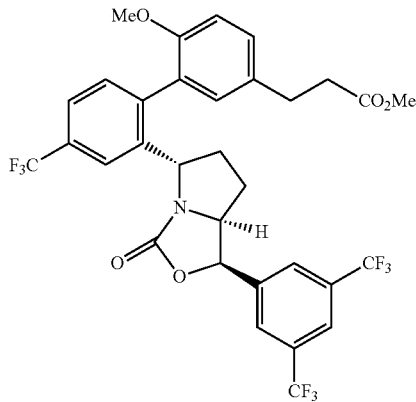 [SMILES: COC(=O)CCc1ccc(OC)c(-c2ccc(C(F)(F)F)cc2[C@@H]2CC[C@H]3[C@@H](c4cc(C(F)(F)F)cc(C(F)(F)F)c4)OC(=O)N23)c1]

methyl 3-[2'-{(1R,5S,7aS)-1-[3,5-bis(trifluoromethyl)phenyl]-3-oxotetrahydro-1H-pyrrolo[1,2-c][1,3]oxazol-5-yl}-6-methoxy-4'-(trifluoromethyl)biphenyl-3-yl]propanoate (Scheme 1)

To Intermediate B2 (30 mg, 0.044 mmol) was added THF (2 mL), water (0.1 mL), tribasic potassium phosphate (45.3 mg, 0.213 mmol), methyl 3-[4-methoxy-3-(4,4,5,5-tetramethyl-1,3,2-dioxaborolan-2-yl)phenyl]propanoate (51.3 mg, 0.16 mmol) (Intermediate H), palladium(II) acetate (1.2 mg, 5.34 mmol), and 1,1'-bis(di-tert-butylphosphino)ferrocene (2.53 mg, 5.34 µmol). The system was flushed with nitrogen gas and was heated at 62° C. overnight. The reaction was diluted with ethyl acetate:hexanes (1:2, 10 mL) and was partitioned with water (10 mL). The organic was dried over sodium sulfate, filtered and concentrated. The crude product was purified by reverse phase HPLC to yield methyl 3-[2'-{(1R,5S,7aS)-1-[3,5-bis(trifluoromethyl)phenyl]-3-oxotetrahydro-1H-pyrrolo[1,2-c][1,3]oxazol-5-yl}-6-methoxy-4'-(trifluoromethyl)biphenyl-3-yl]propanoate (27 mg, 0.04 mmol). $^1$H NMR indicated that this compound exists as a pair of rotamers at 1.2:1 ratio. $^1$H NMR (500 MHz, CDCl$_3$) δ 7.87 (s, 1H), 7.81 (s, 2H), 7.75 (s, 1H, major rotamer), 7.73 (s, 1H, minor rotamer) 7.6 (m, 1H) 6.8-7.3 (m, 4H), 6.06 (d, J=7.9 Hz, 1H, major rotamer), 6.06 (d, J=7.9 Hz, 1H, major rotamer), 6.01 (d, 1H, minor rotamer), 5.12 (m, 1H, major rotamer), 4.98 (m, 1H, minor rotamer), 4.1 (m, 1H), 3.84 (s, 3H, major rotamer), 3.68 (s, 3H), 3.67 (s, 3H) 3.62 (s, 3H, minor rotamer), 2.9 (m, 2H), 2.6 (m, 2H), 0.9-1.7 (m, 4H). MS ESI calc'd. for C$_{32}$H$_{27}$F$_9$NO$_5$ [M+H]+ 676.2, found 676.4. RTA (95% HS): 296 nM Example 2

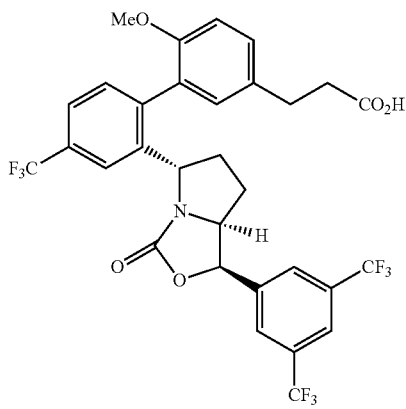 [SMILES: COc1ccc(CCC(=O)O)cc1-c1ccc(C(F)(F)F)cc1[C@@H]1CC[C@H]2[C@@H](c3cc(C(F)(F)F)cc(C(F)(F)F)c3)OC(=O)N12]

3-[2'-{(1R,5S,7aS)-1-[3,5-bis(trifluoromethyl)phenyl]-3-oxotetrahydro-1H-pyrrolo[1,2-c][1,3]oxazol-5-yl}-6-methoxy-4'-(trifluoromethyl)biphenyl-3-yl] propanoic acid (Scheme 1)

To methyl 3-[2'-{(1R,5S,7aS)-1-[3,5-bis(trifluoromethyl)phenyl]-3-oxotetrahydro-1H-pyrrolo[1,2-c][1,3]oxazol-5-yl}-6-methoxy-4'-(trifluoromethyl)biphenyl-3-yl]propanoate (20 mg, 0.03 mmol) in THF (2 mL) and water (0.5 mL) was added lithium hydroxide-monohydrate (6.21 mg, 0.148 mmol) and hydrogen peroxide (30%, 33.6 mg, 0.296 mmol). The reaction mixture was stirred at room temperature. Upon completion the reaction was diluted with water (10 mL), and solid Na$_2$SO$_3$ was added to quench hydrogen peroxide. The solution was acidified with aqueous HCl (1 M) and was partitioned with ethyl acetate (20 mL). The organic was dried over sodium sulfate, filtered and concentrated before purification by reverse phase HPLC to yield 3-[2'-{(1R,5S,7aS)-1-[3,5-bis(trifluoromethyl)phenyl]-3-oxotetrahydro-1H-pyrrolo[1,2-c][1,3]oxazol-5-yl}-6-methoxy-4'-(trifluoromethyl)biphenyl-3-yl]propanoic acid (9 mg, 0.014 mmol). $^1$H NMR indicated that this compound exists as a pair of rotamers at a 3:1 ratio. $^1$H NMR (500 MHz, CDCl$_3$) δ 7.87 (s, 1H), 7.82 (s, 2H), 7.75 (s, 1H, minor rotamer), 7.73 (s, 1H, major rotamer) 7.6 (m, 1H) 6.9-7.4 (m, 4H), 6.08 (d, J=8.1 Hz, 1H, major rotamer), 5.15 (t, 1H, minor rotamer) 5.06 (t, J=8.2 Hz, 1H, major rotamer), 4.6 (m, 1H, major rotamer) 4.45 (m, 1H, minor rotamer), 4.98 (m, 1H, minor rotamer), 4.1 (m, 1H), 3.85 (s, 3H, minor rotamer), 3.69 (s, 3H, major rotamer), 2.4-3.1 (m, 4H), 0.9-1.9 (m, 4H). MS ESI calc'd. for C$_{31}$H$_{25}$F$_9$NO$_5$ [M+H]+ 662.2, found 662.3. RTA (95% HS): 128 nM

Example 3

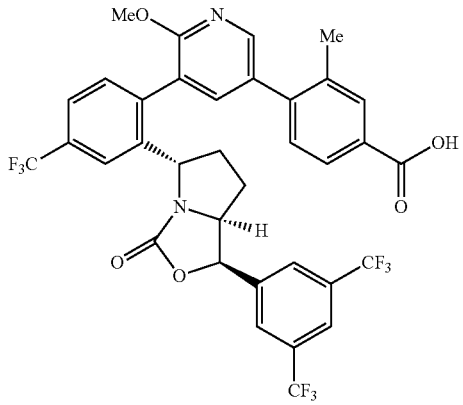 [SMILES: COc1ncc(-c2ccc(C(=O)O)cc2C)cc1-c1ccc(C(F)(F)F)cc1[C@@H]1CC[C@H]2[C@@H](c3cc(C(F)(F)F)cc(C(F)(F)F)c3)OC(=O)N12]

4-{5-[2-{(1R,5S,7aS)-1-[3,5-bis(trifluoromethyl)phenyl]-3-oxotetrahydro-1H-pyrrolo[1,2-c][1,3]oxazol-5-yl}-4-(trifluoromethyl)phenyl]-6-methoxypyridin-3-yl}-3-methylbenzoic acid (Scheme 1)

Step 1: To a solution of Intermediate B2 (4.4 g, 7.83 mmol) in dioxane (50 mL) and water (5 mL) was added Intermediate I (3.66 g, 8.61 mmol), potassium phosphate (4.98 g, 23.5 mmol) and 1,1'-bis(di-tert-butylphosphino)ferrocene palladium dichloride (0.255 g, 0.39 mmol). The mixture was purged with nitrogen and heated at 80° C. overnight. The reaction was poured into ethyl acetate and was washed with water, dried over sodium sulfate, filtered and concentrated. The resultant residue was purified by column chromatography to yield tert-butyl 4-{5-[2-{(1R,5S,7aS)-1-[3,5-bis(trifluoromethyl)phenyl]-3-oxotetrahydro-1H-pyrrolo[1,2-c][1,3]oxazol-5-yl}-4-(trifluoromethyl)phenyl]-6-methoxypyridin-3-yl}-3-methylbenzoate (4.5 g, 5.77 mmol). MS ESI calc'd. for $C_{39}H_{33}F_9N_2O_5$ [M+H]+ 781.2, found 781.2.

Step 2: To tert-butyl 4-{5-[2-{(1R,5S,7aS)-1-[3,5-bis(trifluoromethyl)phenyl]-3-oxotetrahydro-1H-pyrrolo[1,2-c][1,3]oxazol-5-yl}-4-(trifluoromethyl)phenyl]-6-methoxypyridin-3-yl}-3-methylbenzoate (1 g, 1.28 mmol) was added dichloromethane:TFA (9:1, 10 mL). The reaction was stirred overnight at room temperature. Upon completion the solvent was removed under reduced pressure and the resultant residue was redissolved in acetonitrile for direct purification by reverse phase HPLC to yield 4-{5-[2-{(1R,5S,7aS)-1-[3,5-bis(trifluoromethyl)phenyl]-3-oxotetrahydro-1H-pyrrolo[1,2-c][1,3]oxazol-5-yl}-4-(trifluoromethyl)phenyl]-6-methoxypyridin-3-yl}-3-methylbenzoic acid (0.674 g, 0.931 mmol). $^1$H NMR indicated that this compound exists as a pair of rotamers at 1.2:1 ratio. $^1$H NMR (500 MHz, CDCl$_3$) δ8.27 (s, 1H), 8.04 (m, 4H, peaks overlap for the two rotamers), 7.90 (s, 1H), 7.84 (s, 2H, minor rotamer), 7.83 (s, 2H, major rotamer), 7.75 (s, 1H, major rotamer), 7.67 (s, 1H, minor rotamer), 7.63 (d, J=8 Hz, 1H, major rotamer), 7.42 (m, 2H), 7.38 (d, J=7.9 Hz, 1H, major rotamer), 7.36 (d, J=7.9 Hz, 1H, minor rotamer), 6.11 (d, J=7.9 Hz, 1H, minor rotamer), 6.09 (d, J=7.9 Hz, 1H, major rotamer), 5.27 (t, J=7.9 Hz, 1H, major rotamer), 4.95 (t, J=7.9 Hz, 1H, minor rotamer), 4.62 (m, 1H, minor rotamer), 4.51 (m, 1H, major rotamer), 4.12 (s, 3H, minor rotamer), 3.94 (s, 3H, minor rotamer), 2.45 (s, 3H, minor rotamer), 2.45 (s, 3H, major rotamer), 2.37 (m, 1H), 2.2 (m, 1H), 2.05 (m, 1H), 1.85 (m, 1H), 1.55 (m, 1H), 1.4 (m, 1H), 1.1 (m, 2H). MS ESI calc'd. for $C_{35}H_{26}F_9N_2O_5$ [M+H]+ 725.2, found 725.0. RTA (95% HS): 53.18 nM

Example 4

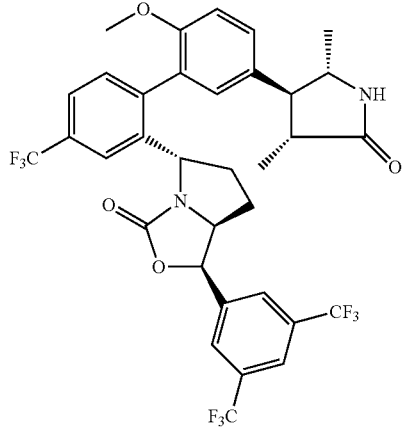 [SMILES: COc1ccc([C@H]2[C@H](C)NC(=O)[C@@H]2C)cc1-c1ccc(C(F)(F)F)cc1[C@@H]1CC[C@H]2[C@@H](c3cc(C(F)(F)F)cc(C(F)(F)F)c3)OC(=O)N12]

(1R,5S,7aS)-1-(3,5-bis(trifluoromethyl)phenyl)-5-(5'-((2S,3S,4R)-2,4-dimethyl-5-oxopyrrolidin-3-yl)-2'-methoxy-4-(trifluoromethyl)-[1,1'-biphenyl]-2-yl)tetrahydropyrrolo[1,2-c]oxazol-3(1H)one (Scheme 1)

To a 10 mL microwave tube was added (1R,5S,7aS)-1-(3,5-bis(trifluoromethyl)phenyl)-5-(2-(4,4,5,5-tetramethyl-1,3,2-dioxaborolan-2-yl)-5-(trifluoromethyl)phenyl)tetrahydropyrrolo[1,2-c]oxazol-3(1H)-one (intermediate B3, 70 mg, 0.115 mmol), intermediate J2 (37 mg, 0.104 mmol), chloro(2-dicyclohexylphosphino-2'4'6'-triisopropyl-1,1'-biphenyl)[2-(2-amino-1,1'-biphenyl)]palladium(II) (Xphos Precatalyst) (9 mg, 0.021 mmol), potassium phosphate (33 mg, 0.157 mmol), dioxane (1 mL) and water (0.1 mL). The reaction mixture was degassed and filled with N$_2$ and heated at 110° C. for 3 hrs. It was cooled to rt and diluted with EtOAc (3 mL). The mixture was washed with water and brine and then concentrated. The residue was purified by reverse phase HPLC. The product fraction was concentrated and extracted with EtOAc. The organic layer was washed with brine and concentrated to give the Boc protected product. It was dissolved in 0.5 mL of DCM and treated with 1 mL of TFA at rt for 10 mins. Volatiles were removed under vacuum. The residue was purified by reverse phase HPLC. Fractions contain desired product was lyophilized to give the title compound (40 mg) as white powder. MS ESI calc'd. for $C_{34}H_{29}F_9N_2O_4$ [M+H]+ 701.0, found 701.2. RTA (95% HS): 398 nM The following compounds in table 4 were prepared according to general scheme 1 using the procedure outlined in example 1, 2 3 and 4, utilizing commercially available or known halide or boronic acids/esters. In step 1, intermediate B/D/E may be used. In cases where an ester moiety is present, saponification or hydrolysis may be carried out using the procedure outlined in example 2 or 3.

TABLE 4

| Ex | Structure | IUPAC Name | IC$_{50}$ (nM) | Exact Mass [M + H]+ |
|---|---|---|---|---|
| 5 | 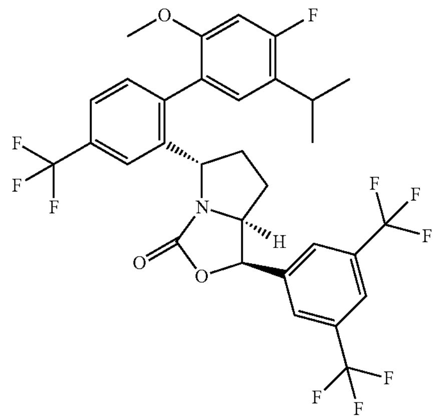 [SMILES: COc1cc(F)c(C(C)C)cc1-c1ccc(C(F)(F)F)cc1[C@@H]1CC[C@H]2[C@@H](c3cc(C(F)(F)F)cc(C(F)(F)F)c3)OC(=O)N12] | (1R,5S,7aS)-1-[3,5-bis(trifluoromethyl)phenyl]-5-[4'-fluoro-2'-methoxy-5'-(1-methylethyl)-4-(trifluoromethyl)biphenyl-2-yl]tetrahydro-1H-pyrrolo[1,2-c][1,3]oxazol-3-one | 84.92 | Calc'd 650.2, found 650.3 |
| 6 | 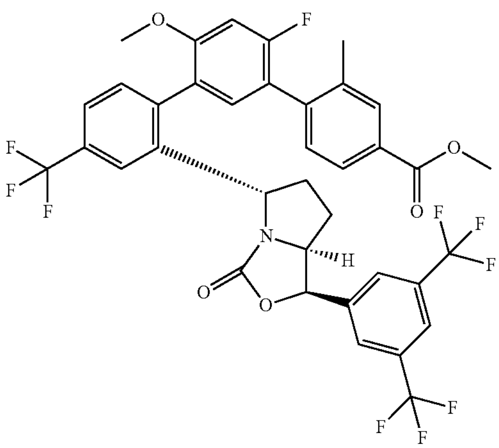 [SMILES: COC(=O)c1ccc(-c2cc(-c3ccc(C(F)(F)F)cc3[C@@H]3CC[C@H]4[C@@H](c5cc(C(F)(F)F)cc(C(F)(F)F)c5)OC(=O)N34)c(OC)cc2F)c(C)c1] | methyl 2''-{(1R,5S,7aS)-1-[3,5-bis(trifluoromethyl)phenyl]-3-oxotetrahydro-1H-pyrrolo[1,2-c][1,3]oxazol-5-yl}-6'-fluoro-4'-methoxy-2-methyl-4''-(trifluoromethyl)-1,1':3',1''-terphenyl-4-carboxylate | 641 | Calc'd 756.2, found 756.4 |
| 7 | 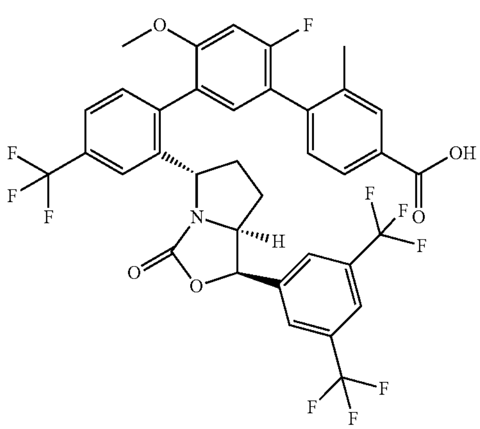 [SMILES: COc1cc(F)c(-c2ccc(C(=O)O)cc2C)cc1-c1ccc(C(F)(F)F)cc1[C@@H]1CC[C@H]2[C@@H](c3cc(C(F)(F)F)cc(C(F)(F)F)c3)OC(=O)N12] | 2''-{(1R,5S,7aS)-1-[3,5-bis(trifluoromethyl)phenyl]-3-oxotetrahydro-1H-pyrrolo[1,2-c][1,3]oxazol-5-yl}-6'-fluoro-4'-methoxy-2-methyl-4''-(trifluoromethyl)-1,1':3',1''-terphenyl-4-carboxylic acid | 53.7 | Calc'd 742.2, found 742.4 |

TABLE 4-continued

| Ex | Structure | IUPAC Name | IC$_{50}$ (nM) | Exact Mass [M + H]+ |
|---|---|---|---|---|
| 8 | 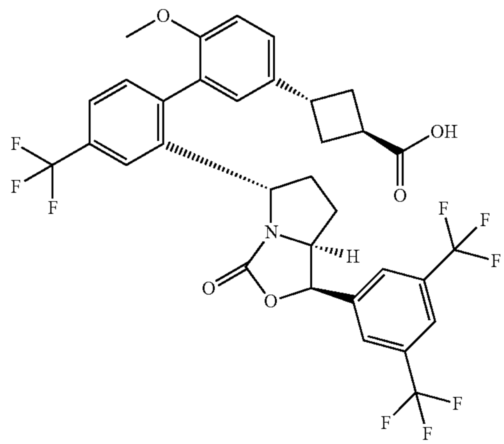 [SMILES: COc1ccc([C@H]2C[C@H](C(=O)O)C2)cc1-c1ccc(C(F)(F)F)cc1[C@@H]1CC[C@H]2[C@@H](c3cc(C(F)(F)F)cc(C(F)(F)F)c3)OC(=O)N12] | trans-3-[2'-{(1R,5S,7aS)-1-[3,5-bis(trifluoromethyl)phenyl]-3-oxotetrahydro-1H-pyrrolo[1,2-c][1,3]oxazol-5-yl}-6-methoxy-4'-(trifluoromethyl)biphenyl-3-yl]cyclobutanecarboxylic acid | 96.54 | Calc'd 688.2, found 688.3 |
| 9 | 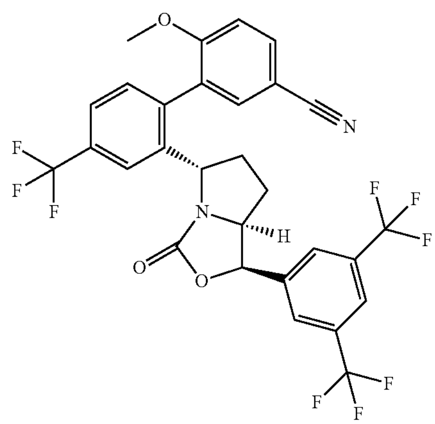 [SMILES: COc1ccc(C#N)cc1-c1ccc(C(F)(F)F)cc1[C@@H]1CC[C@H]2[C@@H](c3cc(C(F)(F)F)cc(C(F)(F)F)c3)OC(=O)N12] | 2'-{(1R,5S,7aS)-1-[3,5-bis(trifluoromethyl)phenyl]-3-oxotetrahydro-1H-pyrrolo[1,2-c][1,3]oxazol-5-yl}-6-methoxy-4'-(trifluoromethyl)biphenyl-3-carbonitrile | 224.2 | Calc'd 615.1, found 615.4 |
| 10 | 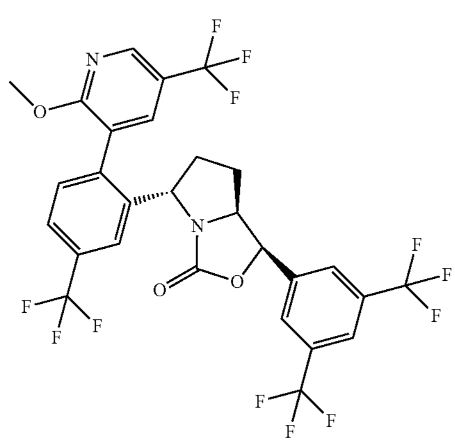 [SMILES: COc1ncc(C(F)(F)F)cc1-c1ccc(C(F)(F)F)cc1[C@@H]1CC[C@H]2[C@@H](c3cc(C(F)(F)F)cc(C(F)(F)F)c3)OC(=O)N12] | (1R,5S,7aS)-1-[3,5-bis(trifluoromethyl)phenyl]-5-{2-[2-methoxy-5-(trifluoromethyl)pyridin-3-yl]-5-(trifluoromethyl)phenyl}tetrahydro-1H-pyrrolo[1,2-c][1,3]oxazol-3-one | 371.4 | Calc'd 659.1, found 659.5 |

TABLE 4-continued

| Ex | Structure | IUPAC Name | IC$_{50}$ (nM) | Exact Mass [M + H]+ |
|---|---|---|---|---|
| 11 | 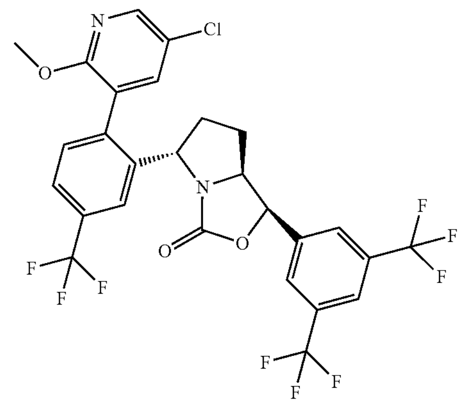 [SMILES: COc1ncc(Cl)cc1-c1ccc(C(F)(F)F)cc1[C@@H]1CC[C@H]2[C@@H](c3cc(C(F)(F)F)cc(C(F)(F)F)c3)OC(=O)N12] | (1R,5S,7aS)-1-[3,5-bis(trifluoromethyl)phenyl]-5-[2-(5-chloro-2-methoxypyridin-2-yl)-5-(trifluoromethyl)phenyl]tetrahydro-1H-pyrrolo[1,2-c][1,3]oxazol-3-one | 294.5 | Calc'd 625.1, found 625.3 |
| 12 | 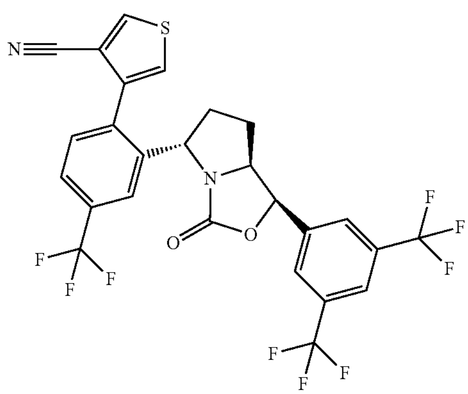 [SMILES: N#Cc1cscc1-c1ccc(C(F)(F)F)cc1[C@@H]1CC[C@H]2[C@@H](c3cc(C(F)(F)F)cc(C(F)(F)F)c3)OC(=O)N12] | 4-[2-{(1R,5S,7aS)-1-[3,5-bis(trifluoromethyl)phenyl]-3-oxotetrahydro-1H-pyrrolo[1,2-c][1,3]oxazol-5-yl}-4-(trifluoromethyl)phenyl]thiophene-3-carbonitrile | 266 | Calc'd 591.1, found 591.4 |
| 13 | 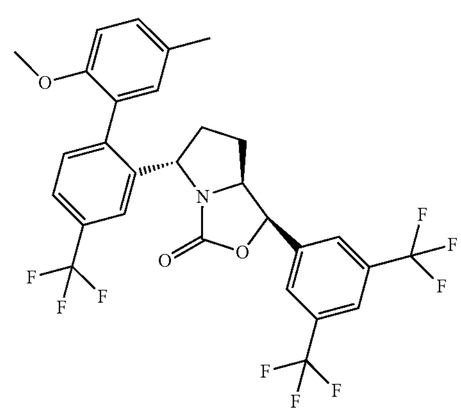 [SMILES: COc1ccc(C)cc1-c1ccc(C(F)(F)F)cc1[C@@H]1CC[C@H]2[C@@H](c3cc(C(F)(F)F)cc(C(F)(F)F)c3)OC(=O)N12] | (1R,5S,7aS)-1-[3,5-bis(trifluoromethyl)phenyl]-5-[2'-methoxy-5'-methyl-4-(trifluoromethyl)biphenyl-2-yl]tetrahydro-1H-pyrrolo[1,2-c][1,3]oxazole-3-one | 262.8 | Calc'd 604.2, found 604.5 |

TABLE 4-continued

| Ex | Structure | IUPAC Name | IC$_{50}$ (nM) | Exact Mass [M + H]+ |
|----|-----------|------------|----------------|---------------------|
| 14 | 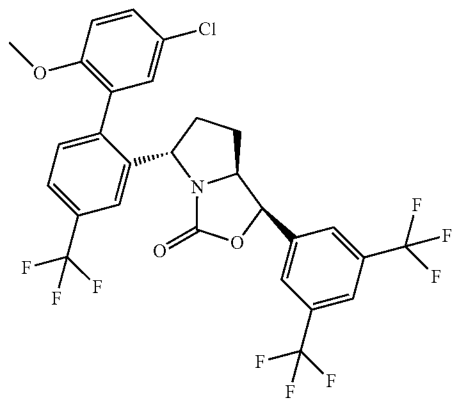 [SMILES: COc1ccc(Cl)cc1-c1ccc(C(F)(F)F)cc1[C@@H]1CC[C@H]2[C@@H](c3cc(C(F)(F)F)cc(C(F)(F)F)c3)OC(=O)N12] | (1R,5S,7aS)-1-[3,5-bis(trifluoromethyl)phenyl]-5-[5'-chloro-2'-methoxy-4-(trifluoromethyl)biphenyl-2-yl]tetrahydro-1H-pyrrolo[1,2-c][1,3]oxazol-3-one | 233.3 | Calc'd 624.1, found 624.5 |
| 15 | 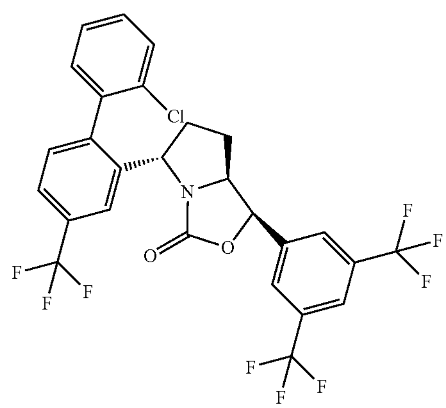 [SMILES: O=C1O[C@H](c2cc(C(F)(F)F)cc(C(F)(F)F)c2)[C@@H]2CC[C@@H](c3cc(C(F)(F)F)ccc3-c3ccccc3Cl)N12] | (1R,5S,7aS)-1-[3,5-bis(trifluoromethyl)phenyl]-5-[2'-chloro-4-(trifluoromethyl)biphenyl-2-yl]tetrahydro-1H-pyrrolo[1,2-c][1,3]oxazol-3-one | 452.8 | Calc'd 594.1, found 594.3 |
| 16 | 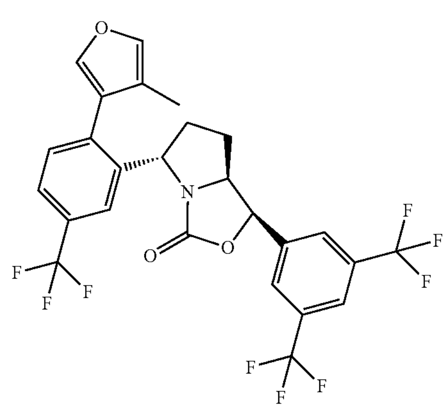 [SMILES: Cc1cocc1-c1ccc(C(F)(F)F)cc1[C@@H]1CC[C@H]2[C@@H](c3cc(C(F)(F)F)cc(C(F)(F)F)c3)OC(=O)N12] | (1R,5S,7aS)-1-[3,5-bis(trifluoromethyl)phenyl]-5-[2-(4-methylfuran-3-yl)-5-(trifluoromethyl)phenyl]tetrahydro-1H-pyrrolo[1,2-c][1,3]oxazol-3-one | 343.4 | [M − H]⁻ Calc'd 562.1, found 562.3 |

TABLE 4-continued

| Ex | Structure | IUPAC Name | IC$_{50}$ (nM) | Exact Mass [M + H]+ |
|---|---|---|---|---|
| 17 | 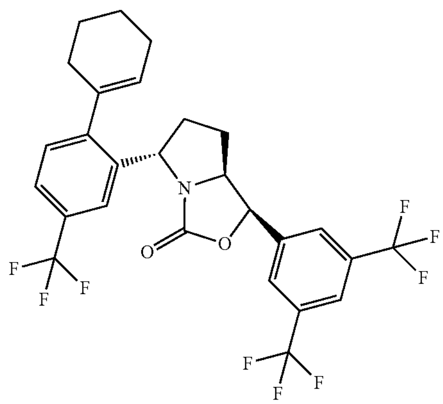 [SMILES: O=C1O[C@H](c2cc(C(F)(F)F)cc(C(F)(F)F)c2)[C@@H]2CC[C@@H](c3cc(C(F)(F)F)ccc3C3=CCCCC3)N12] | (1R,5S,7aS)-1-[3,5-bis(trifluoromethyl)phenyl]-5-[2-cyclohex-1-en-1-yl-5-(trifluoromethyl)phenyl]tetrahydro-1H-pyrrolo[1,2-c][1,3]oxazol-3-one | 73.63 | Calc'd 564.2, found 564.5 |
| 18 | 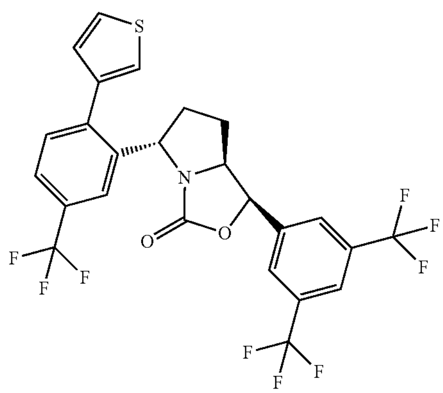 [SMILES: O=C1O[C@H](c2cc(C(F)(F)F)cc(C(F)(F)F)c2)[C@@H]2CC[C@@H](c3cc(C(F)(F)F)ccc3-c3ccsc3)N12] | (1R,5S,7aS)-1-[3,5-bis(trifluoromethyl)phenyl]-5-[2-thiophen-3-yl-5-(trifluoromethyl)phenyl]tetrahydro-1H-pyrrolo[1,2-c][1,3]oxazol-3-one | 102.8 | [M − H]$^-$ Calc'd 564.1, found 564.3 |
| 19 | 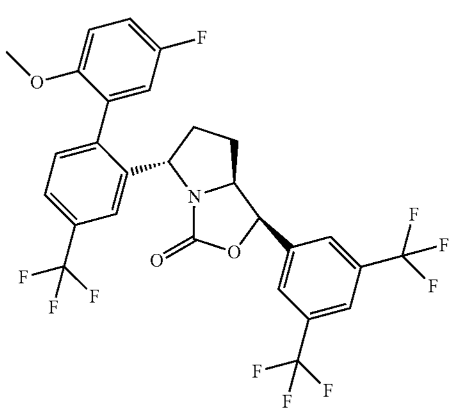 [SMILES: COc1ccc(F)cc1-c1ccc(C(F)(F)F)cc1[C@@H]1CC[C@H]2[C@@H](c3cc(C(F)(F)F)cc(C(F)(F)F)c3)OC(=O)N12] | (1R,5S,7aS)-1-[3,5-bis(trifluoromethyl)phenyl]-5-[5'-fluoro-2'-methoxy-4-(trifluoromethyl)biphenyl-2-yl]tetrahydro-1H-pyrrolo[1,2-c][1,3]oxazol-3-one | 165.7 | Calc'd 608.1, found 608.4 |

TABLE 4-continued

| Ex | Structure | IUPAC Name | IC$_{50}$ (nM) | Exact Mass [M + H]+ |
|---|---|---|---|---|
| 20 | 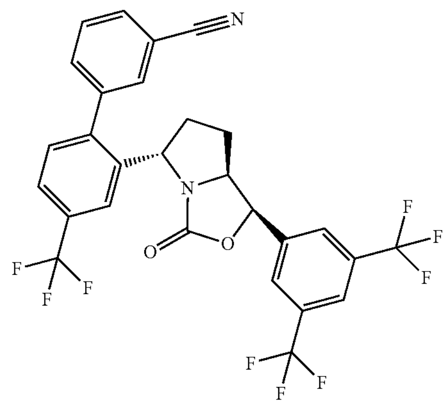 [SMILES: N#Cc1cccc(-c2ccc(C(F)(F)F)cc2[C@@H]2CC[C@H]3[C@@H](c4cc(C(F)(F)F)cc(C(F)(F)F)c4)OC(=O)N23)c1] | 2'-{(1R,5S,7aS)-1-[3,5-bis(trifluoromethyl)phenyl]-3-oxotetrahydro-1H-pyrrolo[1,2-c][1,3]oxazol-5-yl}-4'-(trifluoromethyl)biphenyl-3-carbonitrile | 177.1 | [M − H]⁻ calc'd 583.4, found 583.4 |
| 21 | 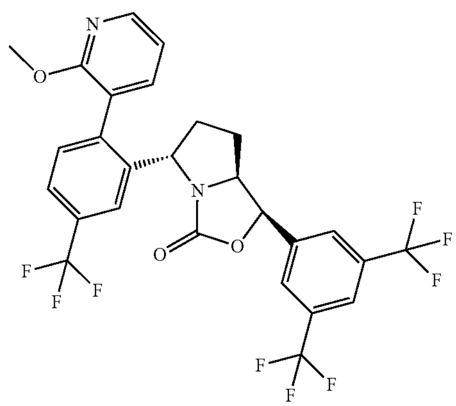 [SMILES: COc1ncccc1-c1ccc(C(F)(F)F)cc1[C@@H]1CC[C@H]2[C@@H](c3cc(C(F)(F)F)cc(C(F)(F)F)c3)OC(=O)N12] | (1R,5S,7aS)-1-[3,5-bis(trifluoromethyl)phenyl]-5-[2-(2-methoxypyridin-3-yl)-5-(trifluoromethyl)phenyl]tetrahydro-1H-pyrrolo[1,2-c][1,3]oxazol-3-one | 316.3 | Calc'd 591.1, found 591.4 |
| 22 | 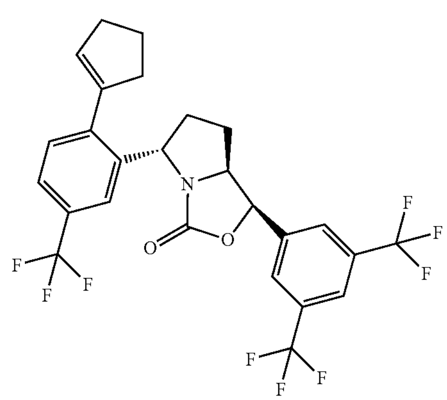 [SMILES: O=C1O[C@H](c2cc(C(F)(F)F)cc(C(F)(F)F)c2)[C@@H]2CC[C@@H](c3cc(C(F)(F)F)ccc3C3=CCCC3)N12] | (1R,5S,7aS)-1-[3,5-bis(trifluoromethyl)phenyl]-5-[2-cyclopent-1-en-1-yl-5-(trifluoromethyl)phenyl]tetrahydro-1H-pyrrolo[1,2-c][1,3]oxazol-3-one | 56.63 | Calc'd 550.1, found 550.4 |

TABLE 4-continued

| Ex | Structure | IUPAC Name | IC$_{50}$ (nM) | Exact Mass [M + H]+ |
|----|-----------|------------|----------------|---------------------|
| 23 | 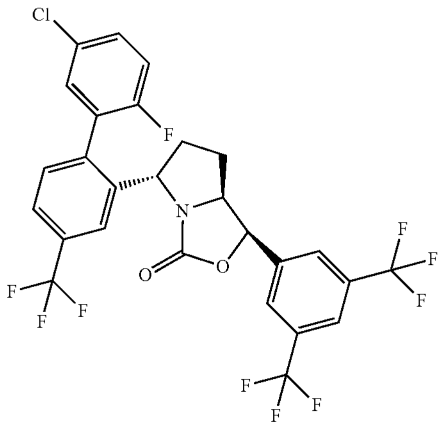 [SMILES: O=C1O[C@H](c2cc(C(F)(F)F)cc(C(F)(F)F)c2)[C@@H]2CC[C@@H](c3cc(C(F)(F)F)ccc3-c3cc(Cl)ccc3F)N12] | (1R,5S,7aS)-1-[3,5-bis(trifluoromethyl)phenyl]-5-[5'-chloro-2'-fluoro-4-(trifluoromethyl)biphenyl-2-yl]tetrahydro-1H-pyrrolo[1,2-c][1,3]oxazol-3-one | 187.5 | Calc'd 612.1, found 612.5 |
| 24 | 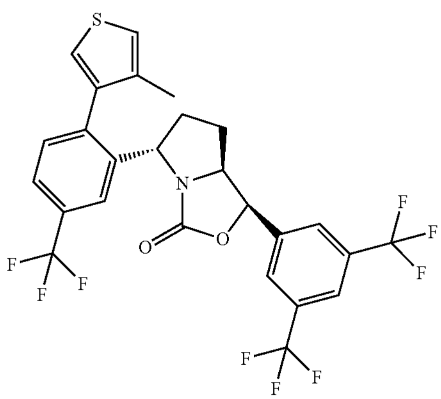 | (1R,5S,7aS)-1-[3,5-bis(trifluoromethyl)phenyl]-5-[2-(4-methylthiophen-3-yl)-5-(trifluoromethyl)phenyl]tetrahydro-1H-pyrrolo[1,2-c][1,3]oxazol-3-one | 122.2 | [M − H]⁻ Calc'd 578.1, found 578.4 |
| 25 | 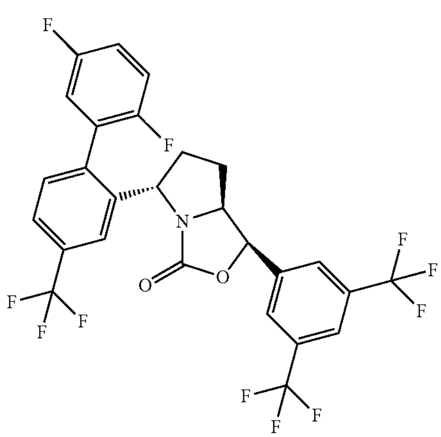 [SMILES: O=C1O[C@H](c2cc(C(F)(F)F)cc(C(F)(F)F)c2)[C@@H]2CC[C@@H](c3cc(C(F)(F)F)ccc3-c3cc(F)ccc3F)N12] | (1R,5S,7aS)-1-[3,5-bis(trifluoromethyl)phenyl]-5-[2',5'-difluoro-4-(trifluoromethyl)biphenyl-2-yl]tetrahydro-1H-pyrrolo[1,2-c][1,3]oxazol-3-one | 104.1 | Calc'd 596.1, found 596.3 |

TABLE 4-continued

| Ex | Structure | IUPAC Name | IC$_{50}$ (nM) | Exact Mass [M + H]+ |
|---|---|---|---|---|
| 26 | 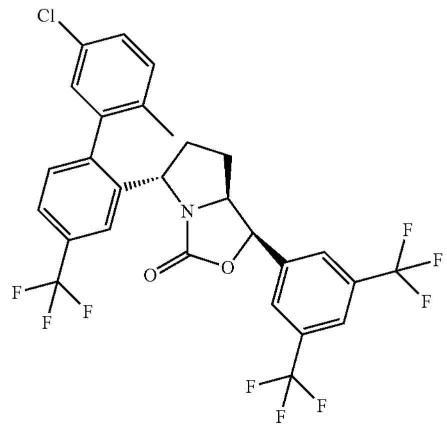 [SMILES: Cc1ccc(Cl)cc1-c1ccc(C(F)(F)F)cc1[C@@H]1CC[C@H]2[C@@H](c3cc(C(F)(F)F)cc(C(F)(F)F)c3)OC(=O)N12] | (1R,5S,7aS)-1-[3,5-bis(trifluoromethyl)phenyl]-5-[5'-chloro-2'-methyl-4-(trifluoromethyl)biphenyl-2-yl]tetrahydro-1H-pyrrolo[1,2-c][1,3]oxazol-3-one | 1223 | Calc'd 608.1, found 608.4 |
| 27 | 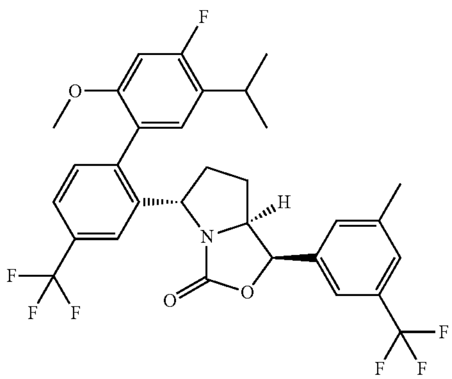 [SMILES: COc1cc(F)c(C(C)C)cc1-c1ccc(C(F)(F)F)cc1[C@@H]1CC[C@H]2[C@@H](c3cc(C)cc(C(F)(F)F)c3)OC(=O)N12] | (1R,5S,7aS)-5-[4'-fluoro-2'-methoxy-5'-(1-methylethyl)-4-(trifluoromethyl)biphenyl-2-yl]-1-[3-methyl-5-(trifluoromethyl)phenyl]tetrahydro-1H-pyrrolo[1,2-c][1,3]oxazol-3-one | 133.5 | Calc'd 596.2, found 596.3 |
| 28 | 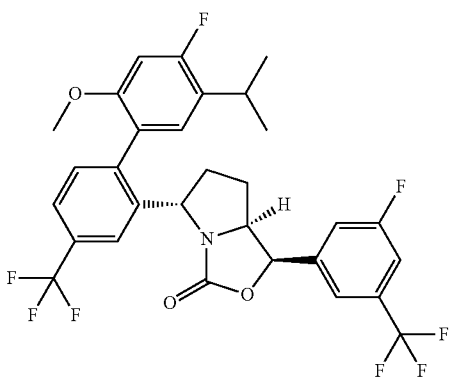 [SMILES: COc1cc(F)c(C(C)C)cc1-c1ccc(C(F)(F)F)cc1[C@@H]1CC[C@H]2[C@@H](c3cc(F)cc(C(F)(F)F)c3)OC(=O)N12] | (1R,5S,7aS)-5-[4'-fluoro-2'-methoxy-5'-(1-methylethyl)-4-(trifluoromethyl)biphenyl-2-yl]-1-[3-fluoro-5-(trifluoromethyl)phenyl]tetrahydro-1H-pyrrolo[1,2-c][1,3]oxazol-3-one | 261.5 | Calc'd 600.2, found 600.3 |
| 29 | 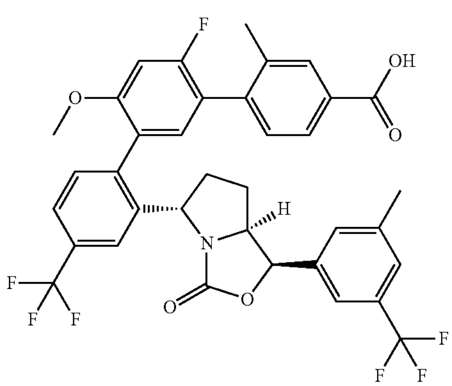 [SMILES: COc1cc(F)c(-c2ccc(C(=O)O)cc2C)cc1-c1ccc(C(F)(F)F)cc1[C@@H]1CC[C@H]2[C@@H](c3cc(C)cc(C(F)(F)F)c3)OC(=O)N12] | 6'-fluoro-4'-methoxy-2-methyl-2''-{(1R,5S,7aS)-1-[3-methyl-5-(trifluoromethyl)phenyl]-3-oxotetrahydro-1H-pyrrolo[1,2-c][1,3]oxazol-5-yl}-4'''-(trifluoromethyl)-1,1':3',1''-terphenyl-4-carboxylic acid | 44.65 | Calc'd 688.2, found 688.3 |

TABLE 4-continued

| Ex | Structure | IUPAC Name | IC$_{50}$ (nM) | Exact Mass [M + H]+ |
|---|---|---|---|---|
| 30 | 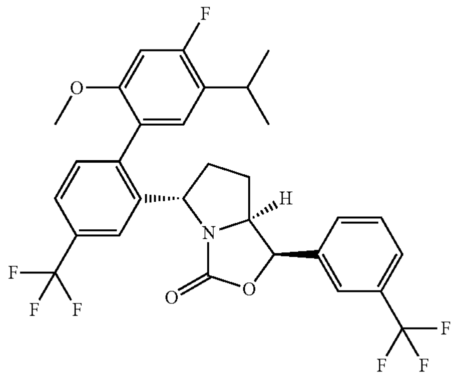 [SMILES: COc1cc(F)c(C(C)C)cc1-c1ccc(C(F)(F)F)cc1[C@@H]1CC[C@H]2[C@@H](c3cccc(C(F)(F)F)c3)OC(=O)N12] | (1R,5S,7aS)-5-[4'-fluoro-2'-methoxy-5'-(1-methylethyl)-4-(trifluoromethyl)biphenyl-2-yl]-1-[3-(trifluoromethyl)phenyl]tetrahydro-1H-pyrrolo[1,2-c][1,3]oxazol-3-one | 189.9 | Calc'd 582.2, found 582.2 |
| 31 | 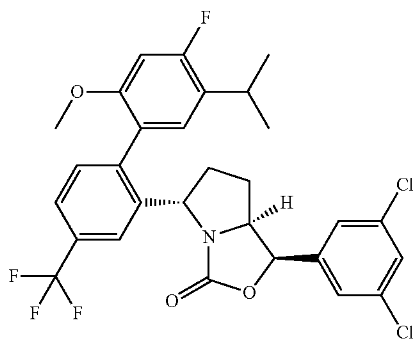 [SMILES: COc1cc(F)c(C(C)C)cc1-c1ccc(C(F)(F)F)cc1[C@@H]1CC[C@H]2[C@@H](c3cc(Cl)cc(Cl)c3)OC(=O)N12] | (1R,5S,7aS)-1-(3,5-dichlorophenyl)-5-[4'-fluoro-2'-methoxy-5'-(1-methylethyl)-4-(trifluoromethyl)biphenyl-2-yl]tetrahydro-1H-pyrrolo[1,2-c][1,3]oxazol-3-one | 213.2 | Calc'd 582.1, found 582.1 |
| 32 | 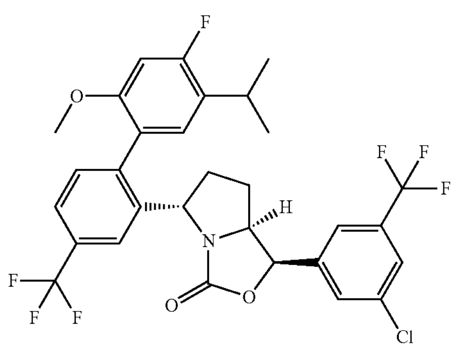 [SMILES: COc1cc(F)c(C(C)C)cc1-c1ccc(C(F)(F)F)cc1[C@@H]1CC[C@H]2[C@@H](c3cc(Cl)cc(C(F)(F)F)c3)OC(=O)N12] | (1R,5S,7aS)-1-[3-chloro-5-(trifluoromethyl)phenyl]-5-[4'-fluoro-2'-methoxy-5'-(1-methylethyl)-4-(trifluoromethyl)biphenyl-2-yl]tetrahydro-1H-pyrrolo[1,2-c][1,3]oxazol-3-one | 147.7 | Calc'd 616.1, found 616.1 |
| 33 | 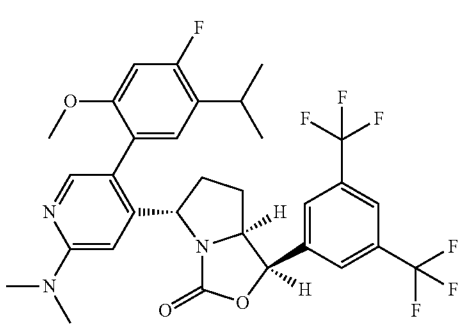 [SMILES: COc1cc(F)c(C(C)C)cc1-c1cnc(N(C)C)cc1[C@@H]1CC[C@H]2[C@@H](c3cc(C(F)(F)F)cc(C(F)(F)F)c3)OC(=O)N12] | (1R,5S,7aS)-1-[3,5-bis(trifluoromethyl)phenyl]-5-{2-(dimethylamino)-5-[4-fluoro-2-methoxy-5-(1-methylethyl)phenyl]pyridin-4-yl}tetrahydro-1H-pyrrolo[1,2-c][1,3]oxazol-3-one | 108.2 | Calc'd 626.2, found 626.3 |

TABLE 4-continued

| Ex | Structure | IUPAC Name | IC$_{50}$ (nM) | Exact Mass [M + H]+ |
|---|---|---|---|---|
| 34 | 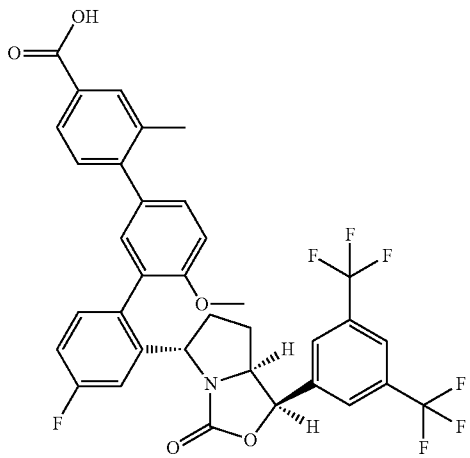 [SMILES: COc1ccc(-c2ccc(C(=O)O)cc2C)cc1-c1ccc(F)cc1[C@@H]1CC[C@H]2[C@@H](c3cc(C(F)(F)F)cc(C(F)(F)F)c3)OC(=O)N12] | 2''-{(1R,5S,7aS)-1-[3,5-bis(trifluoromethyl)phenyl]-3-oxotetrahydro-1H-pyrrolo[1,2-c][1,3]oxazol-5-yl}-4''-fluoro-4'-methoxy-2-methyl-1,1':3',1''-terphenyl-4-carboxylic acid | 228.9 | Calc'd 674.2, found 674.4 |
| 35 | 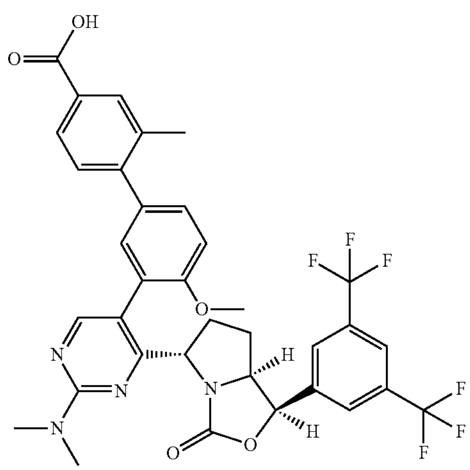 [SMILES: COc1ccc(-c2ccc(C(=O)O)cc2C)cc1-c1cnc(N(C)C)nc1[C@@H]1CC[C@H]2[C@@H](c3cc(C(F)(F)F)cc(C(F)(F)F)c3)OC(=O)N12] | 3'-[4-{(1R,5S,7aS)-1-[3,5-bis(trifluoromethyl)phenyl]-3-oxotetrahydro-1H-pyrrolo[1,2-c][1,3]oxazol-5-yl}-2-(dimethylamino)pyrimidin-5-yl]-4'-methoxy-2-methylbiphenyl-4-carboxylic acid | 431.9 | Calc'd 701.2, found 701.2 |
| 36 | 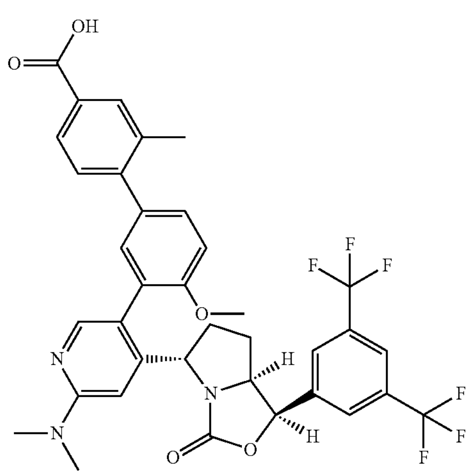 [SMILES: COc1ccc(-c2ccc(C(=O)O)cc2C)cc1-c1cnc(N(C)C)cc1[C@@H]1CC[C@H]2[C@@H](c3cc(C(F)(F)F)cc(C(F)(F)F)c3)OC(=O)N12] | 3'-[4-{(1R,5S,7aS)-1-[3,5-bis(trifluoromethyl)phenyl]-3-oxotetrahydro-1H-pyrrolo[1,2-c][1,3]oxazol-5-yl}-6-(dimethylamino)pyridin-3-yl]-4'-methoxy-2-methylbiphenyl-4-carboxylic acid | 275.6 | Calc'd 700.2, found 700.2 |

TABLE 4-continued

| Ex | Structure | IUPAC Name | IC$_{50}$ (nM) | Exact Mass [M + H]+ |
|---|---|---|---|---|
| 37 | 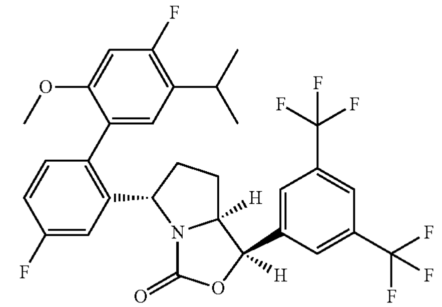 [SMILES: COc1cc(F)c(C(C)C)cc1-c1ccc(F)cc1[C@@H]1CC[C@H]2[C@@H](c3cc(C(F)(F)F)cc(C(F)(F)F)c3)OC(=O)N12] | (1R,5S,7aS)-1-[3,5-bis(trifluoromethyl)phenyl]-5-[4,4'-difluoro-2'-methoxy-5'-(1-methylethyl)biphenyl-2-yl]tetrahydro-1H-pyrrolo[1,2-c][1,3]oxazol-3-one | 474.5 | Calc'd 600.2, found 600.3 |
| 38 | 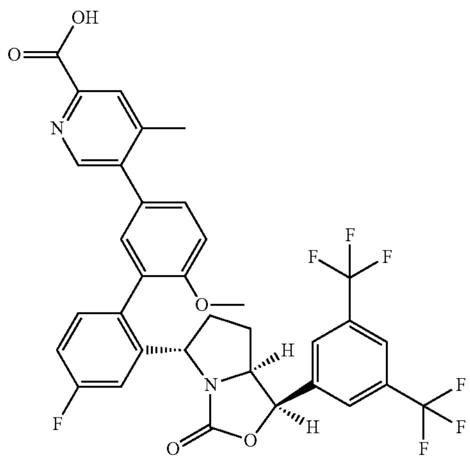 [SMILES: COc1ccc(-c2cnc(C(=O)O)cc2C)cc1-c1ccc(F)cc1[C@@H]1CC[C@H]2[C@@H](c3cc(C(F)(F)F)cc(C(F)(F)F)c3)OC(=O)N12] | 5-(2'-{(1R,5S,7aS)-1-[3,5-bis(trifluoromethyl)phenyl]-3-oxotetrahydro-1H-pyrrolo[1,2-c][1,3]oxazol-5-yl}-4'-fluoro-6-methoxybiphenyl-3-yl)-4-methylpyridine-2-carboxylic acid | 1742 | Calc'd 675.2, found 675.4 |
| 39 | 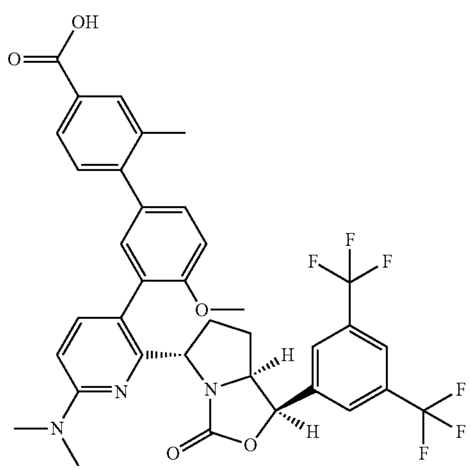 [SMILES: COc1ccc(-c2ccc(C(=O)O)cc2C)cc1-c1ccc(N(C)C)nc1[C@@H]1CC[C@H]2[C@@H](c3cc(C(F)(F)F)cc(C(F)(F)F)c3)OC(=O)N12] | 3'-[2-{(1R,5S,7aS)-1-[3,5-bis(trifluoromethyl)phenyl]-3-oxotetrahydro-1H-pyrrolo[1,2-c][1,3]oxazol-5-yl}-6-(dimethylamino)pyridin-3-yl]-4'-methoxy-2-methylbiphenyl-4-carboxylic acid | 714 | Calc'd 700.2, found 700.4 |
| 40 | 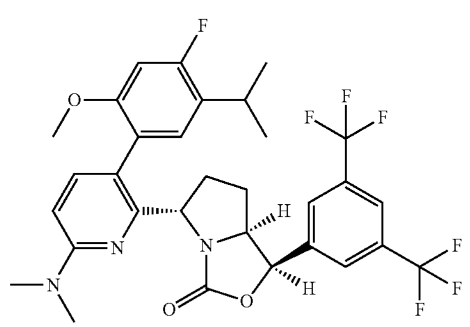 [SMILES: COc1cc(F)c(C(C)C)cc1-c1ccc(N(C)C)nc1[C@@H]1CC[C@H]2[C@@H](c3cc(C(F)(F)F)cc(C(F)(F)F)c3)OC(=O)N12] | (1R,5S,7aS)-1-[3,5-bis(trifluoromethyl)phenyl]-5-{6-(dimethylamino)-3-[4-fluoro-2-methoxy-5-(propan-2-yl)phenyl]pyridin-2-yl}tetrahydro-1H-pyrrolo[1,2-c][1,3]oxazol-3-one | 889.9 | Calc'd 626.2, found 626.0 |

TABLE 4-continued

| Ex | Structure | IUPAC Name | IC$_{50}$ (nM) | Exact Mass [M + H]+ |
|---|---|---|---|---|
| 41 | 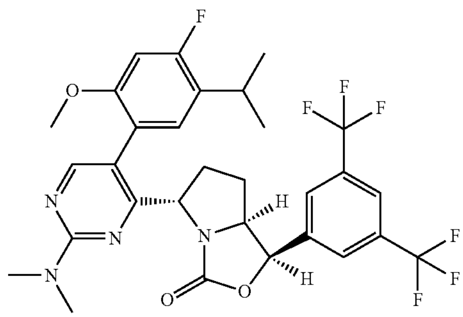 [SMILES: COc1cc(F)c(C(C)C)cc1-c1cnc(N(C)C)nc1[C@@H]1CC[C@H]2[C@@H](c3cc(C(F)(F)F)cc(C(F)(F)F)c3)OC(=O)N12] | (1R,5S,7aS)-1-[3,5-bis(trifluoromethyl)phenyl]-5-{2-(dimethylamino)-5-[4-fluoro-2-methoxy-5-(1-methylethyl)phenyl]pyrimidin-4-yl}tetrahydro-1H-pyrrolo[1,2-c][1,3]oxazol-3-one | 1138 | Calc'd 627.2, found 672.2 |
| 42 | 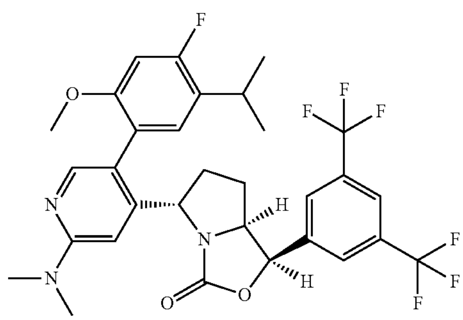 [SMILES: COc1cc(F)c(C(C)C)cc1-c1cnc(N(C)C)cc1[C@@H]1CC[C@H]2[C@@H](c3cc(C(F)(F)F)cc(C(F)(F)F)c3)OC(=O)N12] | (1R,5S,7aS)-1-[3,5-bis(trifluoromethyl)phenyl]-5-{2-(dimethylamino)-5-[4-fluoro-2-methoxy-5-(1-methylethyl)phenyl]pyridin-4-yl}tetrahydro-1H-pyrrolo[1,2-c][1,3]oxazol-3-one | 69.73 | Calc'd 626.2, found 626.5 |
| 43 | 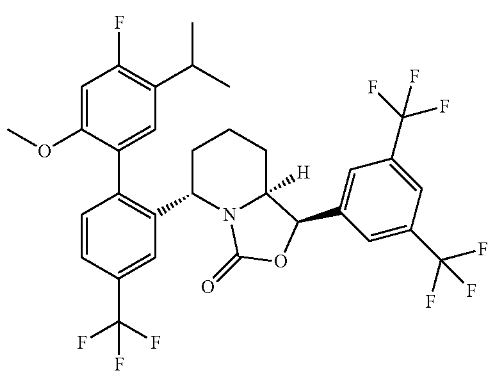 [SMILES: COc1cc(F)c(C(C)C)cc1-c1ccc(C(F)(F)F)cc1[C@@H]1CCC[C@H]2[C@@H](c3cc(C(F)(F)F)cc(C(F)(F)F)c3)OC(=O)N12] | (1R,5S,8aS)-1-[3,5-bis(trifluoromethyl)phenyl]-5-[4'-fluoro-2'-methoxy-5'-(1-methylethyl)-4-(trifluoromethyl)biphenyl-2-yl]hexahydro[1,3]oxazolo[3,4-a]pyridin-3-one | 1208 | Calc'd 664.2, found 664.3 |
| 44 | 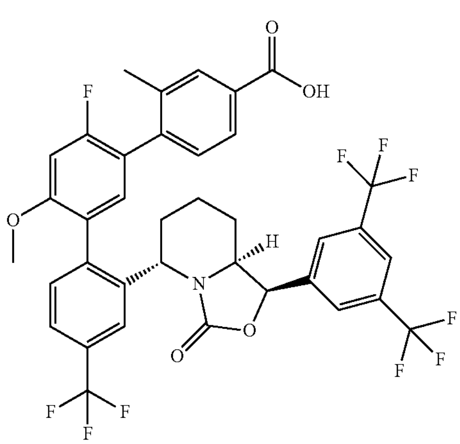 [SMILES: COc1cc(F)c(-c2ccc(C(=O)O)cc2C)cc1-c1ccc(C(F)(F)F)cc1[C@@H]1CCC[C@H]2[C@@H](c3cc(C(F)(F)F)cc(C(F)(F)F)c3)OC(=O)N12] | 2''-{(1R,5S,8aS)-1-[3,5-bis(trifluoromethyl)phenyl]-3-oxohexahydro[1,3]oxazolo[3,4-a]pyridin-5-yl}-6'-fluoro-4'-methoxy-2-methyl-4''-(trifluoromethyl)-1,1':3',1''-terphenyl-4-carboxylic acid | 717.5 | Calc'd 756.2, found 756.3 |

TABLE 4-continued

| Ex | Structure | IUPAC Name | IC$_{50}$ (nM) | Exact Mass [M + H]+ |
|---|---|---|---|---|
| 45 | 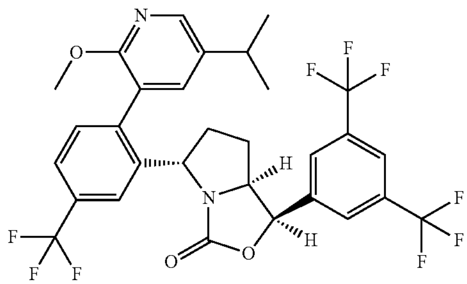 [SMILES: COc1ncc(C(C)C)cc1-c1ccc(C(F)(F)F)cc1[C@@H]1CC[C@H]2[C@@H](c3cc(C(F)(F)F)cc(C(F)(F)F)c3)OC(=O)N12] | (1R,5S,7aS)-1-[3,5-bis(trifluoromethyl)phenyl]-5-{2-[2-methoxy-5-(1-methylethyl)pyridin-3-yl]-5-(trifluoromethyl)phenyl}tetrahydro-1H-pyrrolo[1,2-c][1,3]oxazol-3-one | 44.66 | Calc'd 633.2, found 633.4 |
| 46 | 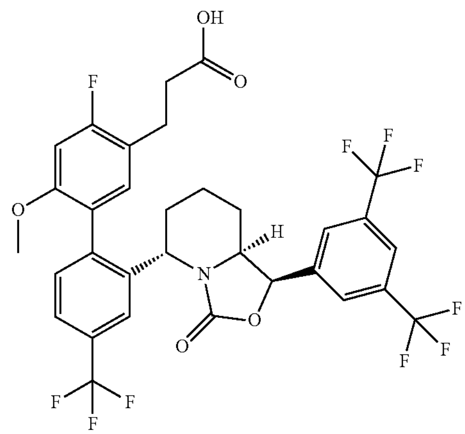 [SMILES: COc1cc(F)c(CCC(=O)O)cc1-c1ccc(C(F)(F)F)cc1[C@@H]1CCC[C@H]2[C@@H](c3cc(C(F)(F)F)cc(C(F)(F)F)c3)OC(=O)N12] | 3-[2'-{(1R,5S,8aS)-1-[3,5-bis(trifluoromethyl)phenyl]-3-oxohexahydro[1,3]oxazolo[3,4-a]pyridin-5-yl}-4-fluoro-6-methoxy-4'-(trifluoromethyl)biphenyl-3-yl]propanoic acid | 1629 | Calc'd 694.2, found 694.2 |
| 47 | 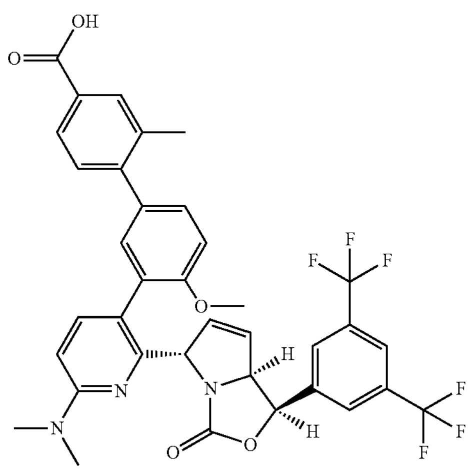 [SMILES: COc1ccc(-c2ccc(C(=O)O)cc2C)cc1-c1ccc(N(C)C)nc1[C@@H]1C=C[C@H]2[C@@H](c3cc(C(F)(F)F)cc(C(F)(F)F)c3)OC(=O)N12] | 3'-[2-{(1R,5S,7aS)-1-[3,5-bis(trifluoromethyl)phenyl]-3-oxo-5,7a-dihydro-1H-pyrrolo[1,2-c][1,3]oxazol-5-yl}-6-(dimethylamino)pyridin-3-yl]-4'-methoxy-2-methylbiphenyl-4-carboxylic acid | 490.8 | Calc'd 698.2, found 698.3 |
| 48 | 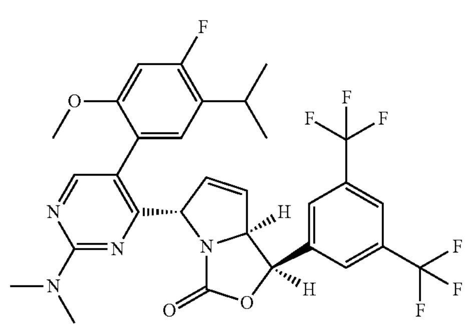 [SMILES: COc1cc(F)c(C(C)C)cc1-c1cnc(N(C)C)nc1[C@@H]1C=C[C@H]2[C@@H](c3cc(C(F)(F)F)cc(C(F)(F)F)c3)OC(=O)N12] | (1R,5S,7aS)-1-[3,5-bis(trifluoromethyl)phenyl]-5-{2-(dimethylamino)-5-[4-fluoro-2-methoxy-5-(1-methylethyl)phenyl]pyrimidin-4-yl}-5,7a-dihydro-1H-pyrrolo[1,2-c][1,3]oxazol-3-one | 694.7 | Calc'd 625.2, found 625.1 |

TABLE 4-continued

| Ex | Structure | IUPAC Name | IC$_{50}$ (nM) | Exact Mass [M + H]+ |
|---|---|---|---|---|
| 49 | 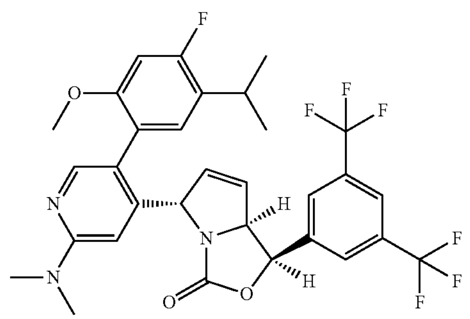 [SMILES: COc1cc(F)c(C(C)C)cc1-c1cnc(N(C)C)cc1[C@@H]1C=C[C@H]2[C@@H](c3cc(C(F)(F)F)cc(C(F)(F)F)c3)OC(=O)N12] | (1R,5S,7aS)-1-[3,5-bis(trifluoromethyl)phenyl]-5-{2-(dimethylamino)-5-[4-fluoro-2-methoxy-5-(1-methylethyl)phenyl]pyridin-4-yl}-5,7a-dihydro-1H-pyrrolo[1,2-c][1,3]oxazol-3-one | 438.3 | Calc'd 624.2, found 624.5 |
| 50 | 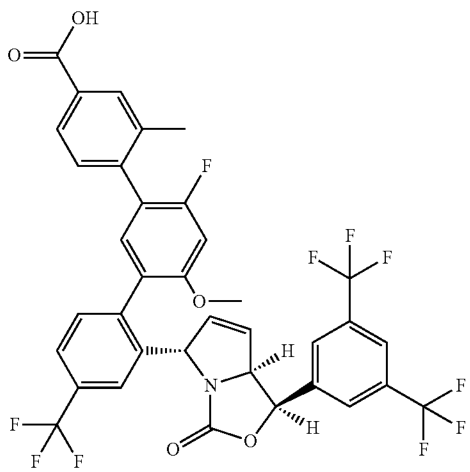 [SMILES: COc1cc(F)c(-c2ccc(C(=O)O)cc2C)cc1-c1ccc(C(F)(F)F)cc1[C@@H]1C=C[C@H]2[C@@H](c3cc(C(F)(F)F)cc(C(F)(F)F)c3)OC(=O)N12] | 2''-{(1R,5S,7aS)-1-[3,5-bis(trifluoromethyl)phenyl]-3-oxo-5,7a-dihydro-1H-pyrrolo[1,2-c][1,3]oxazol-5-yl}-6'-fluoro-4'-methoxy-2-methyl-4''-(trifluoromethyl)-1,1':3',1''-terphenyl-4-carboxylic acid | 47.94 | Calc'd 740.1, found 740.5 |
| 51 | 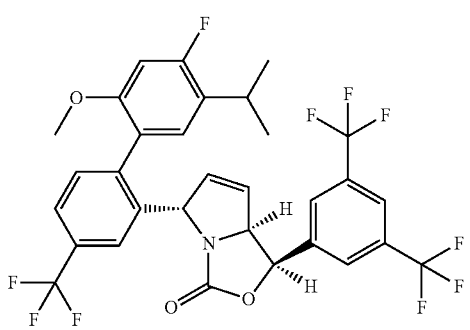 [SMILES: COc1cc(F)c(C(C)C)cc1-c1ccc(C(F)(F)F)cc1[C@@H]1C=C[C@H]2[C@@H](c3cc(C(F)(F)F)cc(C(F)(F)F)c3)OC(=O)N12] | (1R,5S,7aS)-1-[3,5-bis(trifluoromethyl)phenyl]-5-[4'-fluoro-2'-methoxy-5'-(1-methylethyl)-4-(trifluoromethyl)biphenyl-2-yl]-5,7a-dihydro-1H-pyrrolo[1,2-c][1,3]oxazol-3-one | 122 | Calc'd 648.2, found 648.4 |
| 52 | 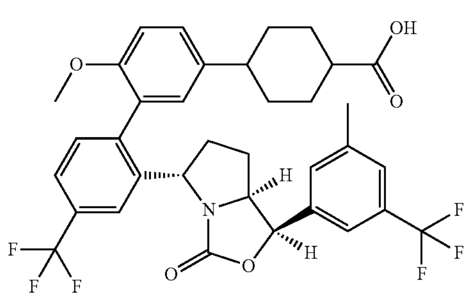 [SMILES: COc1ccc(C2CCC(C(=O)O)CC2)cc1-c1ccc(C(F)(F)F)cc1[C@@H]1CC[C@H]2[C@@H](c3cc(C)cc(C(F)(F)F)c3)OC(=O)N12] | 4-[6-methoxy-2'-{(1R,5S,7aS)-1-[3-methyl-5-(trifluoromethyl)phenyl]-3-oxotetrahydro-1H-pyrrolo[1,2-c][1,3]oxazol-5-yl}-4'-(trifluoromethyl)biphenyl-3-yl]cyclohexanecarboxylic acid | 260 | Calc'd 662.0, found 662.1 |

TABLE 4-continued

| Ex | Structure | IUPAC Name | IC$_{50}$ (nM) | Exact Mass [M + H]+ |
|---|---|---|---|---|
| 53 | 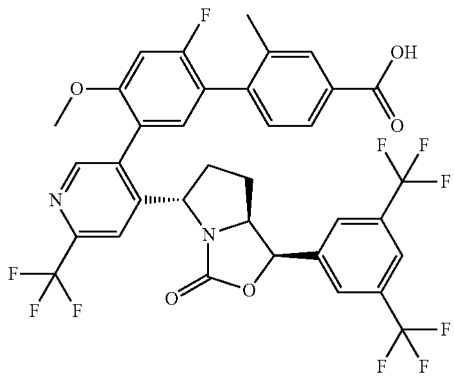 | 5'-[4-{(1R,5S,7aS)-1-[3,5-bis(trifluoromethyl)phenyl]-3-oxotetrahydro-1H-pyrrolo[1,2-c][1,3]oxazol-5-yl}-6-(trifluoromethyl)pyridin-3-yl]-2'-fluoro-4'-methoxy-2-methylbiphenyl-4-carboxylic acid | 191 | Calc'd 743.0, found 743.5 |
| 54 | 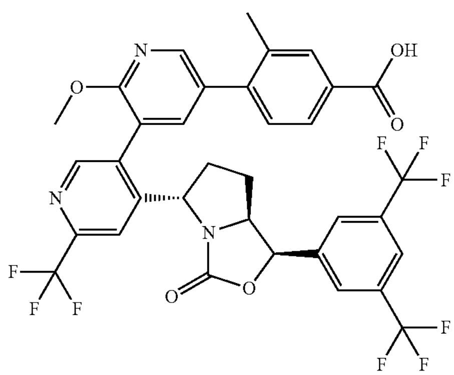 [SMILES: COc1ncc(-c2ccc(C(=O)O)cc2C)cc1-c1cnc(C(F)(F)F)cc1[C@@H]1CC[C@H]2[C@@H](c3cc(C(F)(F)F)cc(C(F)(F)F)c3)OC(=O)N12] | 4-[4'-{(1R,5S,7aS)-1-[3,5-bis(trifluoromethyl)phenyl]-3-oxotetrahydro-1H-pyrrolo[1,2-c][1,3]oxazol-5-yl}-2-methoxy-6'-(trifluoromethyl)-3,3'-bipyridin-5-yl]-3-methylbenzoic acid | 141 | Calc'd 726.0, Found 726.4 |
| 55 | 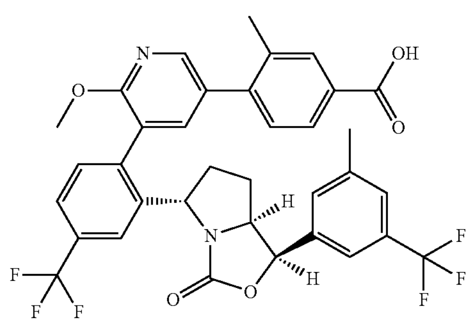 [SMILES: COc1ncc(-c2ccc(C(=O)O)cc2C)cc1-c1ccc(C(F)(F)F)cc1[C@@H]1CC[C@H]2[C@@H](c3cc(C)cc(C(F)(F)F)c3)OC(=O)N12] | 4-{6-methoxy-5-[2-{(1R,5S,7aS)-1-[3-methyl-5-(trifluoromethyl)phenyl]-3-oxotetrahydro-1H-pyrrolo[1,2-c][1,3]oxazol-5-yl}-4-(trifluoromethyl)phenyl]pyridin-3-yl}-3-methylbenzoic acid | 85 | Calc'd 671.0, Found 671.2 |
| 56 | 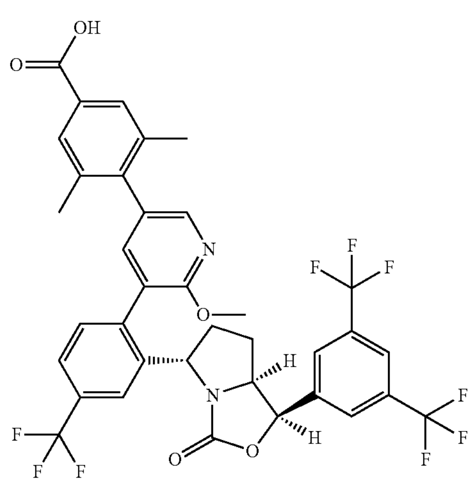 [SMILES: COc1ncc(-c2c(C)cc(C(=O)O)cc2C)cc1-c1ccc(C(F)(F)F)cc1[C@@H]1CC[C@H]2[C@@H](c3cc(C(F)(F)F)cc(C(F)(F)F)c3)OC(=O)N12] | 4-{5-[2-{(1R,5S,7aS)-1-[3,5-bis(trifluoromethyl)phenyl]-3-oxotetrahydro-1H-pyrrolo[1,2-c][1,3]oxazol-5-yl}-4-(trifluoromethyl)phenyl]-6-methoxypyridin-3-yl}-3,5-dimethylbenzoic acid | 47 | Calc'd 739.0, Found 739.4 |

TABLE 4-continued

| Ex | Structure | IUPAC Name | IC$_{50}$ (nM) | Exact Mass [M + H]+ |
|---|---|---|---|---|
| 57 | 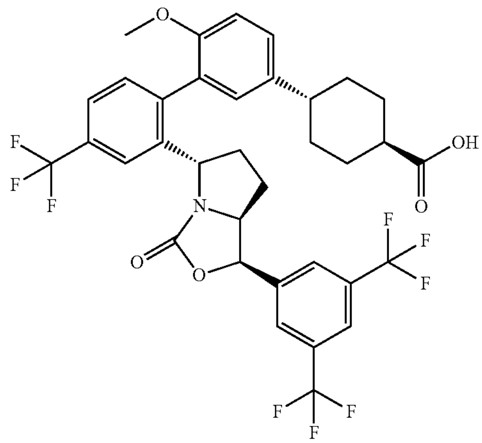 [SMILES: COc1ccc([C@H]2CC[C@H](C(=O)O)CC2)cc1-c1ccc(C(F)(F)F)cc1[C@@H]1CC[C@H]2[C@@H](c3cc(C(F)(F)F)cc(C(F)(F)F)c3)OC(=O)N12] | trans-4-[2'-{(1R,5S,7aS)-1-[3,5-bis(trifluoromethyl)phenyl]-3-oxotetrahydro-1H-pyrrolo[1,2-c][1,3]oxazol-5-yl}-6-methoxy-4'-(trifluoromethyl)biphenyl-3-yl]cyclohexanecarboxylic acid | 242 | Calc'd 716.0, Found 716.5 |
| 58 | 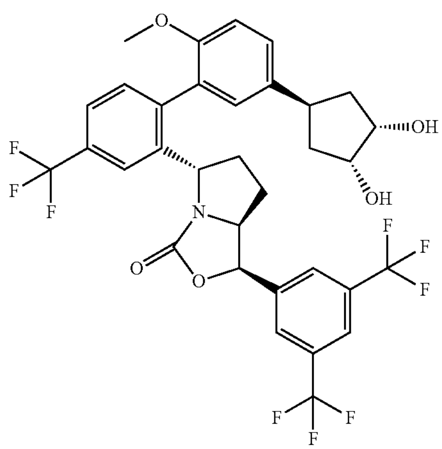 [SMILES: COc1ccc([C@@H]2C[C@@H](O)[C@@H](O)C2)cc1-c1ccc(C(F)(F)F)cc1[C@@H]1CC[C@H]2[C@@H](c3cc(C(F)(F)F)cc(C(F)(F)F)c3)OC(=O)N12] | (1R,5S,7aS)-1-[3,5-bis(trifluoromethyl)phenyl]-5-{5'-[(1s,3R,4S)-3,4-dihydroxycyclopentyl]-2'-methoxy-4-(trifluoromethyl)phenyl-2-yl}tetrahydro-1H-pyrrolo[1,2-c][1,3]oxazol-3-one | 418 | Calc'd 690.0, Found 690.5 |
| 59 | 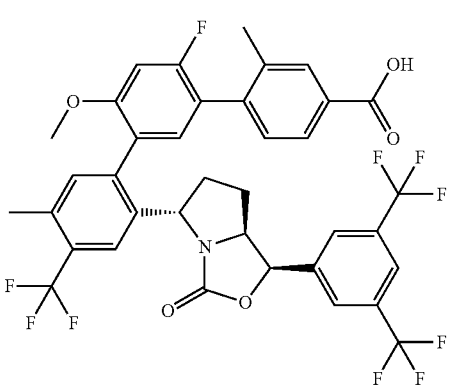 [SMILES: COc1cc(F)c(-c2ccc(C(=O)O)cc2C)cc1-c1cc(C)c(C(F)(F)F)cc1[C@@H]1CC[C@H]2[C@@H](c3cc(C(F)(F)F)cc(C(F)(F)F)c3)OC(=O)N12] | 2''-{(1R,5S,7aS)-1-[3,5-bis(trifluoromethyl)phenyl]-3-oxotetrahydro-1H-pyrrolo[1,2-c][1,3]oxazol-5-yl}-6'-fluoro-4'-methoxy-2,5''-dimethyl-4''-(trifluoromethyl)-1,1':3',1''-terphenyl-4-carboxylic acid | 120 | Calc'd 756.0, Found 756.1 |

TABLE 4-continued

| Ex | Structure | IUPAC Name | IC$_{50}$ (nM) | Exact Mass [M + H]+ |
|---|---|---|---|---|
| 60 | 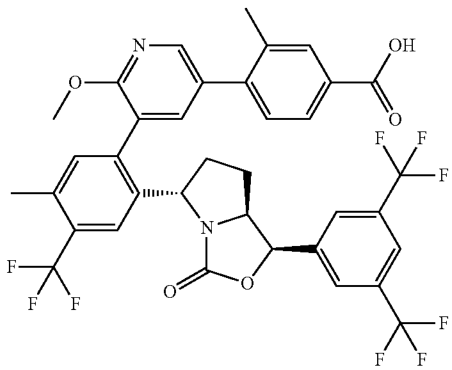 [SMILES: COc1ncc(-c2ccc(C(=O)O)cc2C)cc1-c1cc(C)c(C(F)(F)F)cc1[C@@H]1CC[C@H]2[C@@H](c3cc(C(F)(F)F)cc(C(F)(F)F)c3)OC(=O)N12] | 4-{5-[2-{(1R,5S,7aS)-1-[3,5-bis(trifluoromethyl)phenyl]-3-oxotetrahydro-1H-pyrrolo[1,2-c][1,3]oxazol-5-yl}-5-methyl-4-(trifluoromethyl)phenyl]-6-methoxypyridin-3-yl}-3-methylbenzoic acid | 106 | Calc'd 739.0, Found 739.1 |
| 61 | 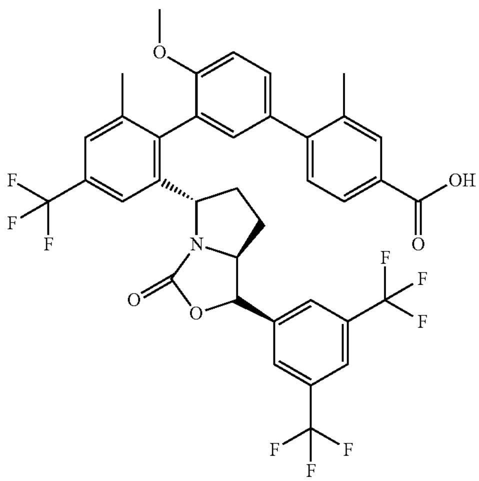 | 2''-{(1R,5S,7aS)-1-[3,5-bis(trifluoromethyl)phenyl]-3-oxotetrahydro-1H-pyrrolo[1,2-c][1,3]oxazol-5-yl}-4'-methoxy-2,6''-dimethyl-4''-(trifluoromethyl)-1,1':3',1''-terphenyl-4-carboxylic acid | 87 | Calc'd 738.0, Found 738.2 |
| 62 | 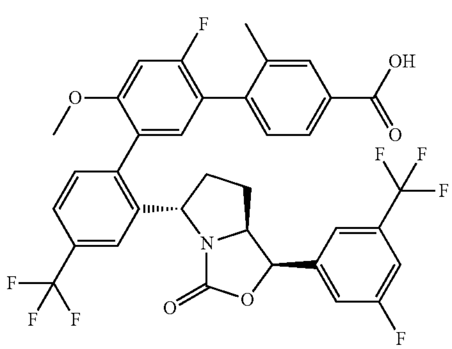 [SMILES: COc1cc(F)c(-c2ccc(C(=O)O)cc2C)cc1-c1ccc(C(F)(F)F)cc1[C@@H]1CC[C@H]2[C@@H](c3cc(F)cc(C(F)(F)F)c3)OC(=O)N12] | 6'-fluoro-2''-{(1R,5S,7aS)-1-[3-fluoro-5-(trifluoromethyl)phenyl]-3-oxotetrahydro-1H-pyrrolo[1,2-c][1,3]oxazol-5-yl}-4'-methoxy-2-methyl-4''-(trifluoromethyl)-1,1':3',1''-terphenyl-4-carboxylic acid | 172 | Calc'd 692.0, Found 692.0 |
| 63 | 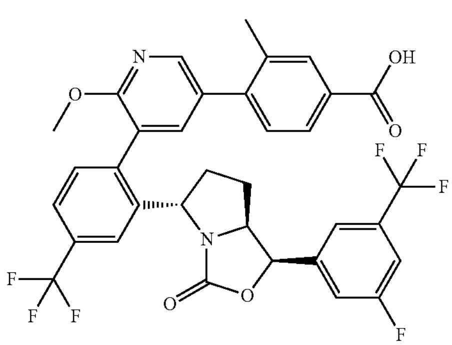 [SMILES: COc1ncc(-c2ccc(C(=O)O)cc2C)cc1-c1ccc(C(F)(F)F)cc1[C@@H]1CC[C@H]2[C@@H](c3cc(F)cc(C(F)(F)F)c3)OC(=O)N12] | 4-{5-[2-{(1R,5S,7aS)-1-[3-fluoro-5-(trifluoromethyl)phenyl]-3-oxotetrahydor-1H-pyrrolo[1,2-c][1,3]oxazol-5-yl}-4-(trifluoromethyl)phenyl]-6-methoxypyridin-3-yl}-3-methylbenzoic acid | 136 | Calc'd 675.0, Found 675.0 |

TABLE 4-continued

| Ex | Structure | IUPAC Name | IC$_{50}$ (nM) | Exact Mass [M + H]+ |
|---|---|---|---|---|
| 64 | 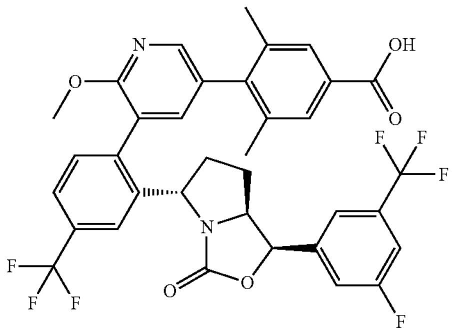 [SMILES: COc1ncc(-c2c(C)cc(C(=O)O)cc2C)cc1-c1ccc(C(F)(F)F)cc1[C@@H]1CC[C@H]2[C@@H](c3cc(F)cc(C(F)(F)F)c3)OC(=O)N12] | 4-{5-[2-{(1R,5S,7aS)-1-[3-fluoro-5-(trifluoromethyl)phenyl]-3-oxotetrahydro-1H-pyrrolo[1,2-c][1,3]oxazol-5-yl}-4-(trifluoromethyl)phenyl]-6-methoxypyridin-3-yl}-3,5-dimethylbenzoic acid | 77 | Calc'd 689.0, Found 689.2 |
| 65 | 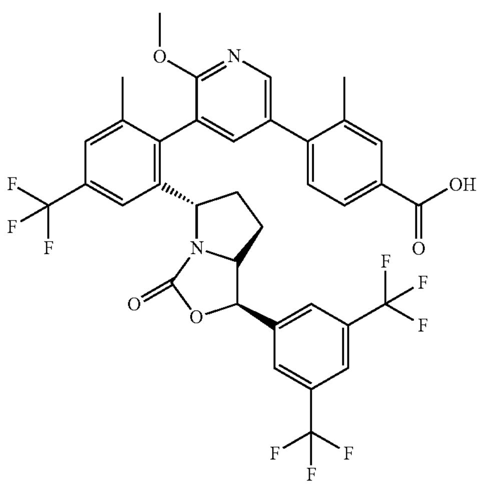 | 4-{5-[2-{(1R,5S,7aS)-1-[3,5-bis(trifluoromethyl)phenyl]-3-oxotetrahydro-1H-pyrrolo[1,2-c][1,3]oxazol-5-yl}-6-methyl-4-(trifluoromethyl)phenyl]-6-methoxypyridin-3-yl}-3-methylbenzoic acid | 124 | Calc'd 739.0, Found 739.1 |
| 66 | 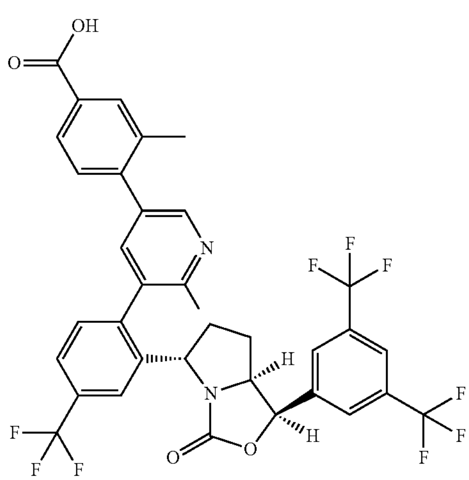 [SMILES: Cc1cc(C(=O)O)ccc1-c1cnc(C)c(-c2ccc(C(F)(F)F)cc2[C@@H]2CC[C@H]3[C@@H](c4cc(C(F)(F)F)cc(C(F)(F)F)c4)OC(=O)N23)c1] | 4-{5-[2-{(1R,5S,7aS)-1-[3,5-bis(trifluoromethyl)phenyl]-3-oxotetrahydro-1H-pyrrolo[1,2-c][1,3]oxazol-5-yl}-4-(trifluoromethyl)phenyl]-6-methylpyridin-3-yl}-3-methylbenzoic acid | 1292 | Calc'd 709.0, Found 709.1 |

TABLE 4-continued

| Ex | Structure | IUPAC Name | IC$_{50}$ (nM) | Exact Mass [M + H]+ |
|----|-----------|------------|----------------|---------------------|
| 67 | 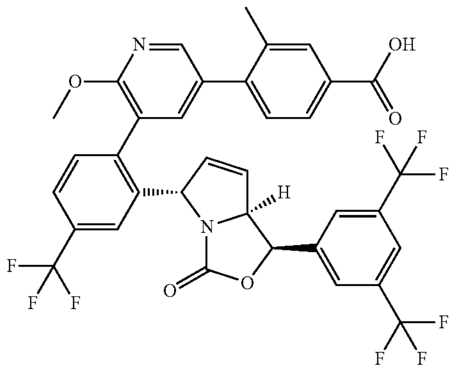 [SMILES: COc1ncc(-c2ccc(C(=O)O)cc2C)cc1-c1ccc(C(F)(F)F)cc1[C@@H]1C=C[C@H]2[C@@H](c3cc(C(F)(F)F)cc(C(F)(F)F)c3)OC(=O)N12] | 4-(5-(2-((1R,5S,7aS)-1-(3,5-bis(trifluoromethyl)phenyl)-3-oxo-1,3,5,7a-tetrahydropyrrolo[1,2-c]oxazol-5-yl)-4-(trifluoromethyl)phenyl)-6-methoxypyridin-3-yl)-3-methylbenzoic acid | 199 | Calc'd 723.2, Found 723.1 |
| 68 | 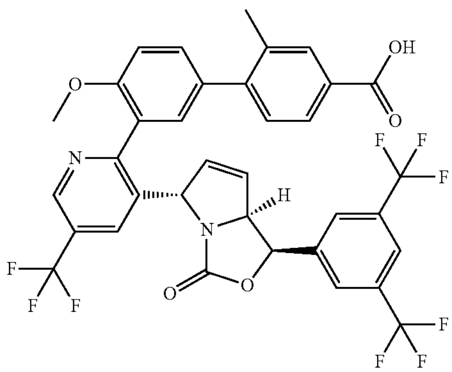 [SMILES: COc1ccc(-c2ccc(C(=O)O)cc2C)cc1-c1ncc(C(F)(F)F)cc1[C@@H]1C=C[C@H]2[C@@H](c3cc(C(F)(F)F)cc(C(F)(F)F)c3)OC(=O)N12] | 3'-(3-((1R,5S,7aS)-1-(3,5-bis(trifluoromethyl)phenyl)-3-oxo-1,3,5,7a-tetrahydropyrrolo[1,2-c]oxazol-5-yl)-5-(trifluoromethyl)pyridin-2-yl)-4'-methoxy-2-methyl-[1,1'-biphenyl]-4-carboxylic acid | 424 | Calc'd 723.2, Found 723.1 |
| 69 | 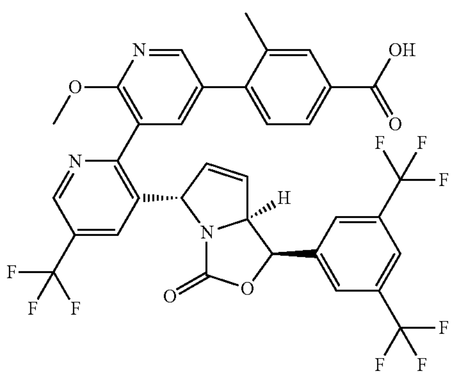 [SMILES: COc1ncc(-c2ccc(C(=O)O)cc2C)cc1-c1ncc(C(F)(F)F)cc1[C@@H]1C=C[C@H]2[C@@H](c3cc(C(F)(F)F)cc(C(F)(F)F)c3)OC(=O)N12] | 4-(3-((1R,5S,7aS)-1-(3,5-bis(trifluoromethyl)phenyl)-3-oxo-1,3,5,7a-tetrahydropyrrolo[1,2-c]oxazol-5-yl)-2'-methoxy-5-(trifluoromethyl)-[2,3'-bipyridin]-5'-yl)-3-methylbenzoic acid | 456 | Calc'd 724.1, Found 724.1 |
| 70 | 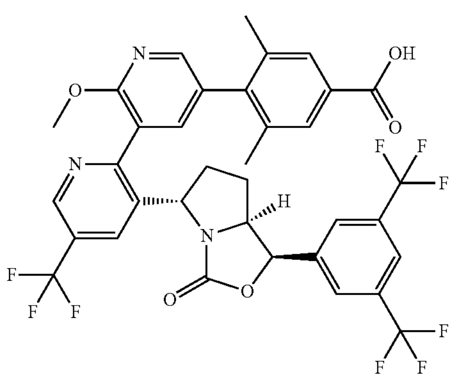 [SMILES: COc1ncc(-c2c(C)cc(C(=O)O)cc2C)cc1-c1ncc(C(F)(F)F)cc1[C@@H]1CC[C@H]2[C@@H](c3cc(C(F)(F)F)cc(C(F)(F)F)c3)OC(=O)N12] | 4-[3-{(1R,5S,7aS)-1-[3,5-bis(trifluoromethyl)phenyl]-3-oxotetrahydro-1H-pyrrolo[1,2-c][1,3]oxazol-5-yl}-2'-methoxy-5-(trifluoromethyl)-2,3'-bipyridin-5'-yl]-3,5-dimethylbenzoic acid | 751 | Calc'd 740.0, Found 740.3 |

TABLE 4-continued

| Ex | Structure | IUPAC Name | IC$_{50}$ (nM) | Exact Mass [M + H]+ |
|---|---|---|---|---|
| 71 | 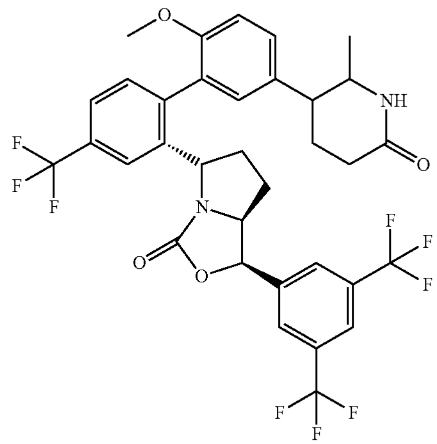 | (1R,5S,7aS)-1-[3,5-bis(trifluoromethyl)phenyl]-5-[2'-methoxy-5'-(2-methyl-6-oxopiperidin-3-yl)-4-(trifluoromethyl)biphenyl-2-yl]tetrahydro-1H-pyrrolo[1,2-c][1,3]oxazol-3-one | 198 | Calc'd 701.0, Found 701.1 |
| 72 | 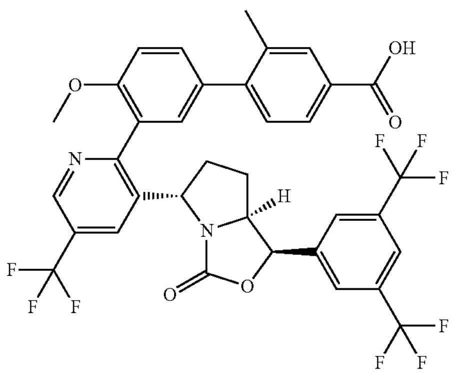 [SMILES: COc1ccc(-c2ccc(C(=O)O)cc2C)cc1-c1ncc(C(F)(F)F)cc1[C@@H]1CC[C@H]2[C@@H](c3cc(C(F)(F)F)cc(C(F)(F)F)c3)OC(=O)N12] | 3'-[3-{(1R,5S,7aS)-1-[3,5-bis(trifluoromethyl)phenyl]-3-oxotetrahydro-1H-pyrrolo[1,2-c][1,3]oxazol-5-yl}-5-(trifluoromethyl)pyridin-2-yl]-4'-methoxy-2-methylbiphenyl-4-carboxylic acid | 427 | Calc'd 725.0, Found 725.2 |
| 73 | 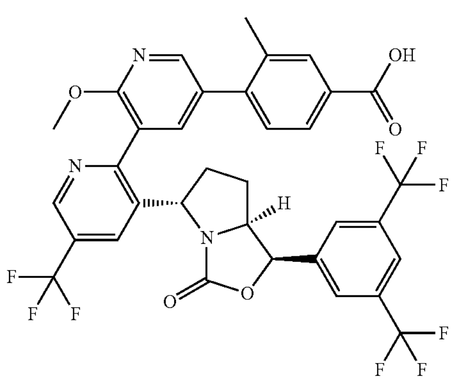 [SMILES: COc1ncc(-c2ccc(C(=O)O)cc2C)cc1-c1ncc(C(F)(F)F)cc1[C@@H]1CC[C@H]2[C@@H](c3cc(C(F)(F)F)cc(C(F)(F)F)c3)OC(=O)N12] | 4-[3-{(1R,5S,7aS)-1-[3,5-bis(trifluoromethyl)phenyl]-3-oxotetrahydro-1H-pyrrolo[1,2-c][1,3]oxazol-5-yl}-2'-methoxy-5-(trifluoromethyl)-2,3'-bipyridin-5'-yl]-3-methylbenzoic acid | 287 | Calc'd 726.0, Found 726.2 |

TABLE 4-continued

| Ex | Structure | IUPAC Name | IC$_{50}$ (nM) | Exact Mass [M + H]+ |
|---|---|---|---|---|
| 74 | 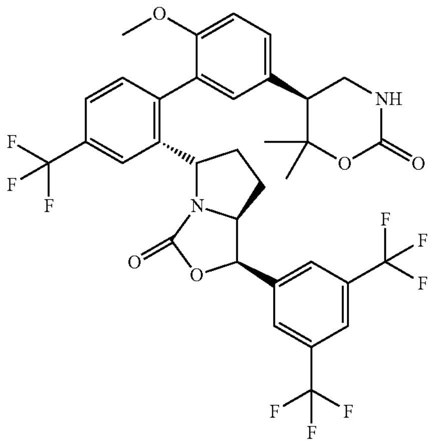 | (1R,5S,7aS)-1-[3,5-bis(trifluoromethyl)phenyl]-5-{5'-[(5S)-6,6-dimethyl-2-oxo-1,3-oxazinan-5-yl]-2'-methoxy-4-(trifluoromethyl)biphenyl-2-yl}tetrahydro-1H-pyrrolo[1,2-c][1,3]oxazol-3-one | 246 | Calc'd 717.0, found 717.0 |
| 75 | 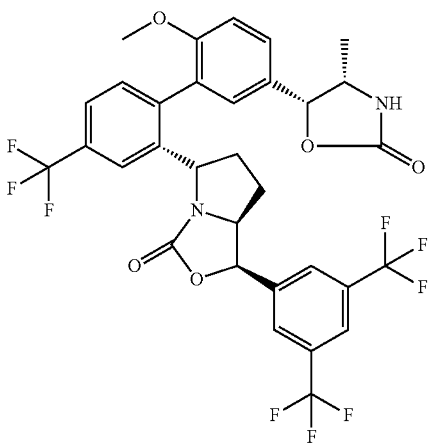 | (1R,5S,7aS)-1-[3,5-bis(trifluoromethyl)phenyl]-5-{2'-methoxy-5'-[(4S,5R)-4-methyl-2-oxo-1,3-oxazolidin-5-yl]-4-(trifluoromethyl)biphenyl-2-yl}tetrahydro-1H-pyrrolo[1,2-c][1,3]oxazol-3-one | 89 | Calc'd 689.0, Found 689.2 |
| 76 | 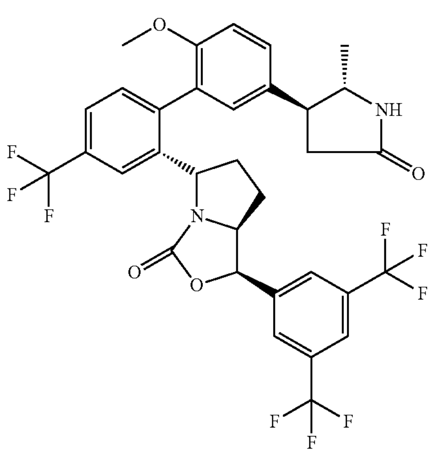 | (1R,5S,7aS)-1-[3,5-bis(trifluoromethyl)phenyl]-5-{2'-methoxy-5'-[(2S,3S)-2-methyl-5-oxopyrrolidin-3-yl]-4-(trifluoromethyl)biphenyl-2-yl}tetrahydro-1H-pyrrolo[1,2-c][1,3]oxazol-3-one | 466 | Calc'd 687.0, Found 686.9 |

TABLE 4-continued

| Ex | Structure | IUPAC Name | IC$_{50}$ (nM) | Exact Mass [M + H]+ |
|---|---|---|---|---|
| 77 | 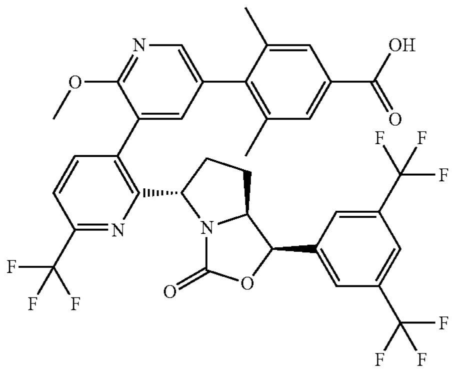 [SMILES: COc1ncc(-c2c(C)cc(C(=O)O)cc2C)cc1-c1ccc(C(F)(F)F)nc1[C@@H]1CC[C@H]2[C@@H](c3cc(C(F)(F)F)cc(C(F)(F)F)c3)OC(=O)N12] | 4-[2'-{(1R,5S,7aS)-1-[3,5-bis(trifluoromethyl)phenyl]-3-oxotetrahydro-1H-pyrrolo[1,2-c][1,3]oxazol-5-yl}-2-methoxy-6'-(trifluoromethyl)-3,3'-bipyridin-5-yl]-3,5-dimethylbenzoic acid | 561 | Calc'd 740.0, Found 740.2 |
| 78 | 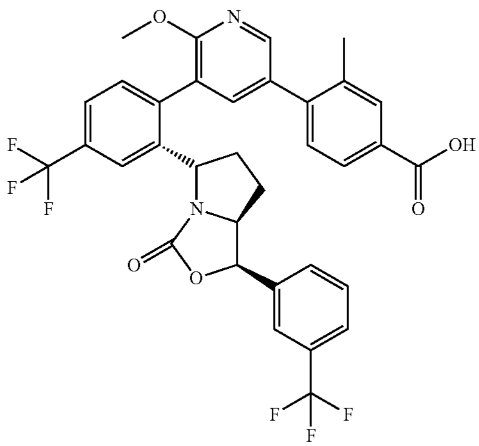 | 4-{6-methoxy-5-[2-{(1R,5S,7aS)-3-oxo-1-[3-(trifluoromethyl)phenyl]tetrahydro-1H-pyrrolo[1,2-c][1,3]oxazol-5-yl}-4-(trifluoromethyl)phenyl]pyridin-3-yl}-3-methylbenzoic acid | 864 | Calc'd 657.0, Found 657.1 |

Example 79

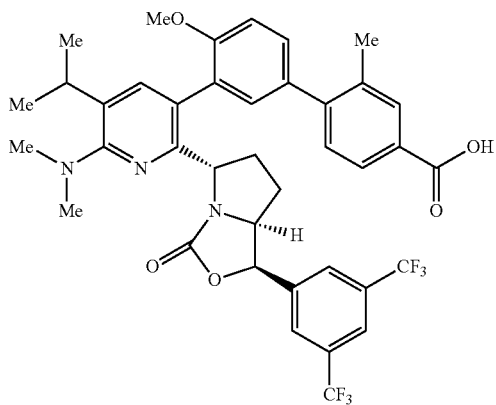 [SMILES: COc1ccc(-c2ccc(C(=O)O)cc2C)cc1-c1cc(C(C)C)c(N(C)C)nc1[C@@H]1CC[C@H]2[C@@H](c3cc(C(F)(F)F)cc(C(F)(F)F)c3)OC(=O)N12]

3'-[2-{(1R,5S,7aS)-1-[3,5-bis(trifluoromethyl)phenyl]-3-oxotetrahydro-1H-pyrrolo[1,2-c][1,3]oxazol-5-yl}-6-(dimethylamino)-5-(propan-2-yl)pyridin-3-yl]-4'-methoxy-2-methylbiphenyl-4-carboxylic acid
(Scheme 2)

Step 1: To a slurry of (1R,5S,7aS)-1-[3,5-bis(trifluoromethyl)phenyl]-5-[3-bromo-6-(dimethylamino)pyridin-2-yl]tetrahydro-1H-pyrrolo[1,2-c][1,3]oxazol-3-one (200 mg, 0.372 mmol) in MeOH (7.25 mL) under nitrogen at room temperature was added silver sulfate (116 mg, 0.372 mmol), followed by iodine (94 mg, 0.372 mmol). The resulting mixture was stirred for 1 hour. The reaction was partitioned with ethyl acetate and aqueous sodium hydroxide (1.0 M). The organic was then washed with aqueous saturated sodium thiosulfate and the combined aqueous layers were extracted with ethyl acetate. The combined organics were washed with brine, dried over magnesium sulfate, filtered, and concentrated in vacuo. The residue was purified by flash column chromatography to yield (1R,5S,7aS)-1-[3,5-bis(trifluoromethyl)phenyl]-5-[3-bromo-6-(dimethylamino)-5-iodopyridin-2-yl]tetrahydro-1H-pyrrolo[1,2-c][1,3]oxazol-3-one (180 mg, 0.271 mmol). MS ESI calc'd. for $C_{21}H_{18}BrF_6N_3O_2$ [M+H]+ 666.0, found 666.1.

Step 2: To (1R,5S,7aS)-1-[3,5-bis(trifluoromethyl)phenyl]-5-[3-bromo-6-(dimethylamino)-5-iodopyridin-2-yl]tetrahydro-1H-pyrrolo[1,2-c][1,3]oxazol-3-one (50 mg, 0.075 mmol) in DMF (1 mL) was added isopropenylboronic acid pinacol ester (13.9 mg, 0.083 mmol), dichloro[1,1'-bis(diphenylphosphino)ferrocene]palladium(II) dichloromethane adduct (1.84 mg, 2.26 mmol) and potassium carbonate (0.5 M in water, 0.30 mL, 0.151 mmol). The system was stirred at 50° C. overnight before cooling and partitioning with water and ethyl acetate. The organic layer was washed with brine, dried over sodium sulfate, and concentrated before purifying by column chromatography to yield (1R,5S,7aS)-1-[3,5-bis(trifluoromethyl)phenyl]-5-[3-bromo-6-(dimethylamino)-5-(prop-1-en-2-yl)pyridin-2-yl]tetrahydro-1H-pyrrolo[1,2-c][1,3]oxazol-3-one (19 mg, 0.033 mmol). MS ESI calc'd. for $C_{24}H_{23}BrF_6N_3O_2$ [M+H]+ 580.1, found 580.2.

Step 3: To (1R,5S,7aS)-1-[3,5-bis(trifluoromethyl)phenyl]-5-[3-bromo-6-(dimethylamino)-5-(prop-1-en-2-yl)pyridin-2-yl]tetrahydro-1H-pyrrolo[1,2-c][1,3]oxazol-3-one (19 mg, 0.033 mmol) in THF (0.5 mL) was added methyl 4'-methoxy-2-methyl-3'-(4,4,5,5-tetramethyl-1,3,2-dioxaborolan-2-yl)biphenyl-4-carboxylate (18.8 mg, 0.049 mmol), dichloro[1,1'-bis(diphenylphosphino)ferrocene]palladium(II) (2.14 mg, 3.29 mmol) and potassium carbonate (2.0 M in water, 0.049 mL, 0.100 mmol). The system was stirred at room temperature overnight. The reaction was directly purified by column chromatography to yield (1R,5S,7aS)-1-[3,5-bis(trifluoromethyl)phenyl]-5-[3-bromo-6-(dimethylamino)-5-(prop-1-en-2-yl)pyridin-2-yl]tetrahydro-1H-pyrrolo[1,2-c][1,3]oxazol-3-one (24 mg, 0.033 mmol). MS ESI calc'd. for $C_{40}H_{38}F_6N_3O_5$ [M+H]+ 754.3, found 754.4.

Step 4: To (1R,5S,7aS)-1-[3,5-bis(trifluoromethyl)phenyl]-5-[3-bromo-6-(dimethylamino)-5-(prop-1-en-2-yl)pyridin-2-yl]tetrahydro-1H-pyrrolo[1,2-c][1,3]oxazol-3-one (24 mg, 0.033 mmol) in ethanol (5 mL) was added palladium on carbon (0.54 mg, 5.04 mmol). The system was stirred at room temperature under a hydrogen atmosphere for 2 days. The reaction was filtered and the filtrate was concentrated. Crude methyl 3'-[2-{(1R,5S,7aS)-1-[3,5-bis(trifluoromethyl)phenyl]-3-oxotetrahydro-1H-pyrrolo[1,2-c][1,3]oxazol-5-yl}-6-(dimethylamino)-5-(propan-2-yl)pyridin-3-yl]-4'-methoxy-2-methylbiphenyl-4-carboxylate (24 mg, 0.033 mmol) was carried forward without further purification. MS ESI calc'd. for $C_{40}H_{40}F_6N_3O_5$ [M+H]+ 756.3, found 756.4.

Step 5: To methyl 3'-[2-{(1R,5S,7aS)-1-[3,5-bis(trifluoromethyl)phenyl]-3-oxotetrahydro-1H-pyrrolo[1,2-c][1,3]oxazol-5-yl}-6-(dimethylamino)-5-(propan-2-yl)pyridin-3-yl]-4'-methoxy-2-methylbiphenyl-4-carboxylate (24 mg, 0.033 mmol) in THF (1 mL) was added lithium hydroxide (9.51 mg, 0.397 mmol). The reaction was stirred overnight at room temperature. Reaction was incomplete. More lithium hydroxide (4.76 mg, 1.99 mmol) was added, and the reaction was heated to 50° C. for 5 hours. The reaction was purified by HPLC to yield 3'-[2-{(1R,5S,7aS)-1-[3,5-bis(trifluoromethyl)phenyl]-3-oxotetrahydro-1H-pyrrolo[1,2-c][1,3]oxazol-5-yl}-6-(dimethylamino)-5-(propan-2-yl)pyridin-3-yl]-4'-methoxy-2-methylbiphenyl-4-carboxylic acid (10 mg, 0.012 mmol). $^1$H NMR indicated that this compound exists as a pair of rotamers at 1.6:1 ratio. $^1$H NMR (500 MHz, CDCl$_3$) δ7.94-8.10 (m, 2H), 7.90 (s, 1H), 7.84 (s, 2H), 7.48 (m, 2H), 7.42 (dd, J=8.5 Hz, J=2.0 Hz, 1H), 7.37 (d, J=7.5 Hz, 1H, minor rotamer), 7.30 (d, 1H, merged with solvent peak, major rotamer), 7.14 (d, J=8.5 Hz, 1H, minor rotamer), 7.07 (d, J=8.5 Hz, 1H, major rotamer), 5.98 (d, J=8.0 Hz, 1H, minor rotamer), 5.93 (d, J=8.0 Hz, 1H, major rotamer), 5.09 (t, J=7.5 Hz, 1H, minor rotamer), 5.01 (t, J=7.5 Hz, 1H, major rotamer), 4.76 (m, 1H), 3.93 (s, 3H, minor rotamer), 3.83 (s, 3H, major rotamer), 3.40 (m, 1H), 3.07 (s, 6H), 2.47 (s, 3H, major rotamer), 2.40 (s, 3H, minor rotamer), 2.35 (m, 1H), 2.05 (m, 1H), 1.60 (m, 1H), 1.29 (t, J=6.5 Hz, 6H), 1.08 (m, 1H). MS ESI calc'd. for $C_{39}H_{38}F_6N_3O_5$ [M+H]+ 742.3, found 742.5. RTA (95% HS): 182 nM Example 80

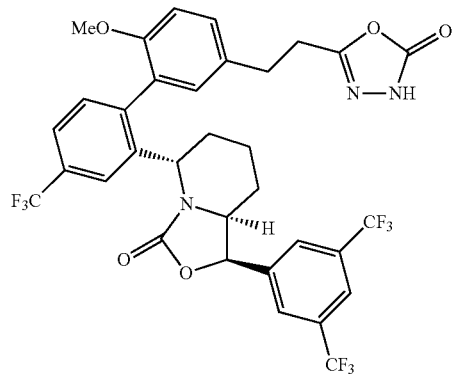 [SMILES: COc1ccc(CCc2n[nH]c(=O)o2)cc1-c1ccc(C(F)(F)F)cc1[C@@H]1CCC[C@H]2[C@@H](c3cc(C(F)(F)F)cc(C(F)(F)F)c3)OC(=O)N12]

(1R,5S,8aS)-1-[3,5-bis(trifluoromethyl)phenyl]-5-{2'-methoxy-5'-[2-(5-oxo-4,5-dihydro-1,3,4-oxadiazol-2-yl)ethyl]-4-(trifluoromethyl)biphenyl-2-yl}hexahydro[1,3]oxazolo[3,4-a]pyridin-3-one
(Scheme 3)

Step 1: To methyl 3-[2'-{(1R,5S,8aS)-1-[3,5-bis(trifluoromethyl)phenyl]-3-oxohexahydro[1,3]oxazolo[3,4-a]pyridin-5-yl}-6-methoxy-4'-(trifluoromethyl)biphenyl-3-yl]propanoate (30 mg, 0.044 mmol) was added ethanol (2 mL) followed by hydrazine hydrate (21.8 mg, 0.435 mmol). The mixture was heated for 150° C. by microwave irradiation for an hour. The crude reaction was concentrated and 3-[2'-{(1R,5S,8aS)-1-[3,5-bis(trifluoromethyl)phenyl]-3-oxohexahydro[1,3]oxazolo[3,4-a]pyridin-5-yl}-6-methoxy-4'-(trifluoromethyl)biphenyl-3-yl]propanehydrazide (27 mg, 0.039 mmol) was carried forward without further purification. MS ESI calc'd. for $C_{32}H_{29}F_9N_3O_4$ [M+H]+ 690.2, found 690.2.

Step 2: To 3-[2'-{(1R,5S,8aS)-1-[3,5-bis(trifluoromethyl)phenyl]-3-oxohexahydro[1,3]oxazolo[3,4-a]pyridin-5-yl}-6-methoxy-4'-(trifluoromethyl)biphenyl-3-yl]propanehydrazide (10 mg, 0.015 mmol) in DCM (2 mL) was added DIPEA (5.6 mg, 0.044 mmol) and phosgene (4.30 mg, 0.44 mmol). The reaction was at room temperature for 30 minutes before the reaction was directly purified by column chromatography to yield (1R,5S,8aS)-1-[3,5-bis(trifluoromethyl)phenyl]-5-{2'-methoxy-5'-[2-(5-oxo-4,5-dihydro-1,3,4-oxadiazol-2-yl)ethyl]-4-(trifluoromethyl)biphenyl-2-yl}hexahydro[1,3]oxazolo[3,4-a]pyridin-3-one (5 mg, 6.99 mmol). $^1$H NMR indicated that this compound exists as a pair of rotamers at 3:1 ratio: $^1$H NMR (500 MHz, CDCl$_3$) δ9.23 (s, 1H), 7.88 (s, 1H), 7.80 (s, 2H), 7.79 (s, 1H, minor rotamer), 7.65 (s, 2H, major rotamer) 7.62 (m, 1H) 7.4 (d, J=7.8 Hz, 1H, major rotamer), 7.25 (d, J=7.8 Hz, 1H, minor rotamer), 7.09 (s, 1H), 7.02 (m, 2H), 5.58 (m, 1H, minor rotamer) 5.42 (m, 1H, major rotamer), 4.19 (m, 1H), 3.85 (s, 3H, minor rotamer), 3.80 (s, 3H, major rotamer), 3.0-2.85 (m, 4H), 1.98 (m, 2H), 1.5-1.6 (m, 4H). MS ESI calc'd. for $C_{33}H_{27}F_9N_3O_5$ [M+H]+ 716.2, found 716.3. RTA (95% HS): 942 nM The following compound in Table 5 was prepared according to General Scheme 3 using the procedure outlined in Example 80 from compounds prepared according to General Scheme 1.

TABLE 5

| Ex | Structure | IUPAC Name | IC$_{50}$(nM) | Exact Mass [M + H]+ |
|----|-----------|------------|---------------|---------------------|
| 81 | 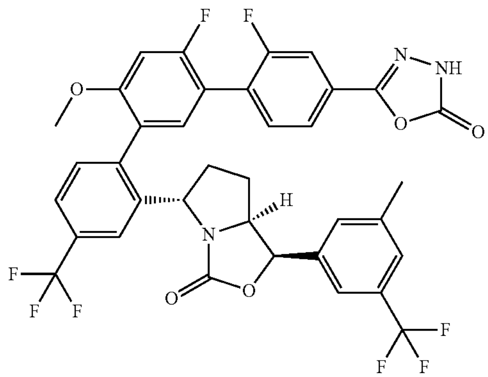 [SMILES: COc1cc(F)c(-c2ccc(-c3n[nH]c(=O)o3)cc2F)cc1-c1ccc(C(F)(F)F)cc1[C@@H]1CC[C@H]2[C@@H](c3cc(C)cc(C(F)(F)F)c3)OC(=O)N12] | (1R,5S,7aS)-5-[4'-fluoro-6'-methoxy-2''-methyl-4''-(5-oxo-4,5-dihydro-1,3,4-oxadiazol-2-yl)-4-(trifluoromethyl)-1,1':3',1''-terphenyl-2-yl]-1-[3-methyl-5-(trifluoromethyl)phenyl]tetrahydro-1H-pyrrolo[1,2-c][1,3]oxazol-3-one | 167.6 | Calc'd 728.2, found 728.3 |

Example 82

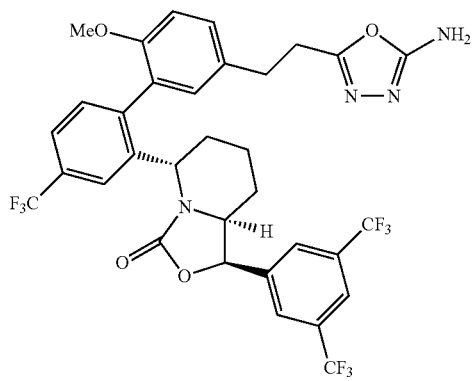 [SMILES: COc1ccc(CCc2nnc(N)o2)cc1-c1ccc(C(F)(F)F)cc1[C@@H]1CCC[C@H]2[C@@H](c3cc(C(F)(F)F)cc(C(F)(F)F)c3)OC(=O)N12]

(1R,5S,8aS)-5-{5'-[2-(5-amino-1,3,4-oxadiazol-2-yl)ethyl]-2'-methoxy-4-(trifluoromethyl)biphenyl-2-yl}-1-[3,5-bis(trifluoromethyl)phenyl]hexahydro[1,3]oxazolo[3,4-c]pyridin-3-one (Scheme 3)

To 3-[2'-{(1R,5S,8aS)-1-[3,5-bis(trifluoromethyl)phenyl]-3-oxohexahydro[1,3]oxazolo[3,4-c]pyridin-5-yl}-6-methoxy-4'-(trifluoromethyl)biphenyl-3-yl]propanehydrazide (10 mg, 0.015 mmol) in dioxane (1 mL) was added sodium bicarbonate (2.4 mg, 0.029 mmol) followed by water (0.2 mL). The system was sealed and cyanogen bromide (5.8 µL, 0.029 mmol) was added at room temperature. The reaction was complete in 5 minutes and the solvent was removed before the crude material was purified by HPLC to yield (1R,5S,8aS)-5-{5'-[2-(5-amino-1,3,4-oxadiazol-2-yl)ethyl]-2'-methoxy-4-(trifluoromethyl)biphenyl-2-yl}-1-[3,5-bis(trifluoromethyl)phenyl]hexahydro[1,3]oxazolo[3,4-c]pyridin-3-one (7 mg, 9.80 mmol). $^1$H NMR indicated that this compound exists as a pair of rotamers at 1:1 ratio. $^1$H NMR (500 MHz, CDCl$_3$) δ8.45 (br s, 1H), 8.3 (br s, 1H), 7.90 (d, J=9.2 Hz, 1H), 7.75 (m, 5H), 7.38 (t, J=8.5 Hz) 7.2 (m, 2H), 7.0 (m, 2H), 5.55 (d, J=8.9 Hz, 1H), 5.40 (d, J=8.9 Hz, 1H), 5.38 (m, 1H), 5.25 (m, 1H), 4.2 (m, 1H), 3.95 (m, 1H), 3.82 (s, 3H), 3.8 (s, 3H), 3.2-3.1 (br s, 4H), 2.2 (m, 1H), 2.12 (m, 1H), 1.80 (m, 4H). MS ESI calc'd. for C$_{33}$H$_{28}$F$_9$N$_4$O$_4$ [M+H]+ 715.2, found 715.3. RTA (95% HS): 1319 nM The following compound in Table 6 was prepared according to general Scheme 3 using the procedure outlined in Example 80 from compounds prepared according to general Scheme 1.

TABLE 6

| Ex | Structure | IUPAC Name | IC$_{50}$(nM) | Exact Mass [M + H]+ |
|----|-----------|------------|---------------|---------------------|
| 83 | 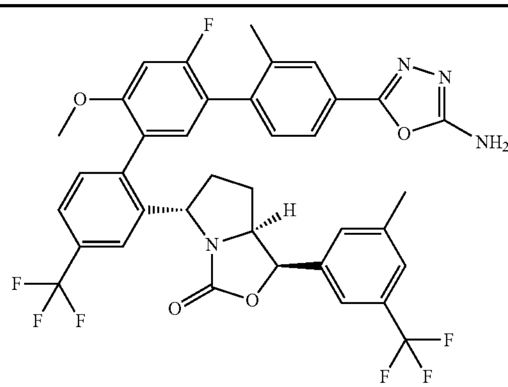 | (1R,5S,7aS)-5-[4''-(5-amino-1,3,4-oxadiazol-2-yl)-4'-fluoro-6'-methoxy-2''-methyl-4-(trifluoromethyl)-1,1':3',1''-terphenyl-2-yl]-1-[3-methyl-5-(trifluoromethyl)phenyl]tetrahydro-1H-pyrrolo[1,2-c][1,3]oxazol-3-one | 95.01 | Calc'd 727.2, found 727.3 |

What is claimed is:

1. A method of treating a disease or condition which is hypercholesterolemia or familial-hypercholesterolemia in a patient in need of such treatment comprising the administration of a therapeutically effective amount of a compound having Formula Ia,

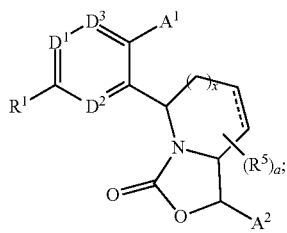

Ia or a pharmaceutically acceptable salt thereof;
wherein the dashed line in the ring in Formula Ia is an optional double bond when x is 0;
wherein R$^1$ is CF$_3$, F, or —N(CH$_3$)$_2$;
R$^5$ is H or CH$_3$;
D$^1$ is N or CR$^2$, wherein R$^2$ is H or —CH(CH$_3$)$_2$;
D$^2$ is N or CR$^3$, wherein R$^3$ is H or CH$_3$;
D$^3$ is N or CR$^4$, wherein R$^4$ is H or CH$_3$;
A$^1$ is phenyl, pyridyl, thienyl, furyl, cyclohexenyl, or cyclopentenyl,
wherein A$^1$ is optionally substituted with 1-3 groups which are each independently F, Cl, —OCH$_3$, isopropyl, —CN, —CH$_3$, or CF$_3$, and optionally one substituent group Z;
Z is A$^3$, —CH$_2$CH$_2$CO$_2$R$^8$, —CH$_2$CH$_2$-(5-oxo-4,5-dihydro-1,3,4-oxadiazol-2-yl), or —CH$_2$CH$_2$-(5-amino-1,3,4-oxadiazol-2-yl);
R$^8$ is H or —CH$_3$,
A$^3$ is phenyl, cyclobutyl, or pyridyl, wherein A$^3$ is optionally substituted with 1 group —CH$_3$, and is optionally substituted with 1 group -(5-oxo-4,5-dihydro-1,3,4-oxadiazol-2-yl), -(5-amino-1,3,4-oxadiazol-2-yl), or —CO$_2$R in which R is H or —CH$_3$;
A$^2$ is phenyl, which is substituted with 1-2 substituent groups which are each independently CF$_3$, CH$_3$, F, or Cl; and
a is 0;
to said patient.

2. The method of claim 1, wherein the method comprises the administration of the compound

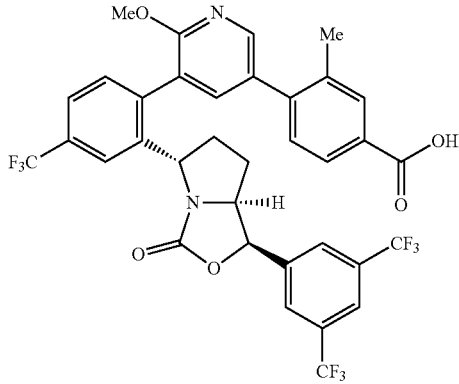 [SMILES: COc1ncc(-c2ccc(C(=O)O)cc2C)cc1-c1ccc(C(F)(F)F)cc1[C@@H]1CC[C@H]2[C@@H](c3cc(C(F)(F)F)cc(C(F)(F)F)c3)OC(=O)N12]

or a pharmaceutically acceptable salt thereof to said patient.

3. The method of claim 1, wherein the method comprises the administration of the compound

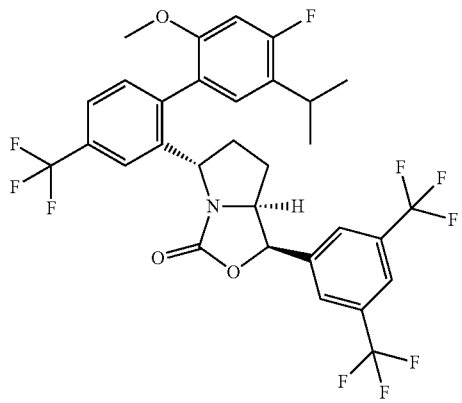 [SMILES: COc1cc(F)c(C(C)C)cc1-c1ccc(C(F)(F)F)cc1[C@@H]1CC[C@H]2[C@@H](c3cc(C(F)(F)F)cc(C(F)(F)F)c3)OC(=O)N12]

or a pharmaceutically acceptable salt thereof to said patient.

4. The method of claim 1, wherein the method comprises the administration of the compound

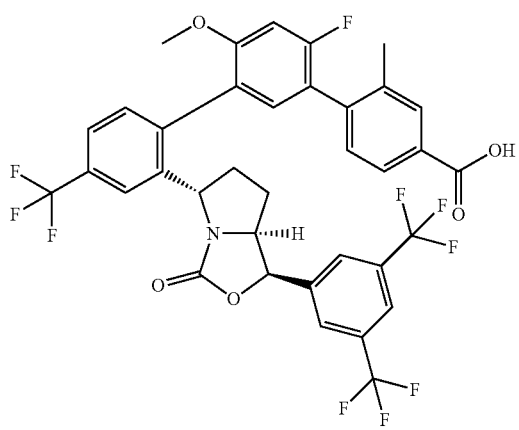 [SMILES: COc1cc(F)c(-c2ccc(C(=O)O)cc2C)cc1-c1ccc(C(F)(F)F)cc1[C@@H]1CC[C@H]2[C@@H](c3cc(C(F)(F)F)cc(C(F)(F)F)c3)OC(=O)N12]

or a pharmaceutically acceptable salt thereof to said patient.

5. The method of claim 1, wherein the method comprises the administration of the compound

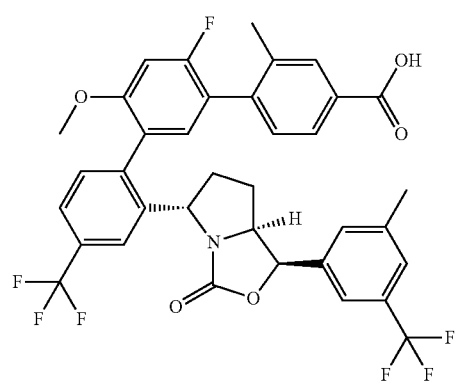 [SMILES: COc1cc(F)c(-c2ccc(C(=O)O)cc2C)cc1-c1ccc(C(F)(F)F)cc1[C@@H]1CC[C@H]2[C@@H](c3cc(C)cc(C(F)(F)F)c3)OC(=O)N12]

or a pharmaceutically acceptable salt thereof to said patient.

6. The method of claim 1, wherein the method comprises the administration of the compound

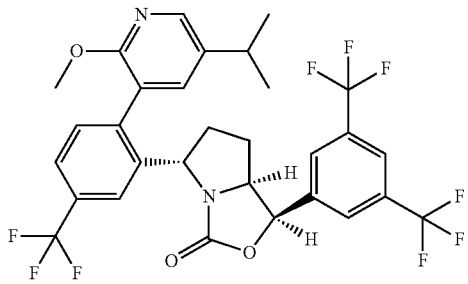 [SMILES: COc1ncc(C(C)C)cc1-c1ccc(C(F)(F)F)cc1[C@@H]1CC[C@H]2[C@@H](c3cc(C(F)(F)F)cc(C(F)(F)F)c3)OC(=O)N12]

or a pharmaceutically acceptable salt thereof to said patient.

7. The method of claim 2, wherein the disease or condition is hypercholesterolemia.

8. The method of claim 3, wherein the disease or condition is hypercholesterolemia.

9. The method of claim 4, wherein the disease or condition is hypercholesterolemia.

10. The method of claim 5, wherein the disease or condition is hypercholesterolemia.

11. The method of claim 6, wherein the disease or condition is hypercholesterolemia.

12. The method of claim 2, wherein the disease or condition is familial hypercholesterolemia.

13. The method of claim 3, wherein the disease or condition is familial hypercholesterolemia.

14. The method of claim 4, wherein the disease or condition is familial hypercholesterolemia.

15. The method of claim 5, wherein the disease or condition is familial hypercholesterolemia.

16. The method of claim 6, wherein the disease or condition is familial hypercholesterolemia.

* * * * *